US009570690B2

(12) United States Patent
Kadoma et al.

(10) Patent No.: US 9,570,690 B2
(45) Date of Patent: *Feb. 14, 2017

(54) HETEROCYCLIC COMPOUND

(71) Applicant: SEMICONDUCTOR ENERGY LABORATORY CO., LTD., Atsugi-shi, Kanagawa-ken (JP)

(72) Inventors: Hiroshi Kadoma, Kanagawa (JP); Yasushi Kitano, Kanagawa (JP); Satoko Shitagaki, Kanagawa (JP); Nobuharu Ohsawa, Kanagawa (JP); Satoshi Seo, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/734,067

(22) Filed: Jun. 9, 2015

(65) Prior Publication Data

US 2015/0270499 A1 Sep. 24, 2015

Related U.S. Application Data

(63) Continuation of application No. 13/360,058, filed on Jan. 27, 2012, now Pat. No. 9,056,856.

(30) Foreign Application Priority Data

Feb. 1, 2011 (JP) .................................. 2011-020113
Aug. 23, 2011 (JP) .................................. 2011-181467

(51) Int. Cl.
*H01L 51/00* (2006.01)
*C07D 403/10* (2006.01)
(Continued)

(52) U.S. Cl.
CPC ......... *H01L 51/0074* (2013.01); *C07D 403/10* (2013.01); *C07D 405/10* (2013.01);
(Continued)

(58) Field of Classification Search
None
See application file for complete search history.

(56) References Cited

U.S. PATENT DOCUMENTS 6,723,445 B2 4/2004 Li et al.
7,355,340 B2 4/2008 Shitagaki et al.
(Continued)

FOREIGN PATENT DOCUMENTS

CN 101203968 A 6/2008
CN 101379110 A 3/2009
(Continued)

OTHER PUBLICATIONS

European Search Report (Application No. 11155124.8) Dated Jun. 24, 2011.
(Continued)

*Primary Examiner* — J. L. Yang
(74) *Attorney, Agent, or Firm* — Fish & Richardson P.C.

(57) ABSTRACT

Provided is a novel heterocyclic compound which can be used for a light-emitting element, as a host material of a light-emitting layer in which a light-emitting substance is dispersed. A heterocyclic compound represented by a general formula (G1) is provided. In the formula, A represents any of a substituted or unsubstituted dibenzothiophenyl group, a substituted or unsubstituted dibenzofuranyl group, and a substituted or unsubstituted carbazolyl group, $R^{11}$ to $R^{19}$ separately represent any of hydrogen, an alkyl group having 1 to 4 carbon atoms, and a substituted or unsubstituted aryl group having 6 to 13 carbon atoms, and Ar
(Continued)

represents a substituted or unsubstituted arylene group having 6 to 13 carbon atoms.

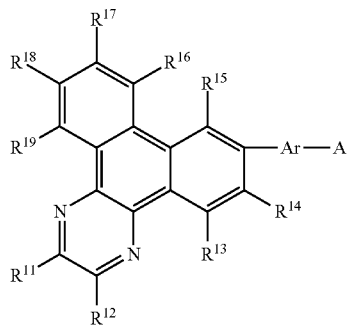

(G1)

13 Claims, 18 Drawing Sheets

(51) Int. Cl.
C07D 405/10 (2006.01)
C07D 409/10 (2006.01)
C09K 11/06 (2006.01)
H05B 33/14 (2006.01)
H01L 51/50 (2006.01)

(52) U.S. Cl.
CPC ............ *C07D 409/10* (2013.01); *C09K 11/06* (2013.01); *H01L 51/0052* (2013.01); *H01L 51/0056* (2013.01); *H01L 51/0058* (2013.01); *H01L 51/0072* (2013.01); *H01L 51/0073* (2013.01); *H05B 33/14* (2013.01); *C09K 2211/1007* (2013.01); *C09K 2211/1014* (2013.01); *C09K 2211/1029* (2013.01); *C09K 2211/1044* (2013.01); *H01L 51/5012* (2013.01); *H01L 51/5056* (2013.01); *H01L 51/5072* (2013.01)

(56) References Cited

U.S. PATENT DOCUMENTS

| | | | |
|---|---|---|---|
| 7,601,435 B2 | 10/2009 | Shitagaki et al. | |
| 7,927,720 B2 | 4/2011 | Nomura et al. | |
| 7,931,974 B2 | 4/2011 | Egawa et al. | |
| 8,017,252 B2 | 9/2011 | Iwaki et al. | |
| 8,084,146 B2 | 12/2011 | Murase et al. | |
| 8,119,259 B2 | 2/2012 | Kadoma et al. | |
| 8,138,303 B2 | 3/2012 | Chebotareva et al. | |
| 8,178,216 B2 | 5/2012 | Nomura et al. | |
| 8,231,984 B2 | 7/2012 | Shitagaki et al. | |
| 8,252,433 B2 | 8/2012 | Egawa et al. | |
| 8,252,434 B2 | 8/2012 | Iwaki et al. | |
| 8,314,101 B2 | 11/2012 | Kadoma et al. | |
| 8,541,114 B2 | 9/2013 | Iwaki et al. | |
| 8,758,905 B2 | 6/2014 | Shitagaki et al. | |
| 8,815,419 B2 | 8/2014 | Iwaki et al. | |
| 9,056,856 B2 * | 6/2015 | Kadoma | C07D 409/10 |
| 9,079,879 B2 | 7/2015 | Kadoma et al. | |
| 2005/0064237 A1 | 3/2005 | Kato et al. | |
| 2009/0026922 A1 | 1/2009 | Iwaki et al. | |
| 2009/0072718 A1 | 3/2009 | Nomura et al. | |
| 2009/0140641 A1 | 6/2009 | Nomura et al. | |
| 2009/0140642 A1 | 6/2009 | Kadoma et al. | |
| 2009/0153041 A1 | 6/2009 | Kawakami et al. | |
| 2009/0184633 A1 | 7/2009 | Kadoma et al. | |
| 2009/0203704 A1 | 8/2009 | Kadoma et al. | |
| 2010/0039024 A1 | 2/2010 | Wendeborn et al. | |
| 2010/0090588 A1 | 4/2010 | Yokoyama et al. | |
| 2010/0109514 A1 | 5/2010 | Schafer et al. | |
| 2010/0249349 A1 | 9/2010 | Chebotareva et al. | |
| 2011/0089407 A1 | 4/2011 | Schmidhalter et al. | |
| 2011/0210316 A1 | 9/2011 | Kadoma et al. | |
| 2012/0138907 A1 | 6/2012 | Murase et al. | |
| 2012/0197020 A1 | 8/2012 | Osaka et al. | |
| 2012/0286257 A1 | 11/2012 | Shitagaki et al. | |
| 2012/0313506 A1 | 12/2012 | Egawa et al. | |
| 2013/0048971 A1 | 2/2013 | Kitano et al. | |
| 2013/0060033 A1 | 3/2013 | Seo et al. | |
| 2013/0075704 A1 | 3/2013 | Takasu et al. | |
| 2013/0082591 A1 | 4/2013 | Seo et al. | |
| 2013/0112954 A1 | 5/2013 | Osaka et al. | |
| 2015/0318493 A1 | 11/2015 | Kadoma et al. | |

FOREIGN PATENT DOCUMENTS

| | | |
|---|---|---|
| CN | 101516856 A | 8/2009 |
| CN | 101687814 A | 3/2010 |
| CN | 101853923 A | 10/2010 |
| CN | 101867019 A | 10/2010 |
| CN | 101970448 A | 2/2011 |
| CN | 102190653 A | 9/2011 |
| EP | 1616864 A | 1/2006 |
| EP | 1748045 A | 1/2007 |
| EP | 1905768 A | 4/2008 |
| EP | 1962354 A | 8/2008 |
| EP | 2055704 A | 5/2009 |
| EP | 2065378 A | 6/2009 |
| EP | 2236506 A | 10/2010 |
| EP | 2363398 A | 9/2011 |
| EP | 2450356 A | 5/2012 |
| JP | 2006-324650 A | 11/2006 |
| JP | 2006-324850 A | 11/2006 |
| JP | 2007-189001 A | 7/2007 |
| JP | 2008-021665 A | 1/2008 |
| JP | 2008-106051 A | 5/2008 |
| JP | 2008-239613 A | 10/2008 |
| JP | 2009-149629 A | 7/2009 |
| JP | 2009-149631 A | 7/2009 |
| JP | 2009-149632 A | 7/2009 |
| JP | 2009-526111 | 7/2009 |
| JP | 2011-511821 | 4/2011 |
| JP | 2011-201869 A | 10/2011 |
| KR | 2008-0005441 A | 1/2008 |
| KR | 2010-0123716 A | 11/2010 |
| KR | 2011-0042004 A | 4/2011 |
| TW | 200940554 | 10/2009 |
| WO | WO-03/058667 | 7/2003 |
| WO | WO-2004/043937 | 5/2004 |
| WO | WO-2004/094389 | 11/2004 |
| WO | WO-2005/113531 | 12/2005 |
| WO | WO-2006/115232 | 11/2006 |
| WO | WO-2007/069569 | 6/2007 |
| WO | WO-2007/090773 | 8/2007 |
| WO | WO-2008/023628 | 2/2008 |
| WO | WO-2008/031743 | 3/2008 |
| WO | WO-2008/119666 | 10/2008 |
| WO | WO-2009/100991 | 8/2009 |

OTHER PUBLICATIONS

Goldsmith.C et al., "C—H Bond Activation by a Ferric Methoxide Complex: Modeling the Rate-Determining Step in the Mechanism of Lipoxygenase", J. Am. Chem. Soc. (Journal of the American Chemical Society), 2002, vol. 124, No. 1, pp. 83-96.
Onishi.T et al., "A Method of Measuring an Energy Level", High Molecular El Materials—Development of Light-Emitting High Molecular Compounds, Dec. 25, 2004, pp. 64-67, Kyoritsu Shuppan.
Zhang.M et al., "Highly-efficient solution-processed OLEDs based on new bipolar emitters", Chemical Communications, 2010, vol. 46, pp. 3923-3925.
Wermuth.C, "Molecular Variations Based on Isosteric Replacements", The Practice of Medicinal Chemistry, 1996, pp. 204-237.

(56) References Cited

OTHER PUBLICATIONS

Chinese Office Action (Application No. 201210025092.X) Dated Oct. 28, 2014.

* cited by examiner

HETEROCYCLIC COMPOUND

CROSS-REFERENCE TO RELATED APPLICATIONS

This application is a continuation of U.S. application Ser. No. 13/360,058, filed Jan. 27, 2012, now allowed, which claims the benefit of foreign priority applications filed in Japan as Serial No. 2011-020113 on Feb. 1, 2011, and Serial No. 2011-181467 on Aug. 23, 2011, all of which are incorporated by reference.

BACKGROUND OF THE INVENTION

1. Field of the Invention

The present invention relates to a heterocyclic compound. In particular, the present invention relates to a heterocyclic compound that can be used for a light-emitting element utilizing organic electroluminescence (EL).

2. Description of the Related Art

In recent years, research and development have been extensively conducted on light-emitting elements utilizing EL. In the basic structure of such a light-emitting element, a layer containing a light-emitting substance is interposed between a pair of electrodes. By application of a voltage to this element, light emission from the light-emitting substance can be obtained.

Since such light-emitting elements are of a self-light-emitting type, it is considered that they have advantages over liquid crystal displays that the visibility of pixels is high, backlights are not required, and so on, and therefore the light-emitting elements are suitable as flat panel display elements. The light-emitting elements also have a great advantage that they can be manufactured as thin and lightweight elements. Further, very high-speed response is also one of the features of such elements.

Furthermore, since such light-emitting elements can be formed in a film form, they make it possible to provide planar light emission. Therefore, large-area elements utilizing planar light emission can be easily formed. This feature is difficult to obtain with point light sources typified by incandescent lamps and LEDs or linear light sources typified by fluorescent lamps. Thus, light-emitting elements also have great potential as planar light sources applicable to lighting devices and the like.

Such light-emitting elements utilizing electroluminescence can be broadly classified according to whether the light-emitting substance is an organic compound or an inorganic compound. In the case of an organic EL element in which a layer containing an organic compound used as the light-emitting substance is provided between a pair of electrodes, application of a voltage to the light-emitting element causes electron injection from a cathode and hole injection from an anode into the layer containing the organic compound having a light-emitting property and thus current flows. The injected electrons and holes then lead the organic compound having a light-emitting property to its excited state, so that light emission is obtained from the excited organic compound having a light-emitting property.

The excited state formed by an organic compound can be a singlet excited state or a triplet excited state. Light emission from the singlet excited state (S*) is called fluorescence, and emission from the triplet excited state (T*) is called phosphorescence. In addition, the statistical generation ratio thereof in a light-emitting element is considered as follows: $S^*:T^* = 1:3$.

At room temperature, an observation on a compound that can convert energy of a singlet excited state into light emission (hereinafter, referred to as a fluorescent compound) usually shows only light emission from the singlet excited state (fluorescence) without light emission from the triplet excited state (phosphorescence). Therefore the internal quantum efficiency (the ratio of generated photons to injected carriers) of a light-emitting element using a fluorescent compound is assumed to have a theoretical limit of 25% based on a $S^*$-to-$T^*$ ratio of 1:3.

In contrast, an observation on a compound that can convert energy of a triplet excited state into light emission (hereinafter, called a phosphorescent compound) shows light emission from the triplet excited state (phosphorescence). Further, since intersystem crossing (i.e. transition from a singlet excited state to a triplet excited state) easily occurs in a phosphorescent compound, the internal quantum efficiency can be theoretically increased to 100%. That is, higher emission efficiency can be obtained than using a fluorescent compound. For this reason, light-emitting elements using a phosphorescent compound have been under active development recently in order that highly efficient light-emitting elements can be realized.

When formed using the above-described phosphorescent compound, a light-emitting layer of a light-emitting element is often formed such that the phosphorescent compound is dispersed in a matrix containing another compound in order to suppress concentration quenching or quenching due to triplet-triplet annihilation in the phosphorescent compound. Here, the compound as the matrix is called a host material, and the compound dispersed in the matrix, such as a phosphorescent compound, is called a guest material.

In the case where a phosphorescent compound is a guest material, a host material needs to have higher triplet excitation energy (energy difference between a ground state and a triplet excited state) than the phosphorescent compound.

Furthermore, since singlet excitation energy (energy difference between a ground state and a singlet excited state) is higher than triplet excitation energy, a substance that has high triplet excitation energy also has high singlet excitation energy. Therefore the above substance that has high triplet excitation energy is also effective in a light-emitting element using a fluorescent compound as a light-emitting substance.

Studies have been conducted on compounds having dibenzo[f,h]quinoxaline rings, which are examples of the host material used when a phosphorescent compound is a guest material (e.g. see Patent Documents 1 and 2).

REFERENCES

Patent Document 1: International Publication WO 03/058667 Pamphlet

Patent Document 2: Japanese Published Patent Application No. 2007-189001

SUMMARY OF THE INVENTION

However, the above compounds having dibenzo[f,h]quinoxaline rings have a planar structure, and accordingly, these compounds are easily crystallized. A light-emitting element using a compound that is easy to crystallize has a short lifetime. Further, if another skeleton is directly bonded to the dibenzo[f,h]quinoxaline ring so that the compound has a sterically bulky structure, the conjugated system could possibly extend to cause a decrease in triplet excitation energy.

Further, in order to realize a light-emitting device, an electronic device, and a lighting device each having reduced power consumption and high reliability, a light-emitting element having low driving voltage, a light-emitting element having high current efficiency, or a light-emitting element having a long lifetime have been expected.

Therefore, an object of one embodiment of the present invention is to provide a novel heterocyclic compound which can be used for a light-emitting element, as a host material of a light-emitting layer in which a light-emitting substance is dispersed, in particular, a novel heterocyclic compound which can be suitably used as a host material in which a phosphorescent compound is used as a light-emitting substance.

Another object of one embodiment of the present invention is to provide a light-emitting element having low driving voltage. Yet another object of one embodiment of the present invention is to provide a light-emitting element having high current efficiency. Another object of one embodiment of the present invention is to provide a light-emitting element having a long lifetime. Still another object of one embodiment of the present invention is to provide a light-emitting device, an electronic device, and a lighting device each having reduced power consumption by using the above light-emitting element.

Note that an object of the invention to be disclosed below is to achieve at least one of the above-described objects.

A compound with a quinoxaline skeleton has a high electron-transport property, and the use of such a compound for a light-emitting element enables the element to have low driving voltage. However, a quinoxaline skeleton has a planar structure. Since a compound having a planar structure is easily crystallized when formed into a film, the use of such a compound for light-emitting elements causes the elements to have a short lifetime. Furthermore, a quinoxaline skeleton is poor at accepting holes. When a compound that cannot easily accept holes is used as a host material of a light-emitting layer, the region of electron-hole recombination concentrates on an interface of the light-emitting layer, leading to a reduction in the lifetime of the light-emitting element. It is likely that these problems will be solved by introduction of a hole-transport skeleton into the molecule. However, if a hole-transport skeleton is directly bonded to a quinoxaline skeleton, the conjugated system extends to cause a decrease in band gap and a decrease in triplet excitation energy.

Nevertheless, the present inventors have found that the above problems can be solved by using, for a light-emitting element, a compound in which a dibenzo[f,h]quinoxaline ring and a hole-transport skeleton are bonded through an arylene group.

As the compound in which a dibenzo[f,h]quinoxaline ring and a hole-transport skeleton are bonded through an arylene group, a heterocyclic compound below can be given.

One embodiment of the present invention is a heterocyclic compound represented by a general formula (G1) below.

[Chemical Formula 1]

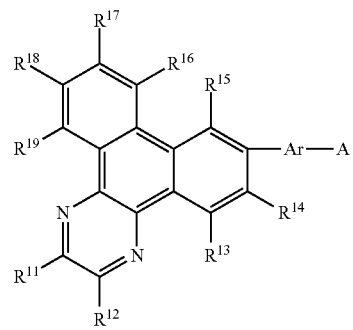

(G1)

In the formula, A represents any of a substituted or unsubstituted dibenzothiophenyl group, a substituted or unsubstituted dibenzofuranyl group, and a substituted or unsubstituted carbazolyl group, $R^{11}$ to $R^{19}$ separately represent any of hydrogen, an alkyl group having 1 to 4 carbon atoms, and a substituted or unsubstituted aryl group having 6 to 13 carbon atoms, and Ar represents a substituted or unsubstituted arylene group having 6 to 13 carbon atoms.

Another embodiment of the present invention is a heterocyclic compound represented by a general formula (G2-1) below.

[Chemical Formula 2]

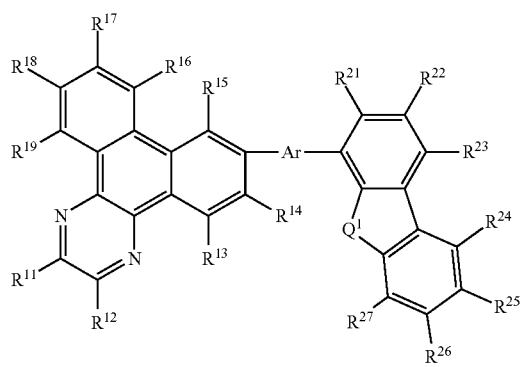

(G2-1)

In the formula, $Q^1$ represents any of a sulfur atom, an oxygen atom, and a nitrogen atom, and the nitrogen atom has an alkyl group having 1 to 4 carbon atoms or a substituted or unsubstituted aryl group having 6 to 13 carbon atoms as a substituent. $R^{11}$ to $R^{19}$ and $R^{21}$ to $R^{27}$ separately represent any of hydrogen, an alkyl group having 1 to 4 carbon atoms, and a substituted or unsubstituted aryl group having 6 to 13 carbon atoms, and Ar represents a substituted or unsubstituted arylene group having 6 to 13 carbon atoms.

Another embodiment of the present invention is a heterocyclic compound represented by a general formula (G2-2) below.

[Chemical Formula 3]

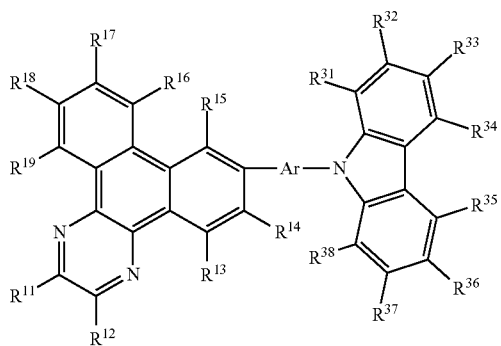

(G2-2)

In the formula, $R^{11}$ to $R^{19}$ and $R^{31}$ to $R^{38}$ separately represent any of hydrogen, an alkyl group having 1 to 4 carbon atoms, a substituted or unsubstituted aryl group having 6 to 13 carbon atoms, and Ar represents a substituted or unsubstituted arylene group having 6 to 13 carbon atoms.

Another embodiment of the present invention is a heterocyclic compound represented by a general formula (G2-3) below.

[Chemical Formula 4]

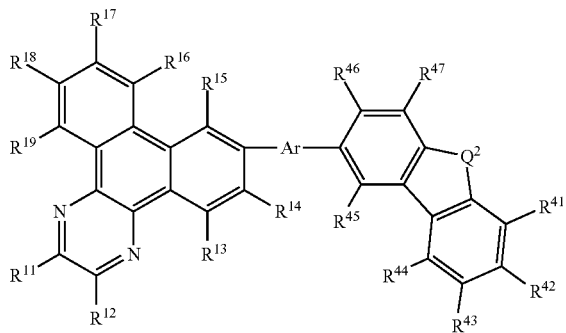

(G2-3)

In the formula, $R^{11}$ to $R^{19}$ and $R^{41}$ to $R^{47}$ separately represent any of hydrogen, an alkyl group having 1 to 4 carbon atoms, and a substituted or unsubstituted aryl group having 6 to 13 carbon atoms, Ar represents a substituted or unsubstituted arylene group having 6 to 13 carbon atoms, $Q^2$ represents any of a sulfur atom, an oxygen atom, and a nitrogen atom, and the nitrogen atom has an alkyl group having 1 to 4 carbon atoms or a substituted or unsubstituted aryl group having 6 to 13 carbon atoms as a substituent.

In the general formulae (G1) and (G2-1) to (G2-3), Ar is preferably a substituted or unsubstituted phenylene group or a substituted or unsubstituted biphenyldiyl group, particularly a substituted or unsubstituted phenylene group. Furthermore, Ar is much preferably a substituted or unsubstituted m-phenylene group so as to have a high level of triplet excitation energy (T1 level).

Another embodiment of the present invention is a heterocyclic compound represented by a general formula (G3-1) below.

[Chemical Formula 5]

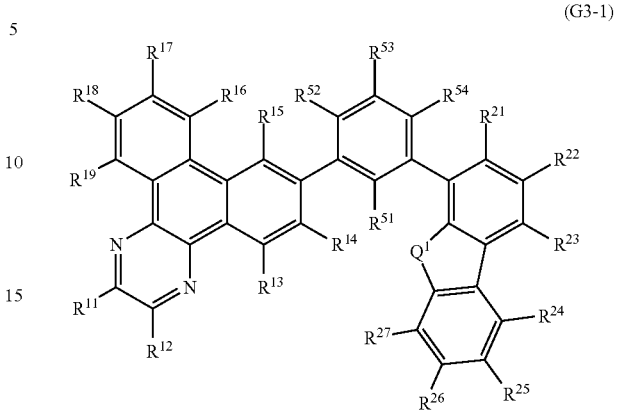

(G3-1)

In the formula, $Q^1$ represents any of a sulfur atom, an oxygen atom, and a nitrogen atom, and the nitrogen atom has an alkyl group having 1 to 4 carbon atoms or a substituted or unsubstituted aryl group having 6 to 13 carbon atoms as a substituent. In addition, $R^{11}$ to $R^{19}$, $R^{21}$ to $R^{27}$, and $R^{51}$ to $R^{54}$ separately represent any of hydrogen, an alkyl group having 1 to 4 carbon atoms, and a substituted or unsubstituted aryl group having 6 to 13 carbon atoms.

Yet another embodiment of the present invention is a heterocyclic compound represented by a general formula (G3-2) below.

[Chemical Formula 6]

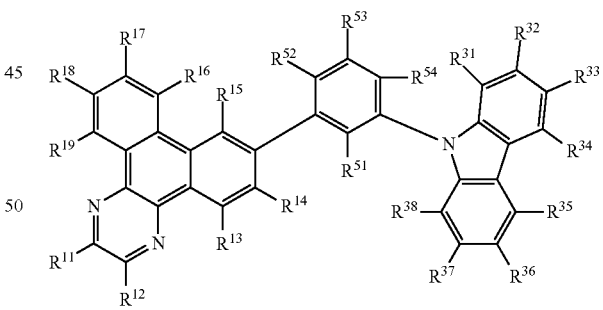

(G3-2)

In the formula, $R^{11}$ to $R^{19}$, $R^{31}$ to $R^{38}$, and $R^{51}$ to $R^{54}$ separately represent any of hydrogen, an alkyl group having 1 to 4 carbon atoms, and a substituted or unsubstituted aryl group having 6 to 13 carbon atoms.

Yet another embodiment of the present invention is a heterocyclic compound represented by a general formula (G3-3) below.

[Chemical Formula 7]

(G3-3)

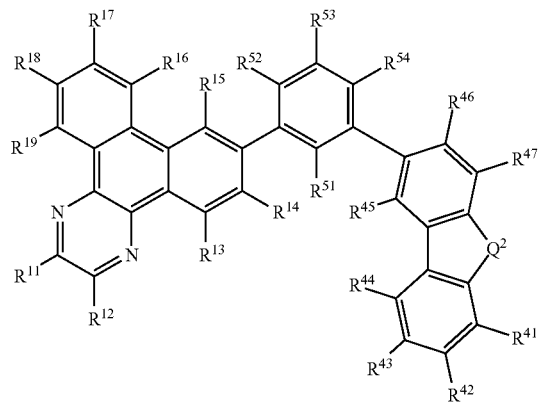

In the formula, $R^{11}$ to $R^{19}$, $R^{41}$ to $R^{47}$, and $R^{51}$ to $R^{54}$ separately represent any of hydrogen, an alkyl group having 1 to 4 carbon atoms, and a substituted or unsubstituted aryl group having 6 to 13 carbon atoms, $Q^2$ represents any of a sulfur atom, an oxygen atom, and a nitrogen atom, and the nitrogen atom has an alkyl group having 1 to 4 carbon atoms or a substituted or unsubstituted aryl group having 6 to 13 carbon atoms as a substituent.

The introduction of a hole-transport skeleton into a dibenzo[f,h]quinoxaline ring enables any of the compounds according to one embodiment of the present invention to have a sterically bulky structure, and the compound is difficult to crystallize when a film is formed using the compound. By use of the compound for a light-emitting element, the element can have a long lifetime. Moreover, in this compound, since a dibenzo[f,h]quinoxaline ring and a hole-transport skeleton are bonded through an arylene group, decreases in band gap and triplet excitation energy can be prevented as compared with a compound in which a dibenzo[f,h]quinoxaline ring and a hole-transport skeleton are directly bonded. By use of the compound for a light-emitting element, the element can have high current efficiency.

Thus, any of the compounds according to one embodiment of the present invention can be suitably used as a material for an organic device such as a light-emitting element or an organic transistor.

One embodiment of the present invention is a light-emitting element including the above-described heterocyclic compound.

One embodiment of the present invention is a light-emitting element which includes a light-emitting layer between a pair of electrodes. The light-emitting layer includes a light-emitting substance and the above-described heterocyclic compound.

By use of any of the heterocyclic compounds according to one embodiment of the present invention, a light-emitting element can have low driving voltage. Further, by use of any of the heterocyclic compounds according to one embodiment of the present invention, a light-emitting element can have high current efficiency. In addition, by use of any of the heterocyclic compounds according to one embodiment of the present invention, a light-emitting element can have a long lifetime. Low power consumption can be realized in a light-emitting device (such as an image display device) which includes the above light-emitting element. Thus, one embodiment of the present invention is a light-emitting device including the above light-emitting element. One embodiment of the present invention also includes an electronic device using the light-emitting device in its display portion and a lighting device using the light-emitting device in its light-emitting portion.

The light-emitting device in this specification covers an image display device using a light-emitting element and also the following devices: a module including a light-emitting element to which a connector such as an anisotropic conductive film, a TAB (tape automated bonding) tape, or a TCP (tape carrier package) is attached; a module in which the top of a TAB tape or a TCP is provided with a printed wiring board; a module in which an IC (integrated circuit) is directly mounted on a light-emitting element by a COG (chip on glass) technique; and further a light-emitting device used for a lighting device and the like.

One embodiment of the present invention can provide a novel heterocyclic compound which can be used for a light-emitting element, as a host material of a light-emitting layer in which a light-emitting substance is dispersed. Another embodiment of the present invention can provide a light-emitting element having low driving voltage. Yet another embodiment of the present invention can provide a light-emitting element having high current efficiency. Still another embodiment of the present invention can provide a light-emitting element having a long lifetime. By use of the light-emitting element, another embodiment of the present invention can provide a light-emitting device, an electronic device, and a lighting device each having reduced power consumption.

DETAILED DESCRIPTION OF THE INVENTION

Figure 1A:
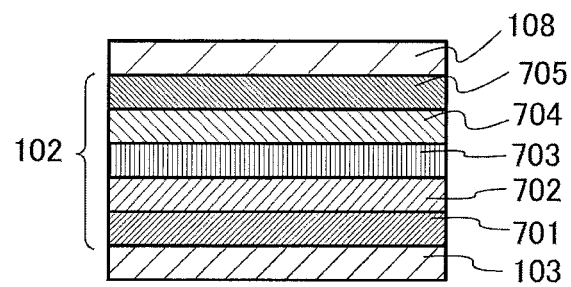
FIGS. 1A to 1C each illustrate a light-emitting element according to one embodiment of the present invention.

Embodiments of the present invention will now be described in detail with reference to the accompanying drawings. Note that the invention is not limited to the description given below, and it will be easily understood by those skilled in the art that various changes and modifications can be made without departing from the spirit and scope of the invention. Therefore, the invention should not be construed as being limited to the description in the following embodiments.

Embodiment 1

In Embodiment 1, heterocyclic compounds according to one embodiment of the present invention will be described.

One embodiment of the present invention is the heterocyclic compound represented by the general formula (G1).

[Chemical Formula 8]

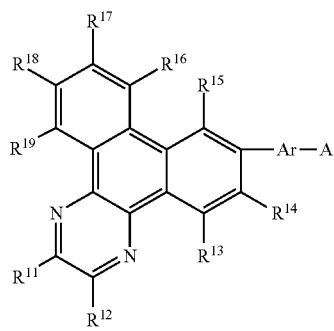

(G1)

In the general formula (G1), A represents any of a substituted or unsubstituted dibenzothiophenyl group, a substituted or unsubstituted dibenzofuranyl group, and a substituted or unsubstituted carbazolyl group, $R^{11}$ to $R^{19}$ separately represent any of hydrogen, an alkyl group having 1 to 4 carbon atoms, and a substituted or unsubstituted aryl group having 6 to 13 carbon atoms, and Ar represents a substituted or unsubstituted arylene group having 6 to 13 carbon atoms.

Another embodiment of the present invention is a heterocyclic compound represented by the general formula (G2-1) below.

[Chemical Formula 9]

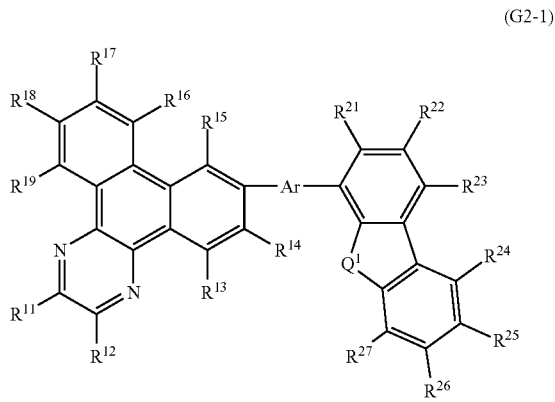

(G2-1)

In the general formula (G2-1), $Q^1$ represents any of a sulfur atom, an oxygen atom, and a nitrogen atom, and the nitrogen atom has an alkyl group having 1 to 4 carbon atoms or a substituted or unsubstituted aryl group having 6 to 13 carbon atoms as a substituent. In addition, $R^{11}$ to $R^{19}$ and $R^{21}$ to $R^{27}$ separately represent any of hydrogen, an alkyl group having 1 to 4 carbon atoms, and a substituted or unsubstituted aryl group having 6 to 13 carbon atoms, and Ar represents a substituted or unsubstituted arylene group having 6 to 13 carbon atoms.

Another embodiment of the present invention is a heterocyclic compound represented by the general formula (G2-2) below.

[Chemical Formula 10]

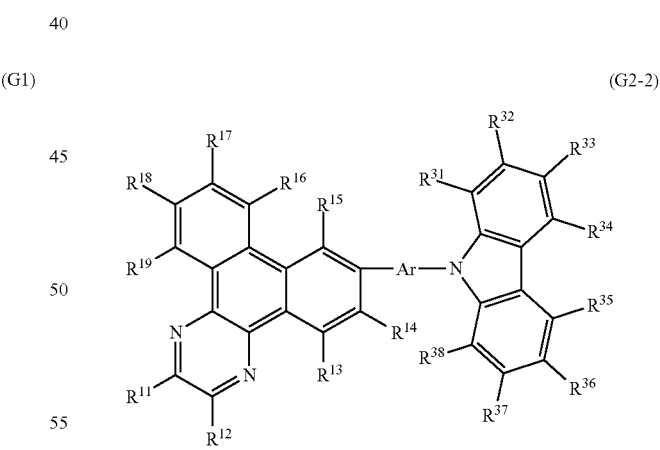

(G2-2)

In the general formula (G2-2), $R^{11}$ to $R^{19}$ and $R^{31}$ to $R^{38}$ separately represent any of hydrogen, an alkyl group having 1 to 4 carbon atoms, and a substituted or unsubstituted aryl group having 6 to 13 carbon atoms, and Ar represents a substituted or unsubstituted arylene group having 6 to 13 carbon atoms.

Another embodiment of the present invention is a heterocyclic compound represented by the general formula (G2-3) below.

[Chemical Formula 11]

(G2-3)

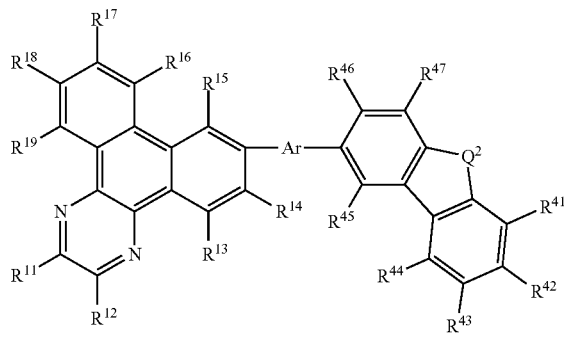

In the general formula (G2-3), $R^{11}$ to $R^{19}$ and $R^{41}$ to $R^{47}$ separately represent any of hydrogen, an alkyl group having 1 to 4 carbon atoms, and a substituted or unsubstituted aryl group having 6 to 13 carbon atoms, Ar represents a substituted or unsubstituted arylene group having 6 to 13 carbon atoms, $Q^2$ represents any of a sulfur atom, an oxygen atom, and a nitrogen atom, and the nitrogen atom has an alkyl group having 1 to 4 carbon atoms or a substituted or unsubstituted aryl group having 6 to 13 carbon atoms as a substituent.

In the general formulae (G1) and (G2-1) to (G2-3), Ar is preferably a substituted or unsubstituted phenylene group or a substituted or unsubstituted biphenyldiyl group, particularly a substituted or unsubstituted phenylene group. Furthermore, Ar is much preferably a substituted or unsubstituted m-phenylene group so as to have a high T1 level.

Another embodiment of the present invention is a heterocyclic compound represented by the general formula (G3-1) below.

[Chemical Formula 12]

(G3-1)

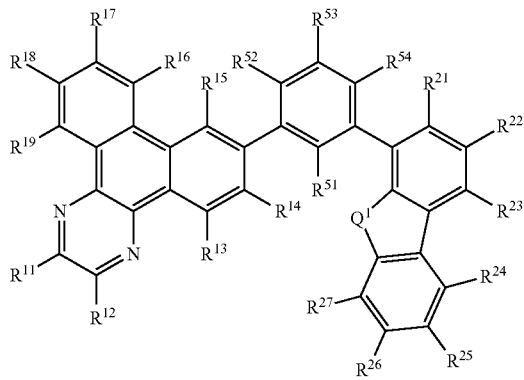

In the general formula (G3-1), $Q^1$ represents any of a sulfur atom, an oxygen atom, and a nitrogen atom, and the nitrogen atom has an alkyl group having 1 to 4 carbon atoms or a substituted or unsubstituted aryl group having 6 to 13 carbon atoms as a substituent. In addition, $R^{11}$ to $R^{19}$, $R^{21}$ to $R^{27}$, and $R^{51}$ to $R^{54}$ separately represent any of hydrogen, an alkyl group having 1 to 4 carbon atoms, and a substituted or unsubstituted aryl group having 6 to 13 carbon atoms.

Yet another embodiment of the present invention is the heterocyclic compound represented by the general formula (G3-2) below.

[Chemical Formula 13]

(G3-2)

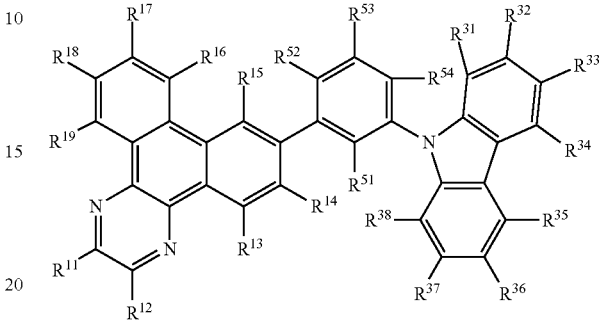

In the general formula (G3-2), $R^{11}$ to $R^{19}$, $R^{31}$ to $R^{38}$, and $R^{51}$ to $R^{54}$ separately represent any of hydrogen, an alkyl group having 1 to 4 carbon atoms, and a substituted or unsubstituted aryl group having 6 to 13 carbon atoms.

Yet another embodiment of the present invention is the heterocyclic compound represented by the general formula (G3-3) below.

[Chemical Formula 14]

(G3-3)

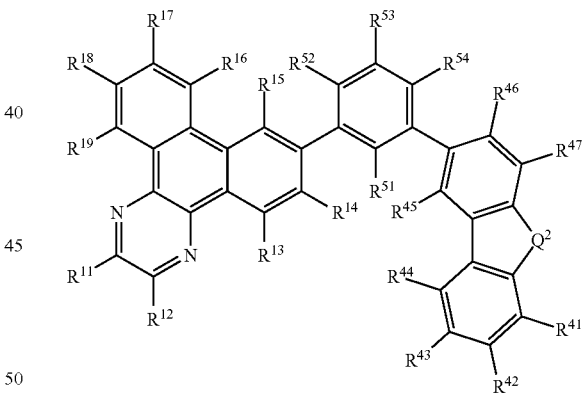

In the general formula (G3-3), $R^{11}$ to $R^{19}$, $R^{41}$ to $R^{47}$, and $R^{51}$ to $R^{54}$ separately represent any of hydrogen, an alkyl group having 1 to 4 carbon atoms, and a substituted or unsubstituted aryl group having 6 to 13 carbon atoms, $Q^2$ represents any of a sulfur atom, an oxygen atom, and a nitrogen atom, and the nitrogen atom has an alkyl group having 1 to 4 carbon atoms or a substituted or unsubstituted aryl group having 6 to 13 carbon atoms as a substituent.

Examples of the specific structures of Ar in the general formulae (G1), (G2-1), (G2-2), and (G2-3) include substituents represented by structural formulae (1-1) to (1-15). Note that Ar having the structure represented by the structural formulae (1-1) to (1-15) may further have an alkyl group having 1 to 4 carbon atoms as a substituent.

[Chemical Formula 15]
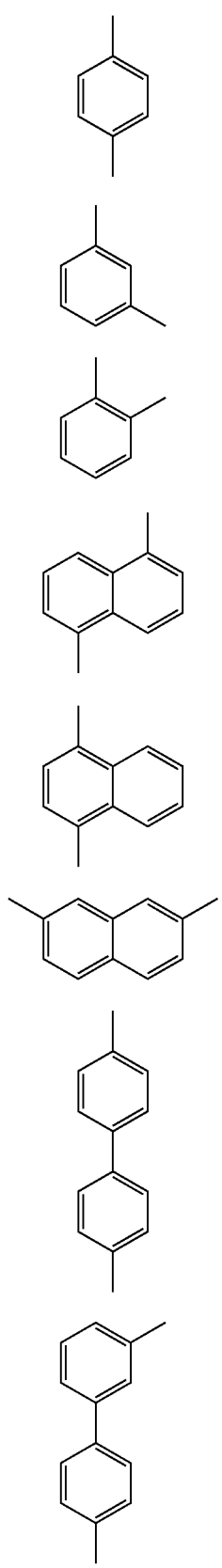
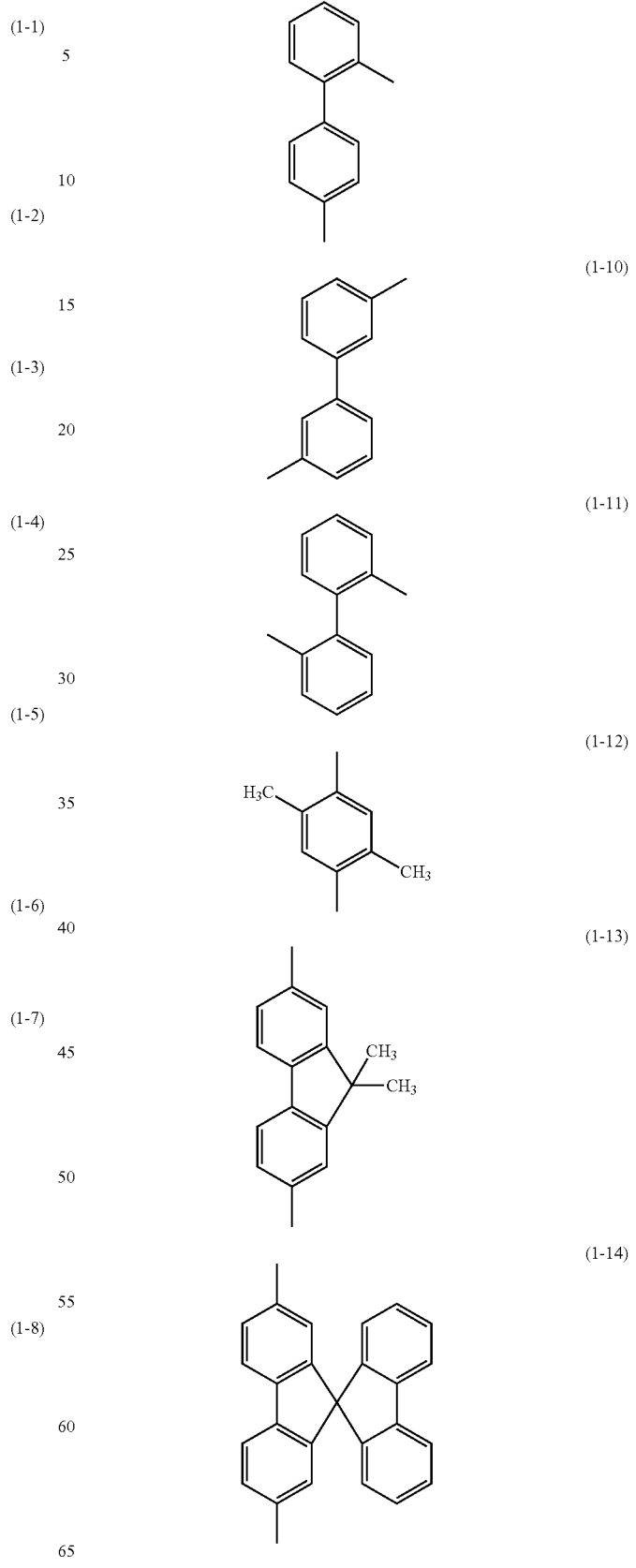

-continued

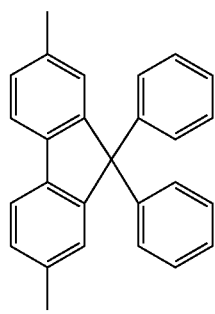
(1-15)

Examples of the specific structures of $R^{11}$ to $R^{19}$, $R^{21}$ to $R^{27}$, $R^{31}$ to $R^{38}$, $R^{41}$ to $R^{47}$, and $R^{51}$ to $R^{54}$ in the general formulae (G1), (G2-1), (G2-2), (G2-3), (G3-1), (G3-2), and (G3-3) include substituents represented by structural formulae (2-1) to (2-23). Further, when $Q^2$ is a nitrogen atom in the general formulae (G2-3) and (G3-3), the substituents represented by the structural formulae (2-1) to (2-23) are also examples of the substituent of the nitrogen atom. Note that the structure represented by the structural formulae (2-10) to (2-20) may further have an alkyl group having 1 to 4 carbon atoms as a substituent.

[Chemical Formula 16]

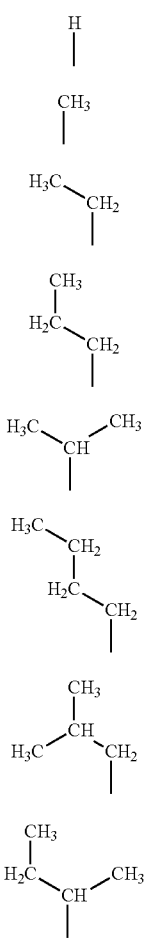

(2-1)
(2-2)
(2-3)
(2-4)
(2-5)
(2-6)
(2-7)
(2-8)

-continued

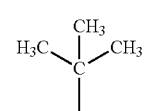
(2-9)

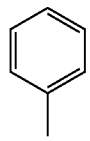
(2-10)

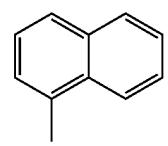
(2-11)

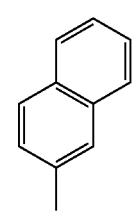
(2-12)

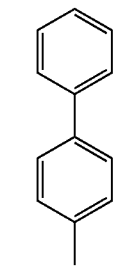
(2-13)

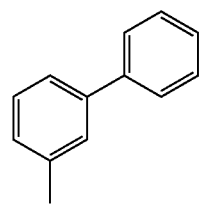
(2-14)

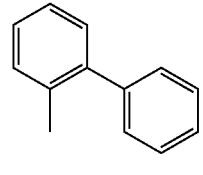
(2-15)

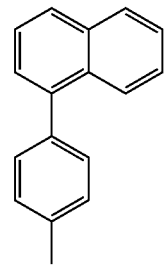
(2-16)

(2-17) 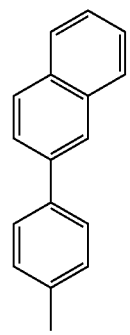
(2-18) 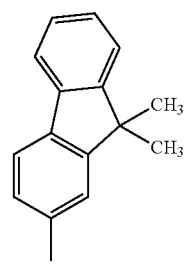
(2-19) 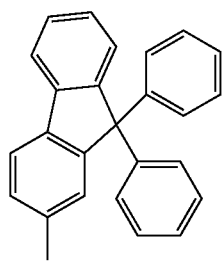
(2-20) 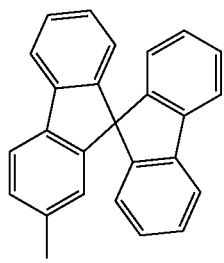
(2-21) 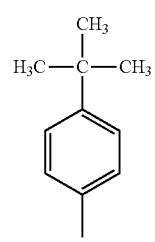
(2-22) 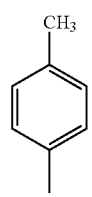
(2-23) 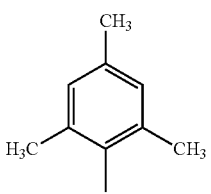
Specific examples of the heterocyclic compound represented by the general formula (G1) are, but not limited to, heterocyclic compounds represented by structural formulae (100) to (146), (200) to (246), (300) to (346), (400) to (459), (500) to (546), and (600) to (646).
[Chemical Formula 17]
(100) 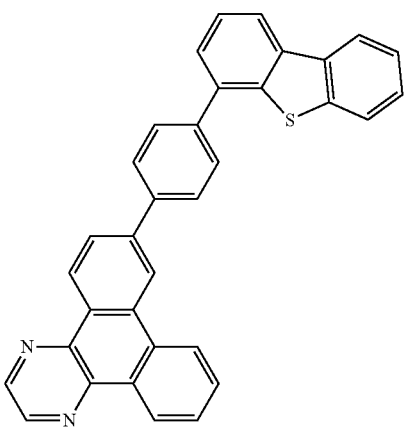
(101) 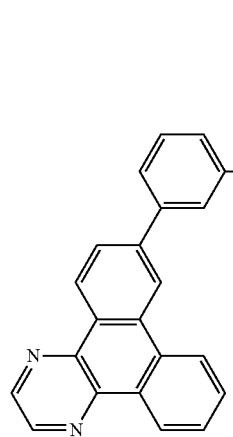

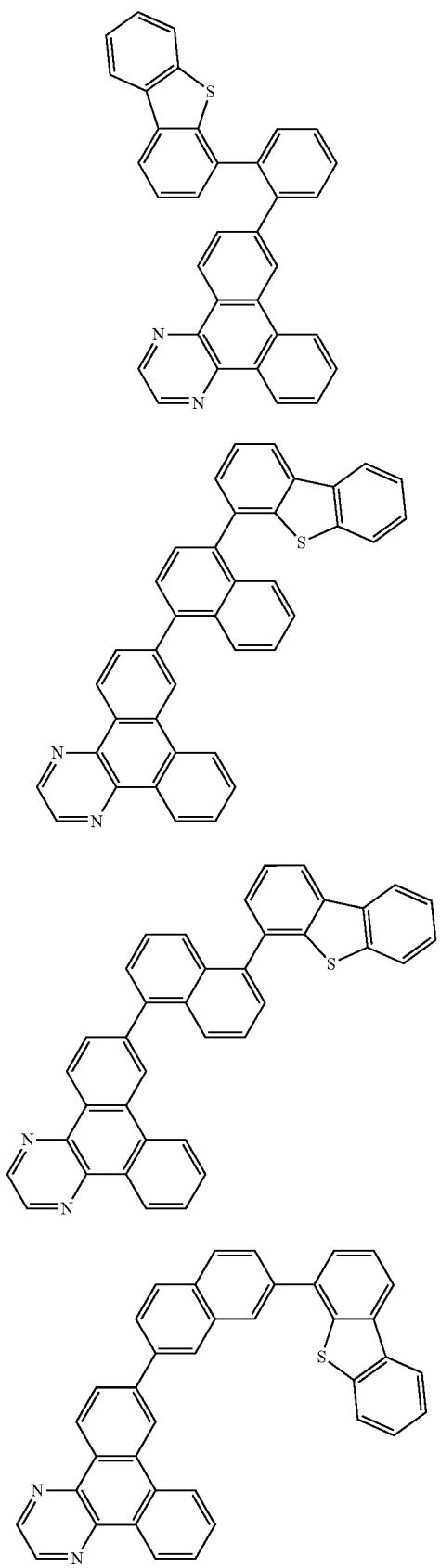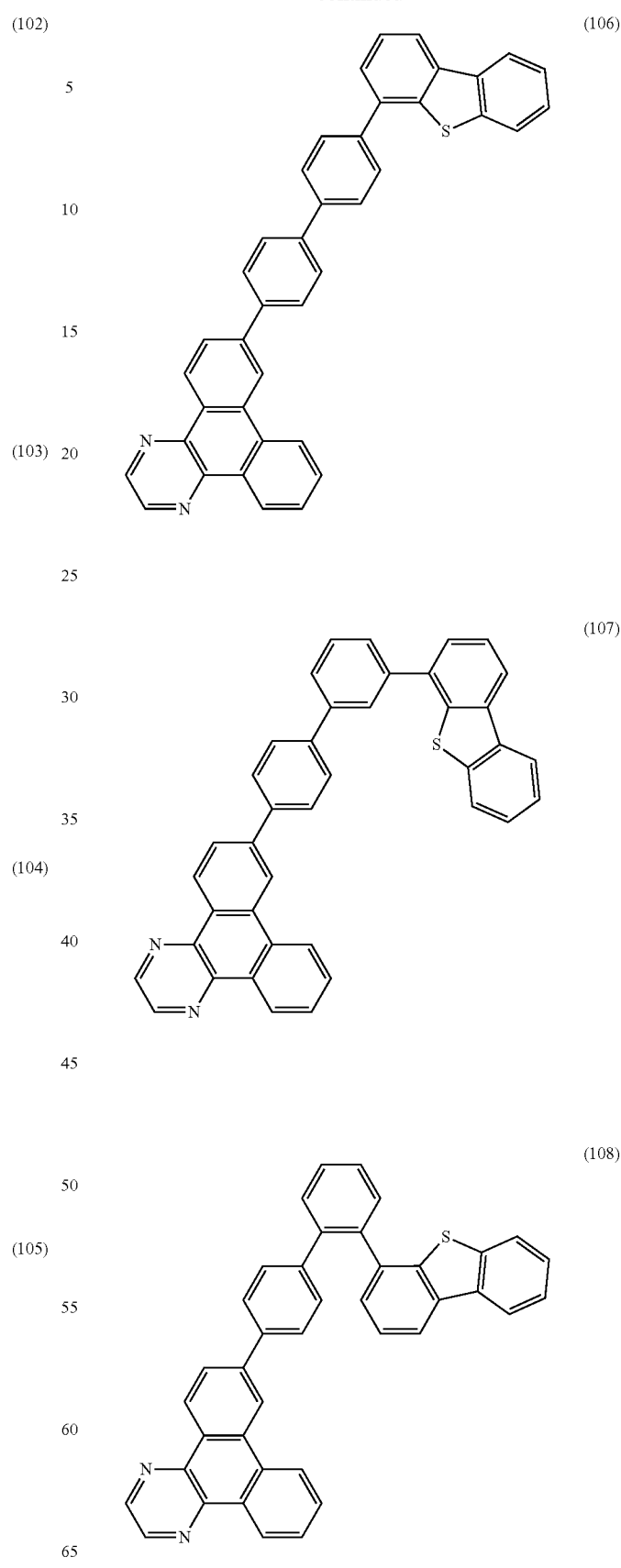

[Chemical Fomula 18]
(109)
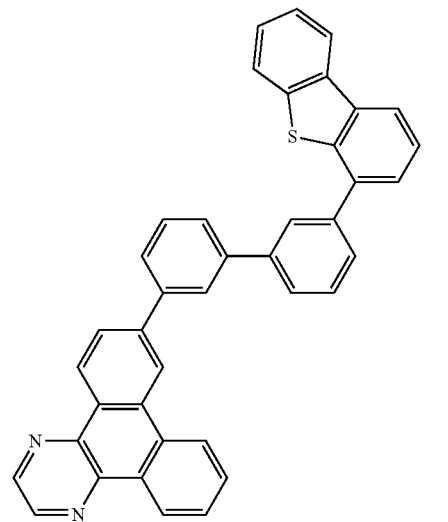
(110)
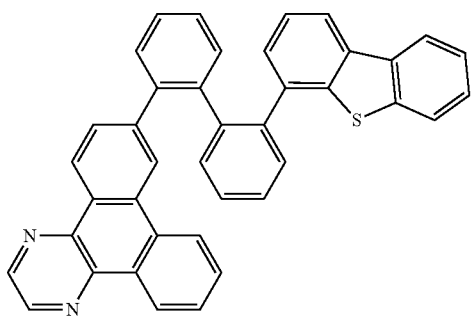
(111)
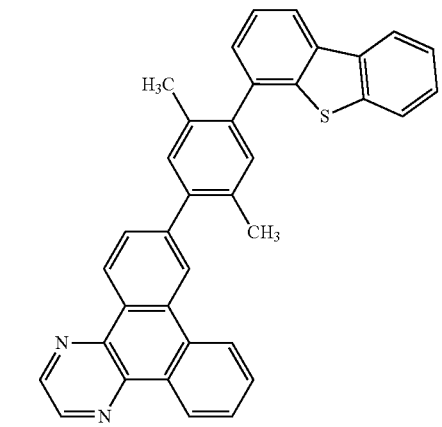
(112)
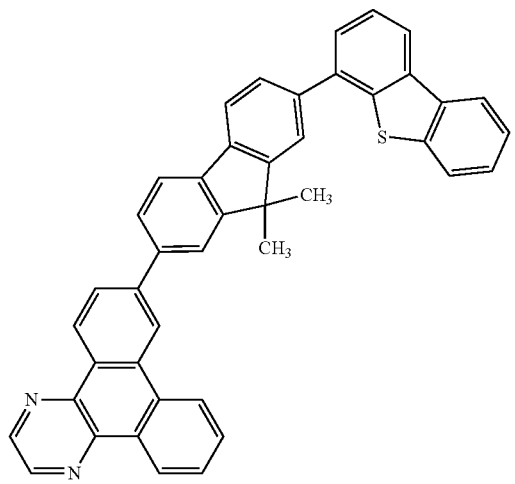
(113)
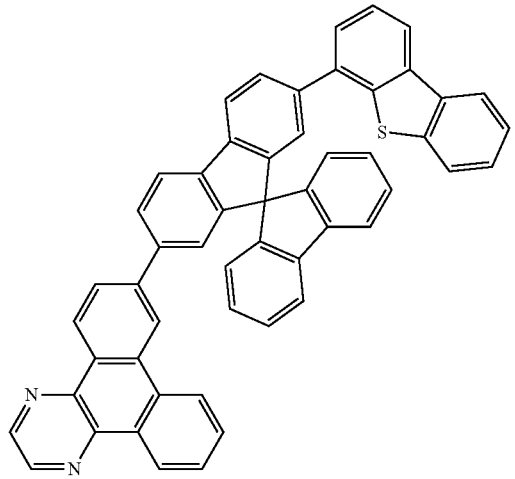
(114)

[Chemical Formula 19]
(115)
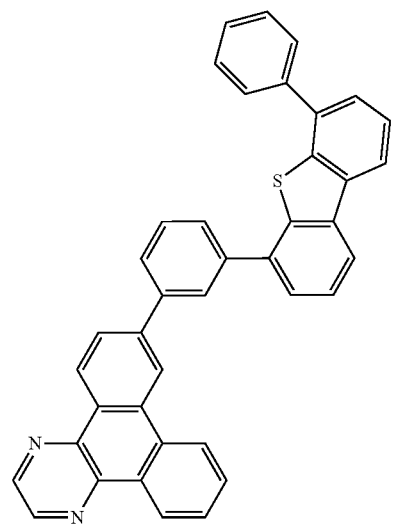
(116)
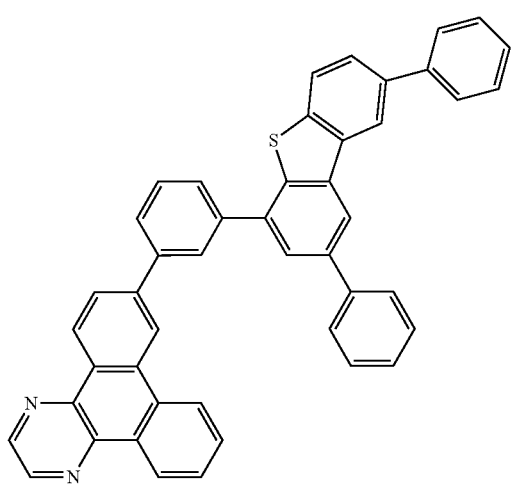
(117)
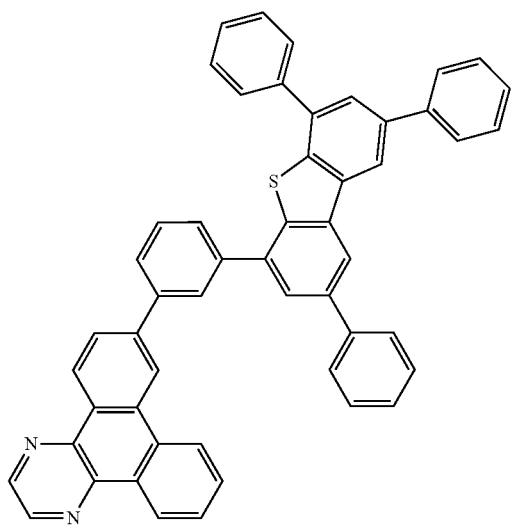
(118)
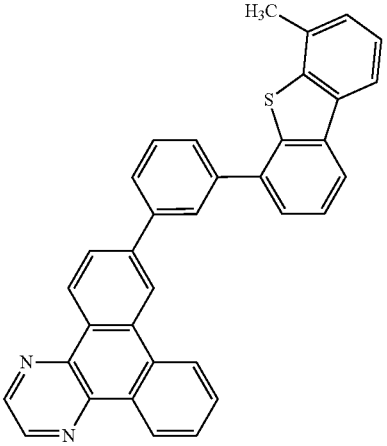
(119)
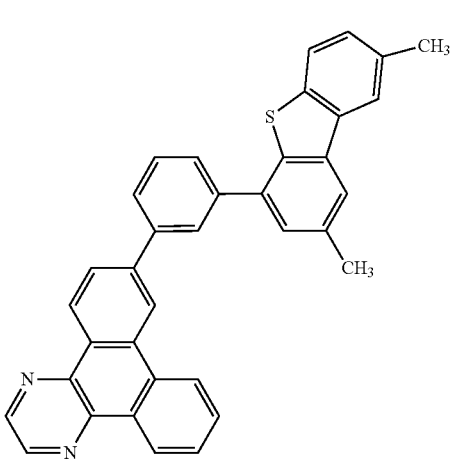
(120)
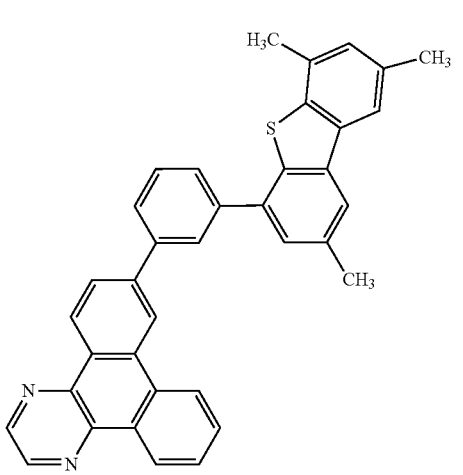

(121)
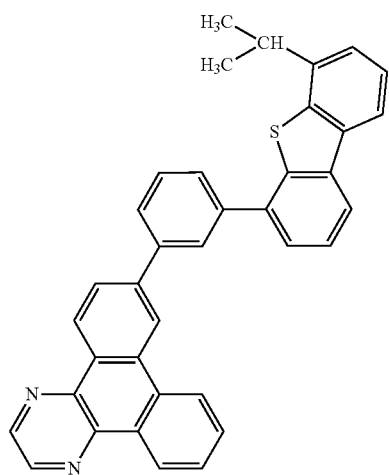
(122)
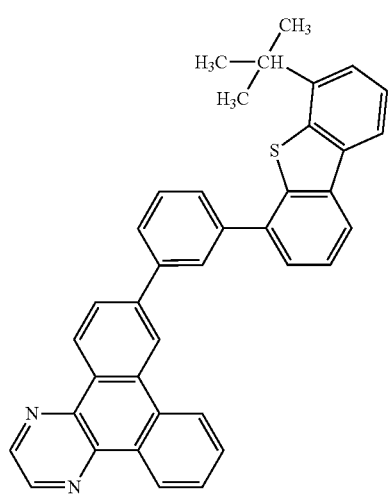
(123)
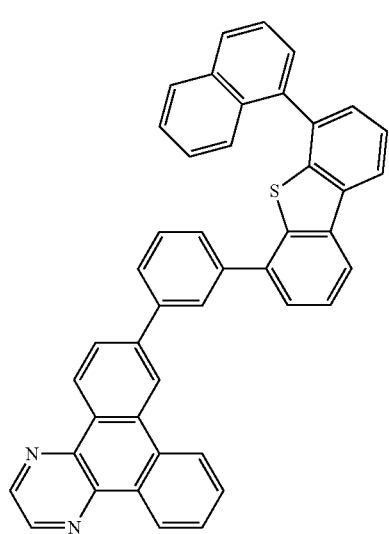
[Chemical Formula 20]
(124)
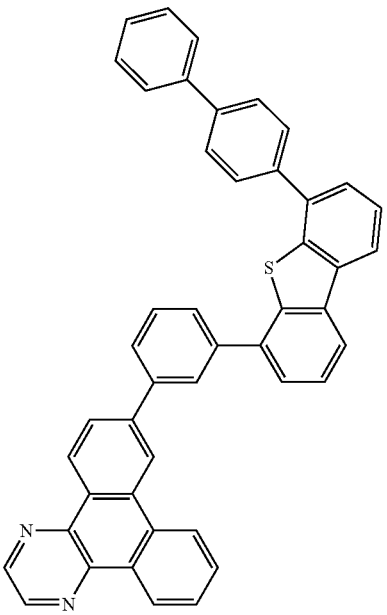
(125)
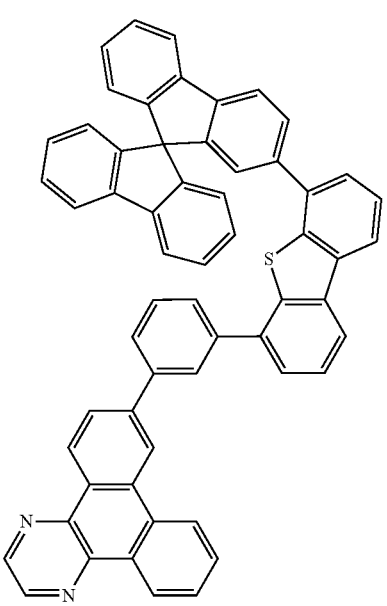

(126)
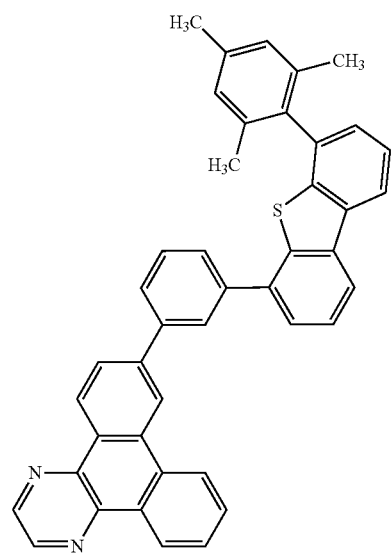
(127)
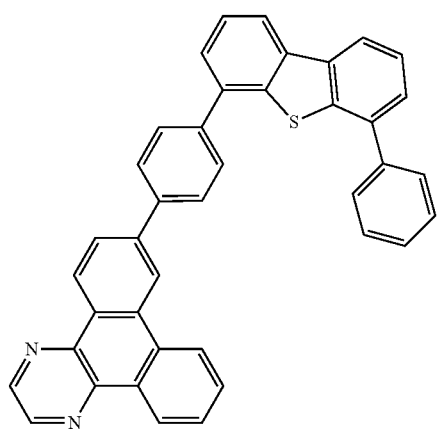
(128)
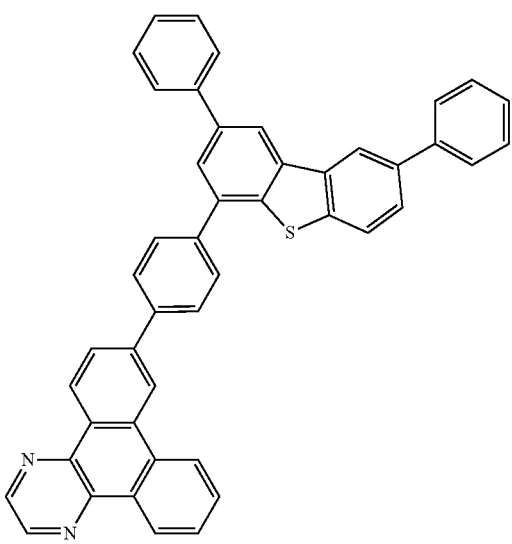
(129)
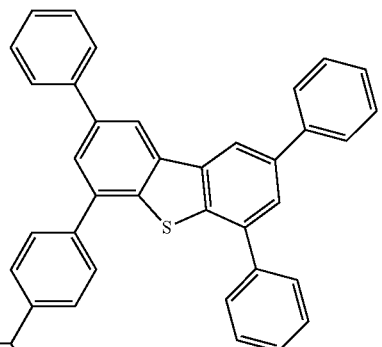
(130)
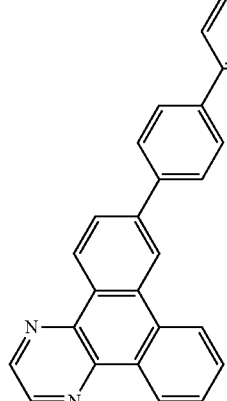
(131)
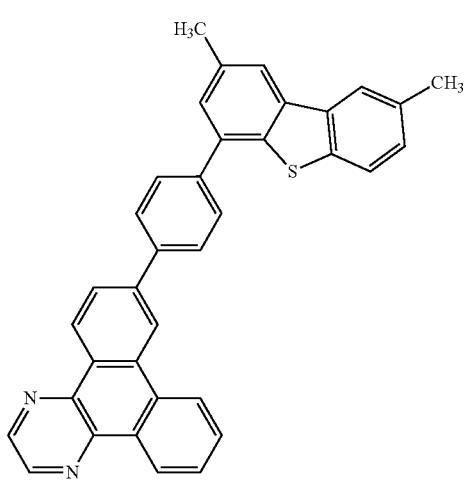

-continued
(132)
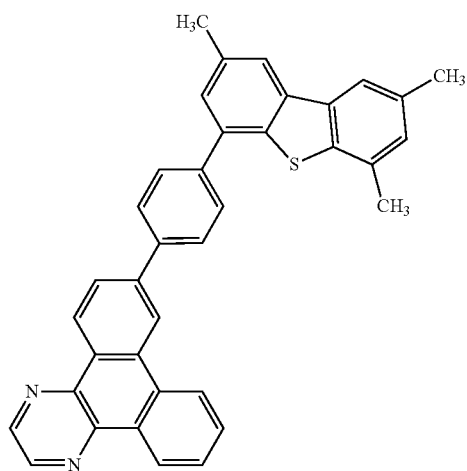
[Chemical Formula 21]
(133)
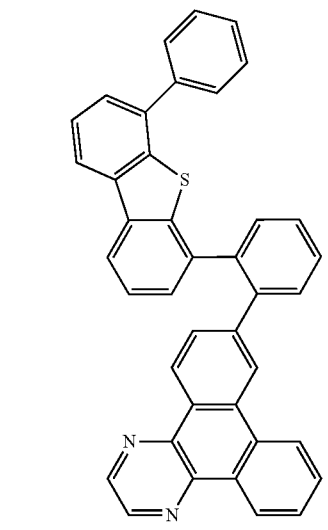
(134)
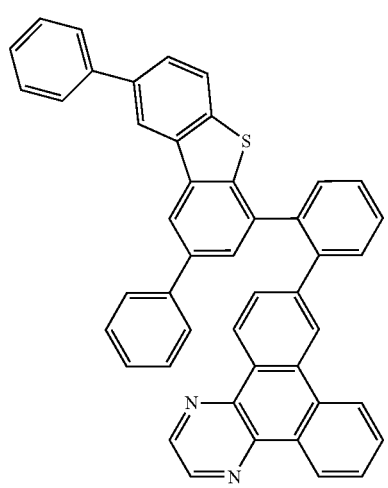
(135)
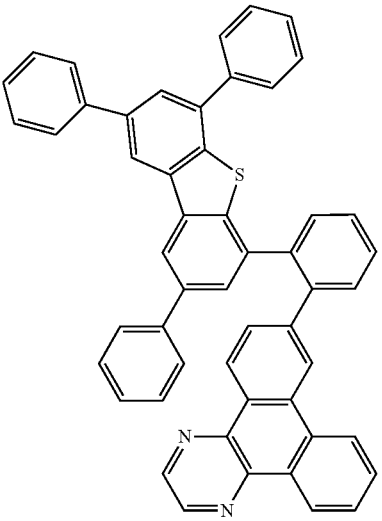
(136)
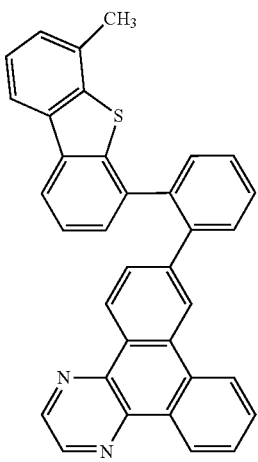
(137)
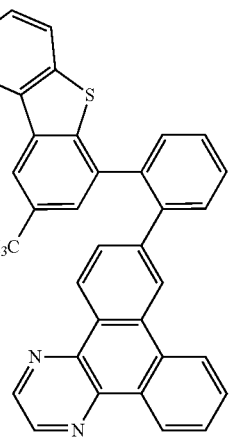

(138)
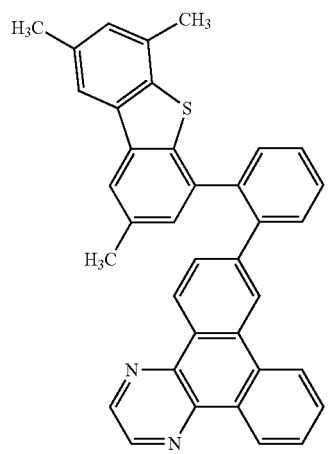
(139)
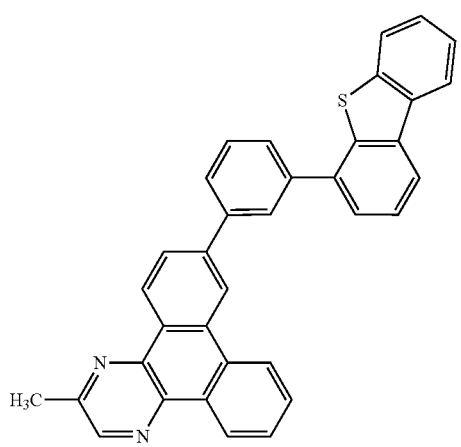
(140)
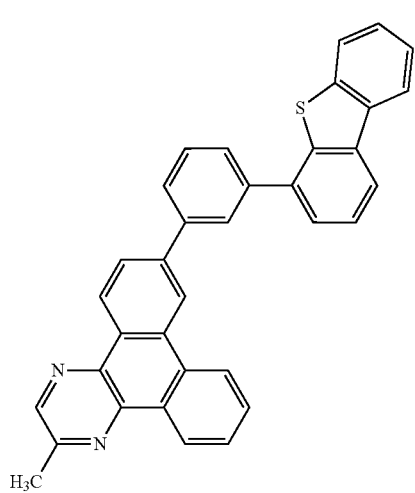
[Chemical Formula 22]
(141)
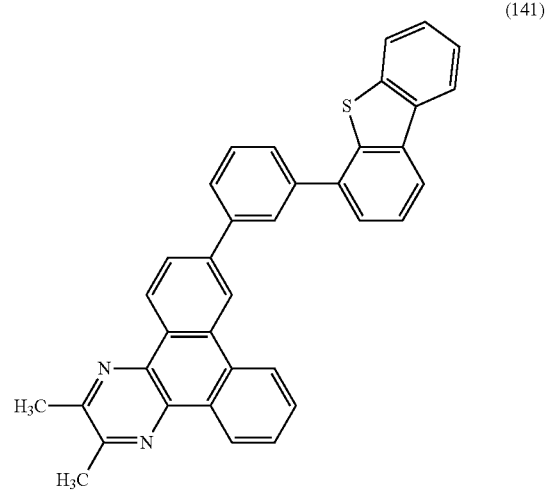
(142)
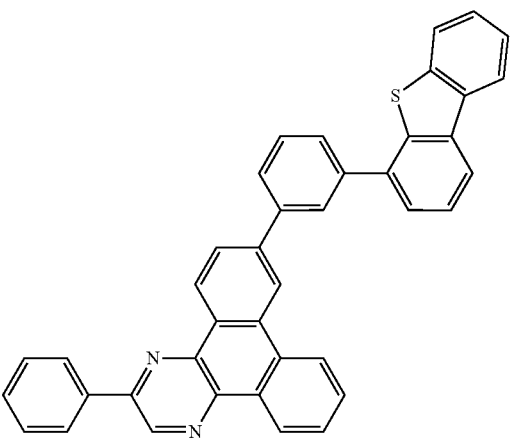
(143)
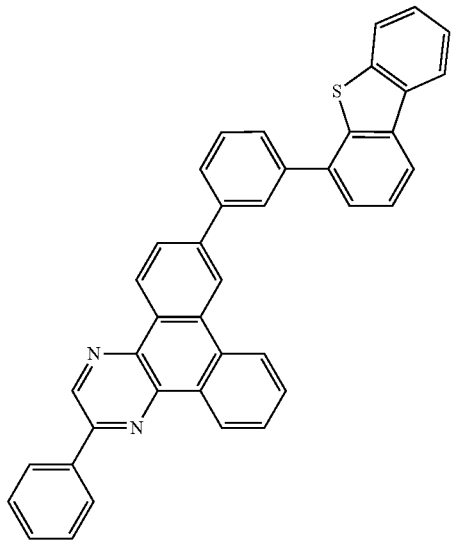

[Chemical Formula 23]
(144)
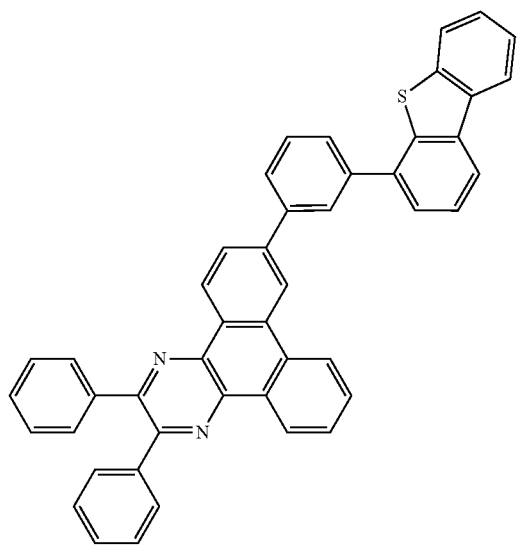
(145)
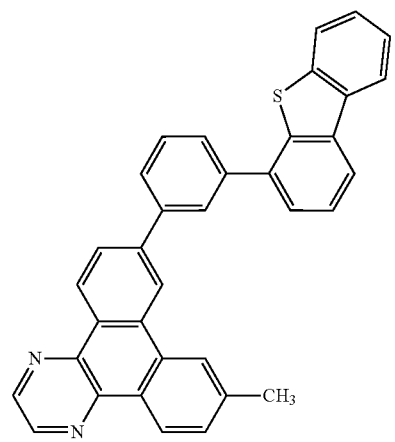
(146)
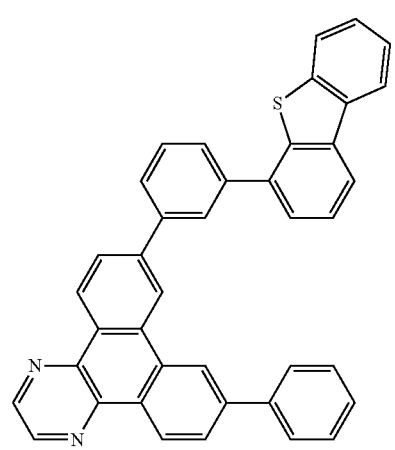
(200)
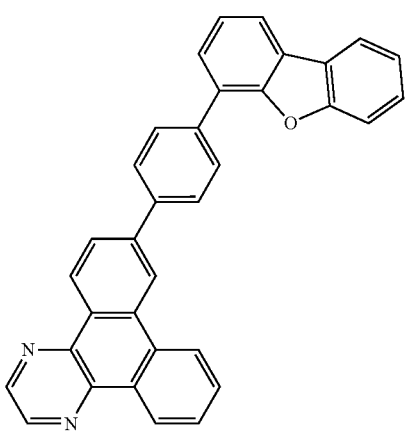
(201)
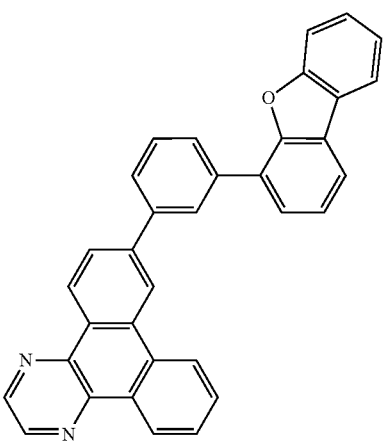
(202)
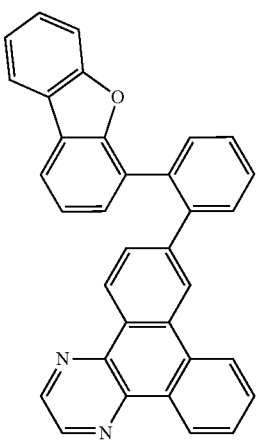

(203)
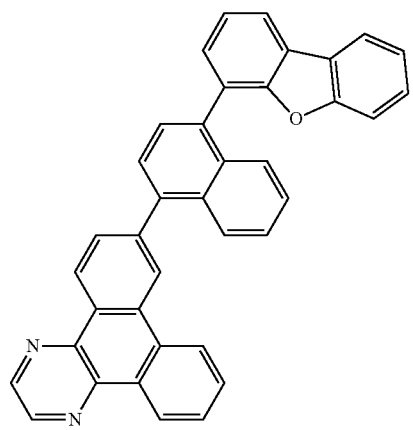
(204)
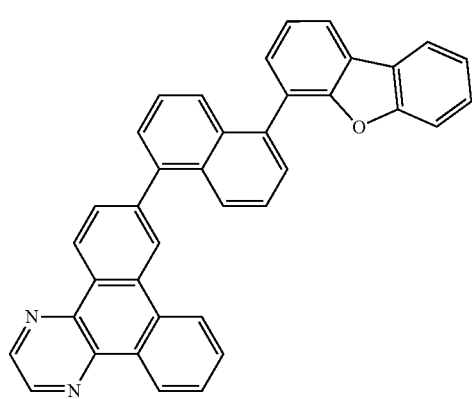
(205)
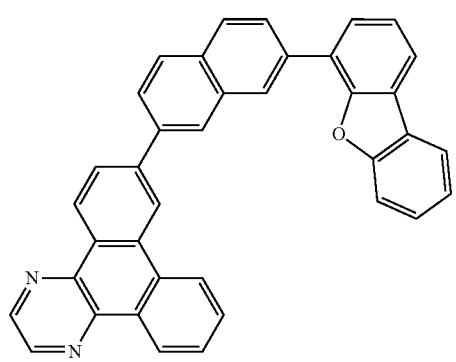
(206)
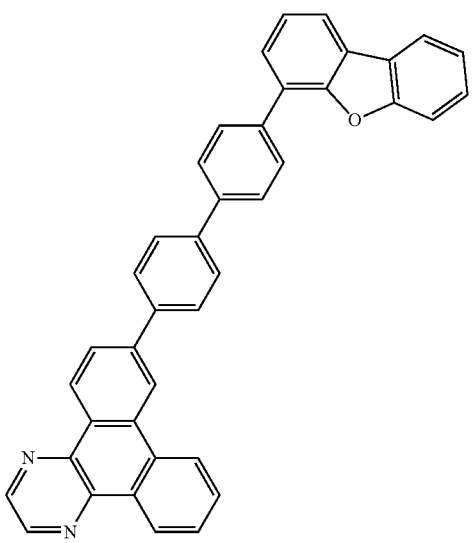
(207)
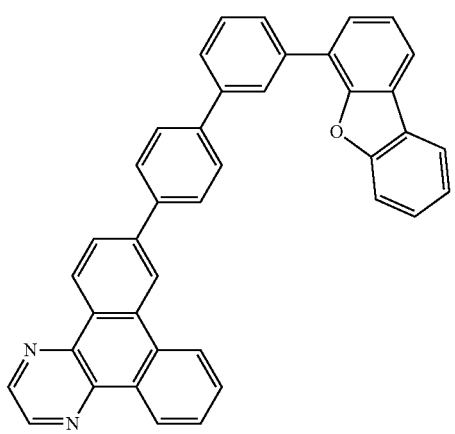
(208)
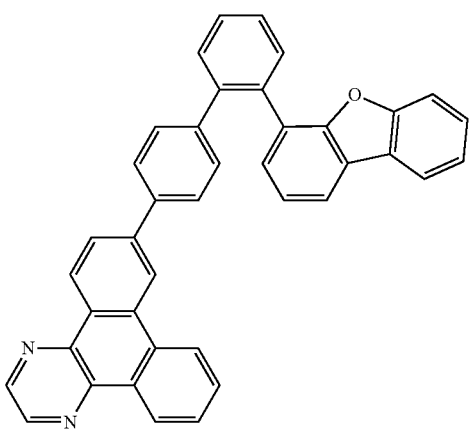

[Chemical Formula 24]
(209)
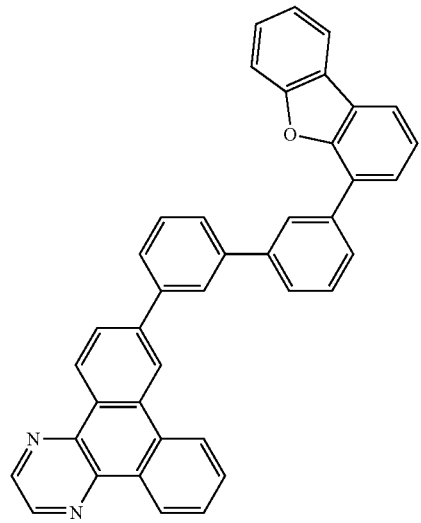
(210)
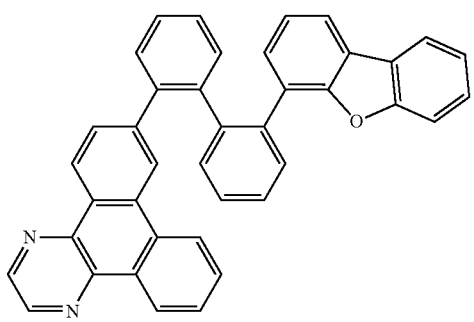
(211)
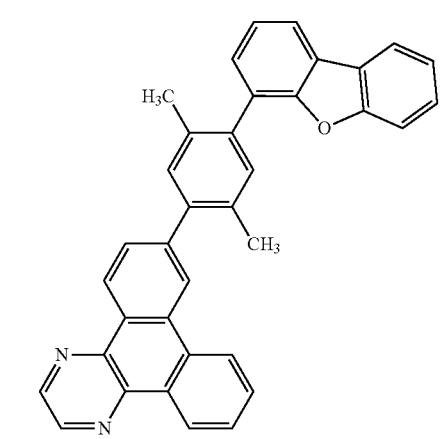
(212)
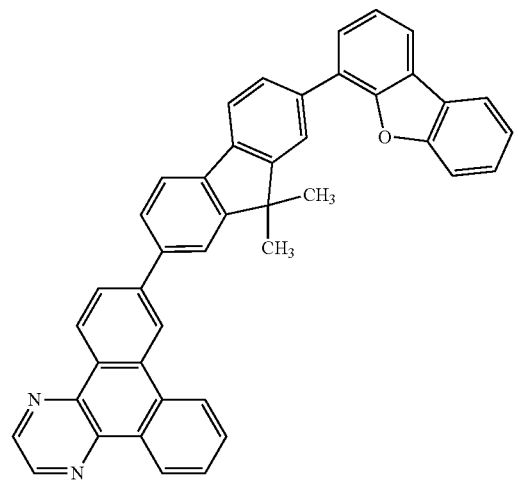
(213)
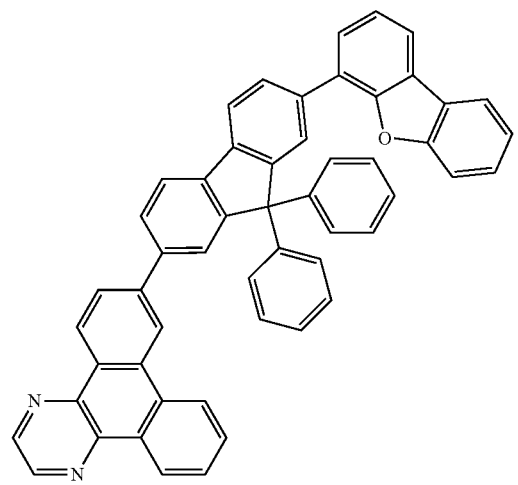
(214)
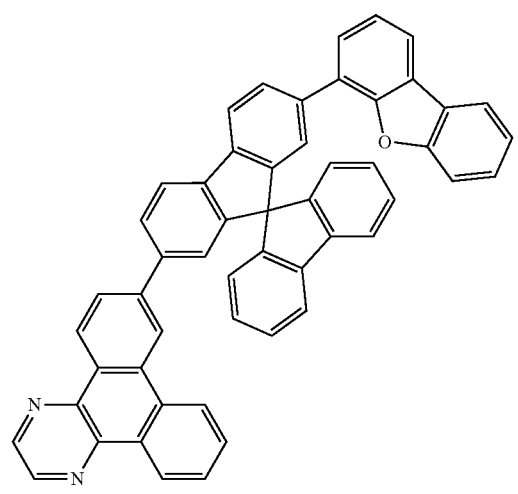

[Chemical Formula 25]
(215)
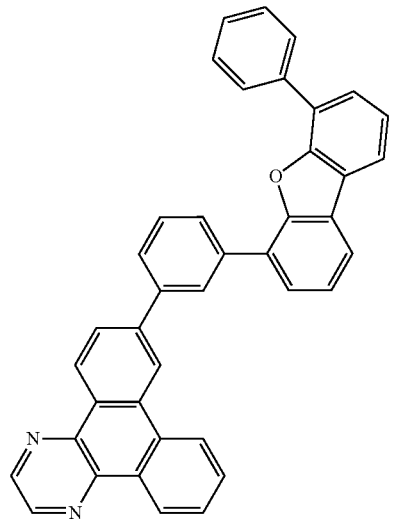
(216)
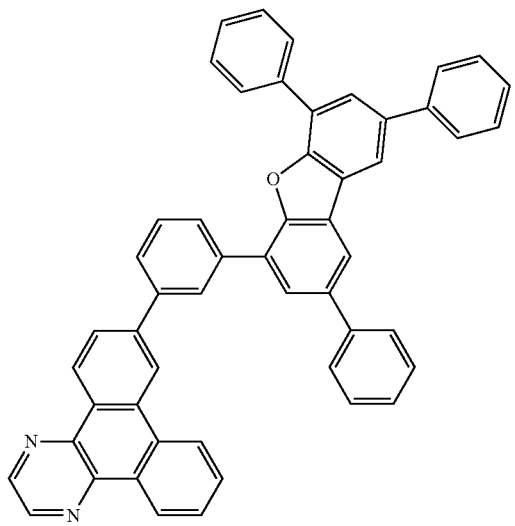
(217)
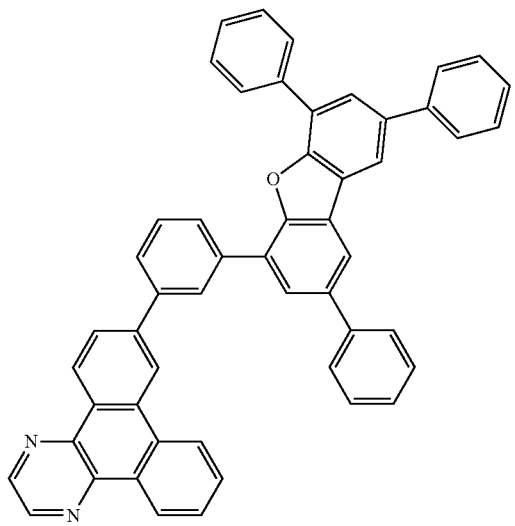
(218)
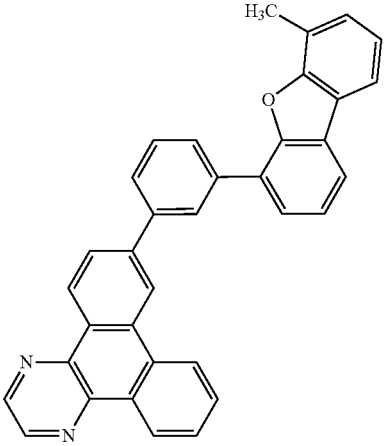
(219)
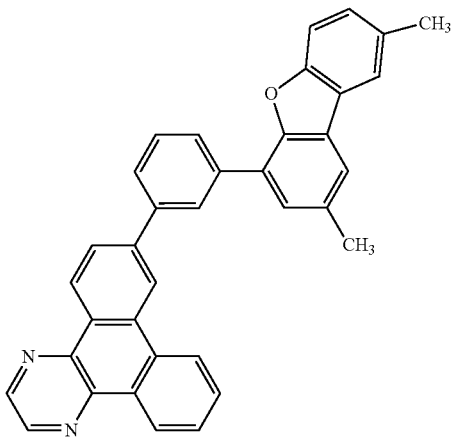
(220)
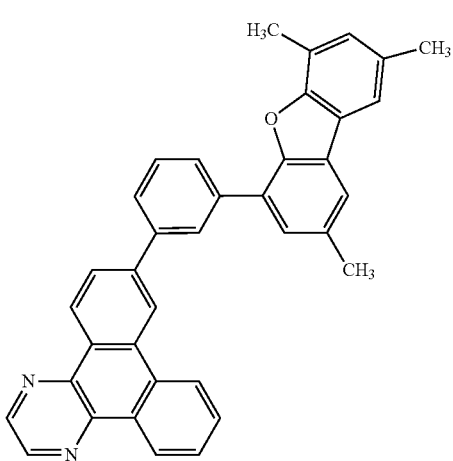

(221)
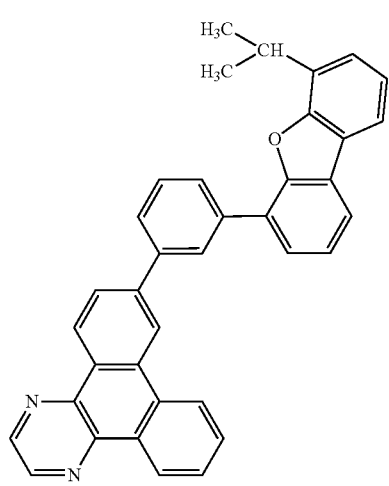
(222)
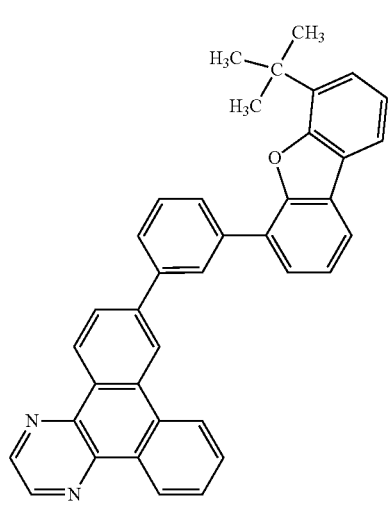
(223)
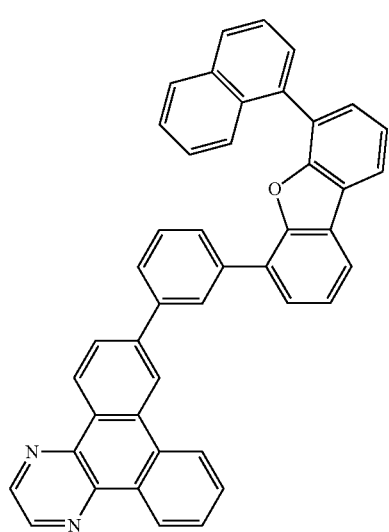
[Chemical Formula 26]
(224)
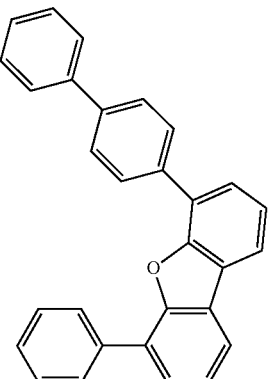
(225)
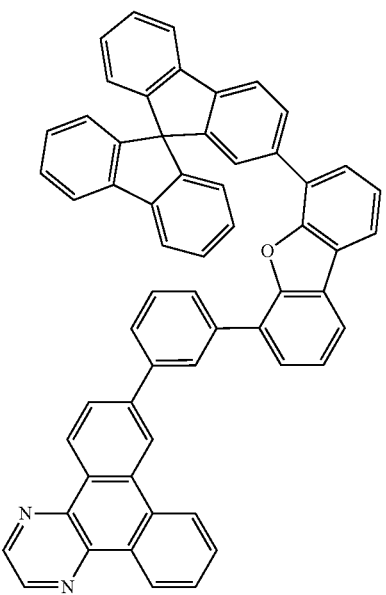

(226)
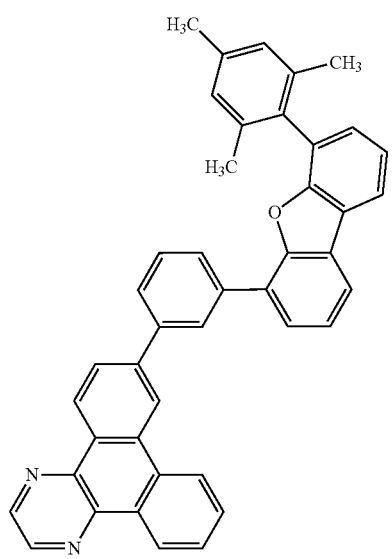
(227)
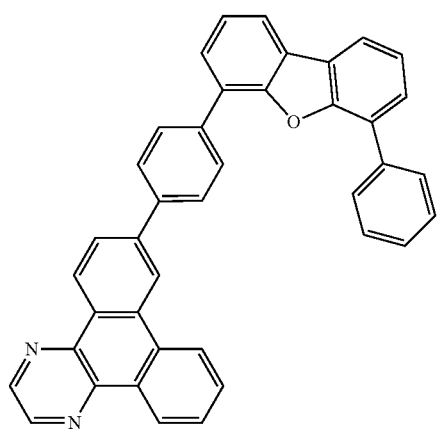
(228)
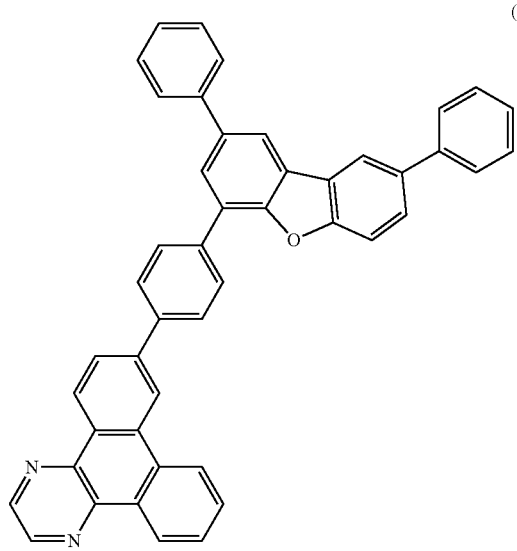
(229)
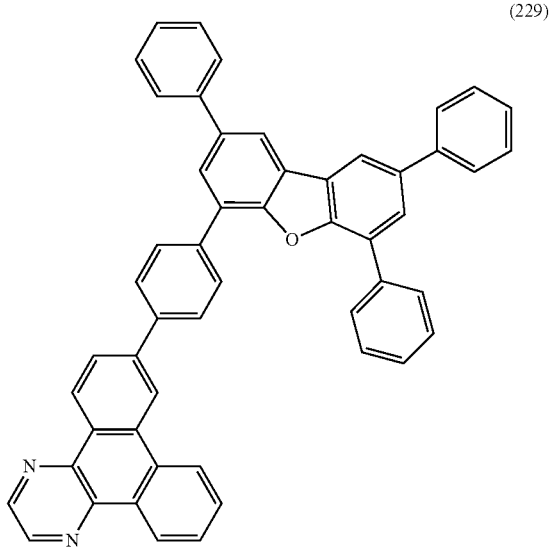
(230)
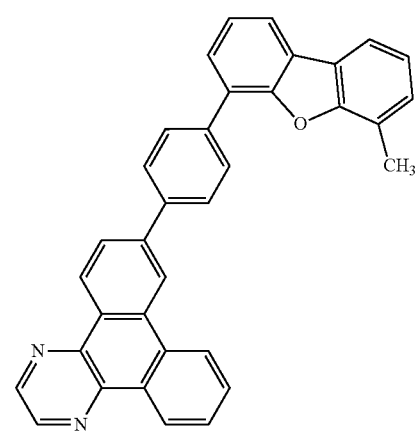
(231)
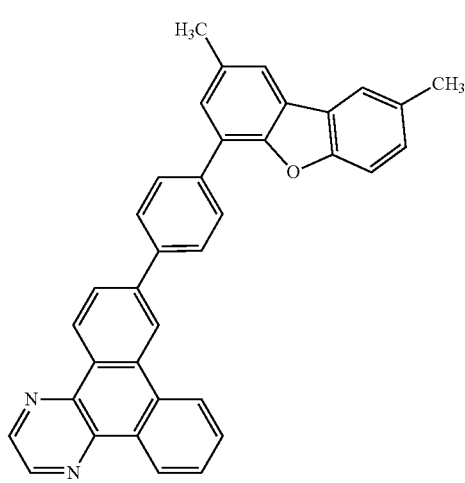

(232)
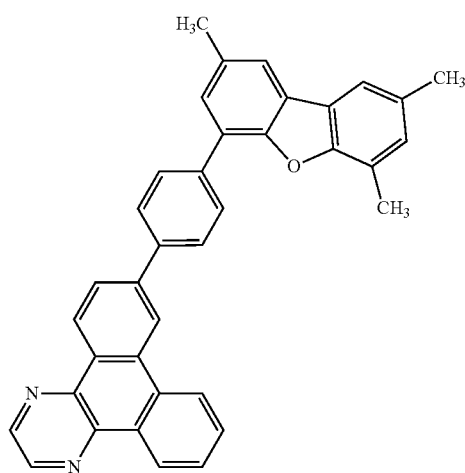
[Chemical Formula 27]
(233)
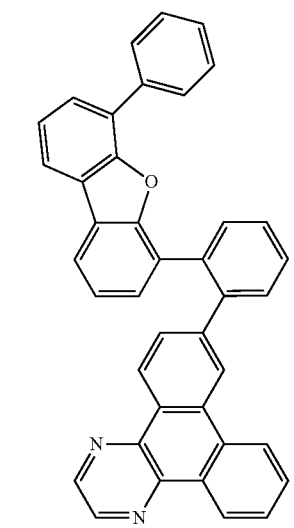
(234)
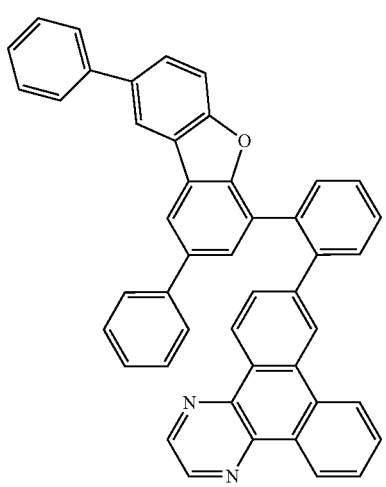
(235)
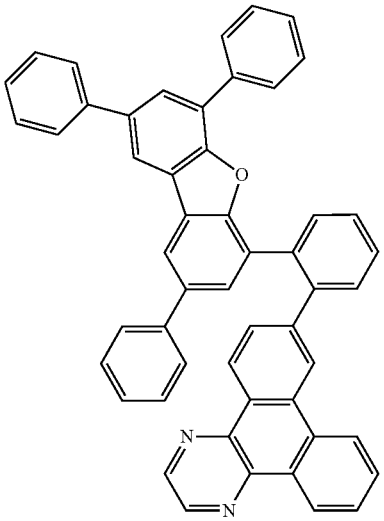
(236)
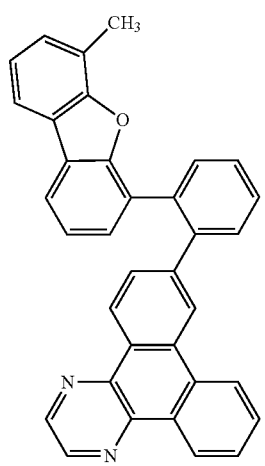
(237)
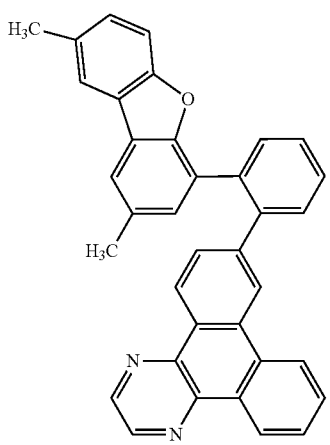

[Chemical Formula 28]
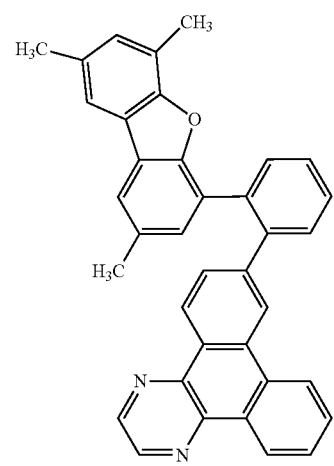 (238)
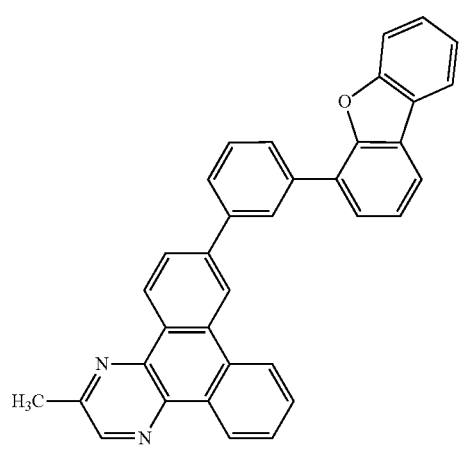 (239)
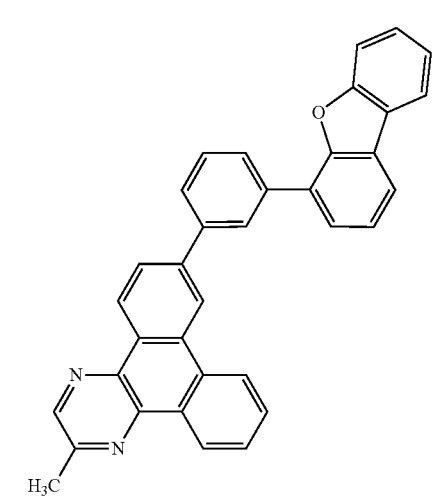 (240)
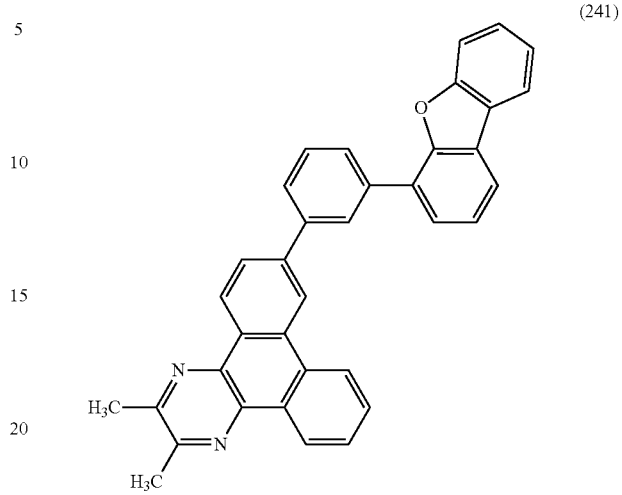 (241)(242)(243)

[Chemical Formula 29]
(244)
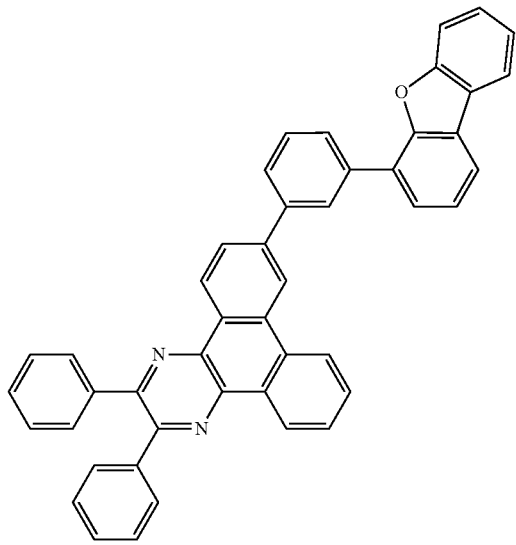
(245)
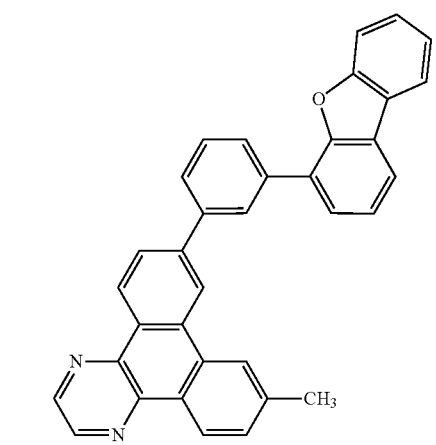
(246)
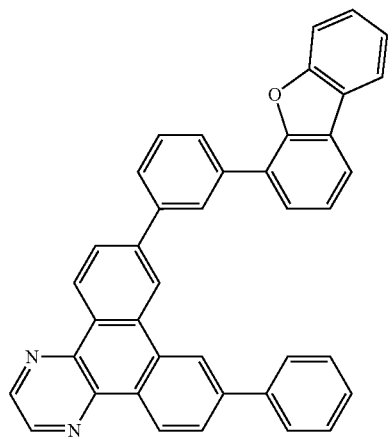
(300)
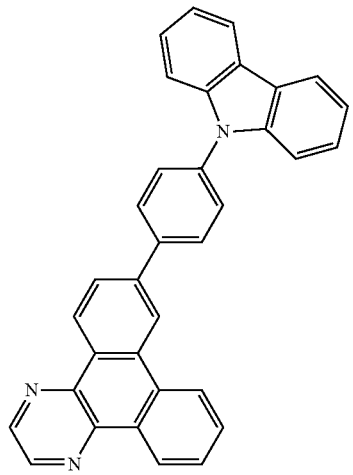
(301)
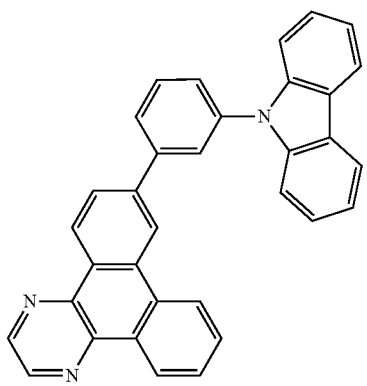
(302)
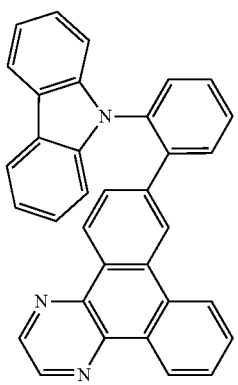

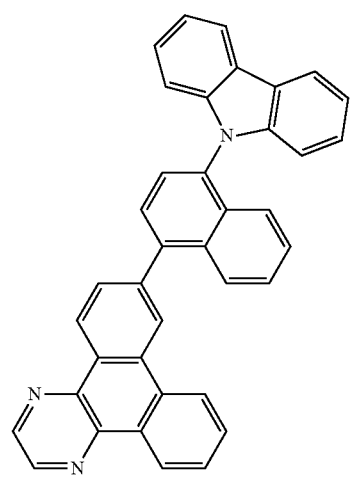
(303)
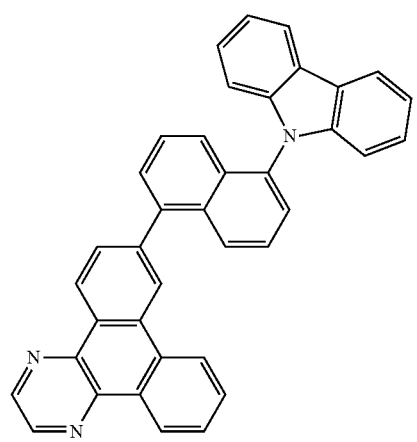
(304)
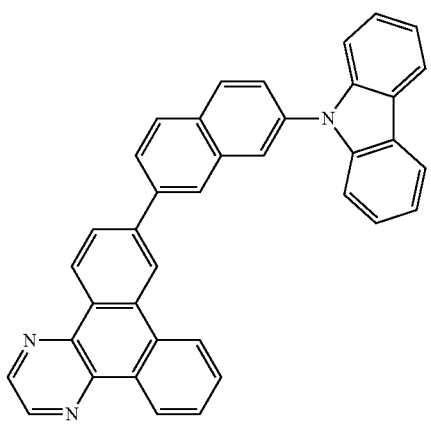
(305)
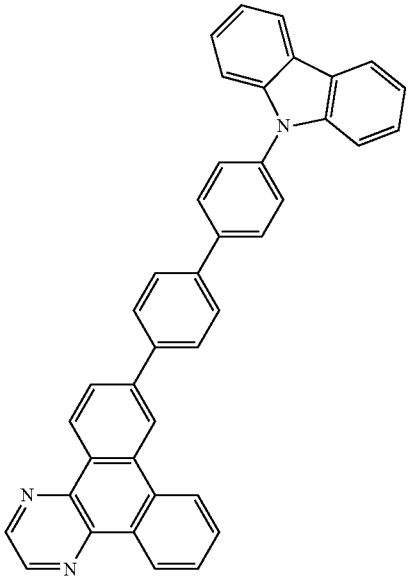
(306)
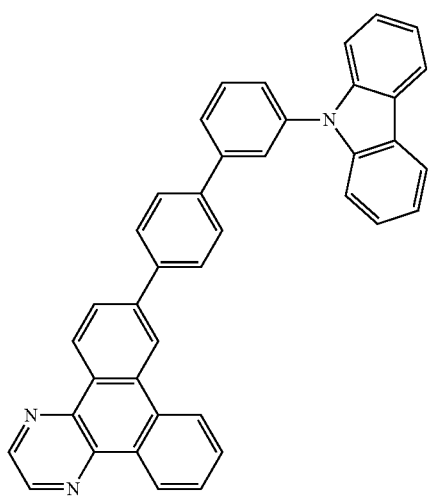
(307)
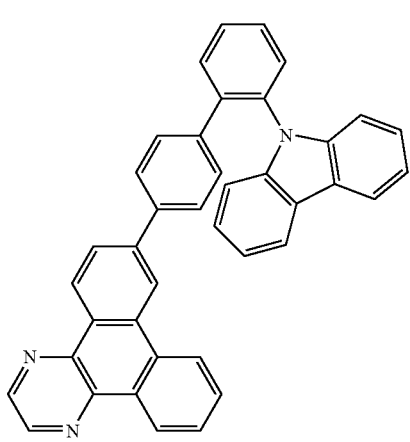
(308)

[Chemical Formula 30]
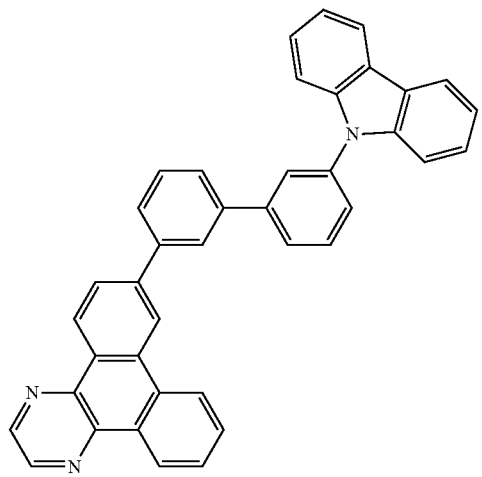
(309)
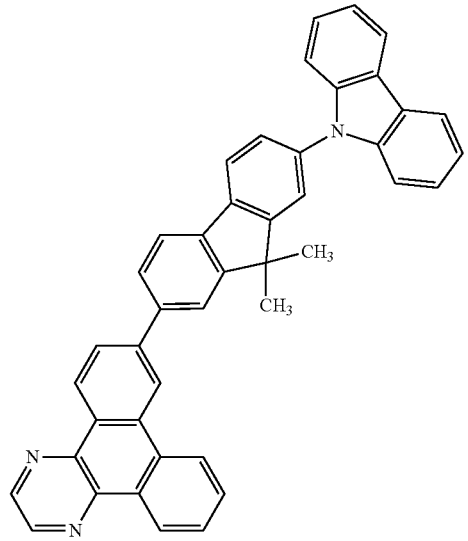
(312)
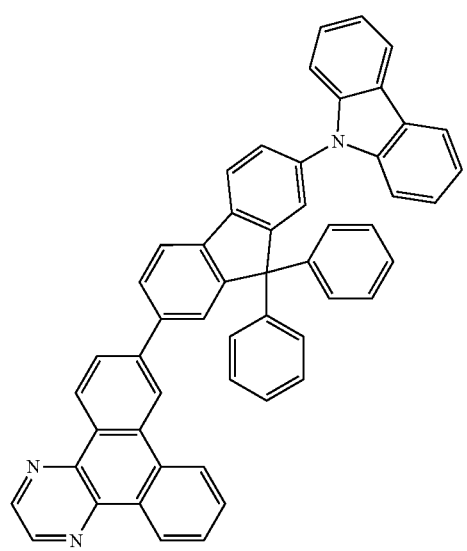
(313)
(310)
(311)
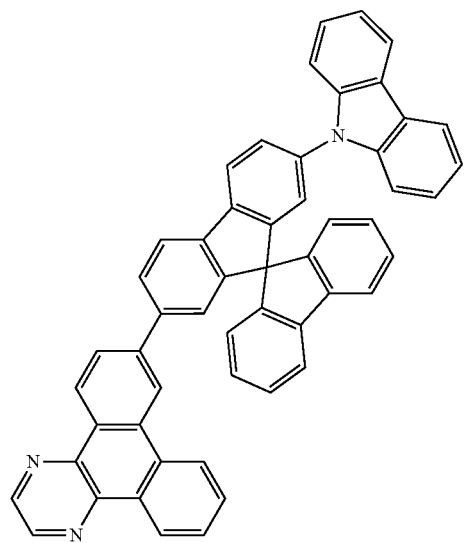
(314)

[Chemical Formula 31]
(315)
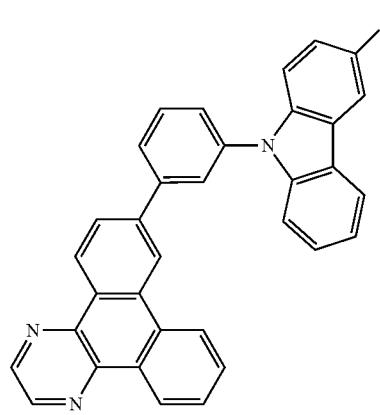
(316)
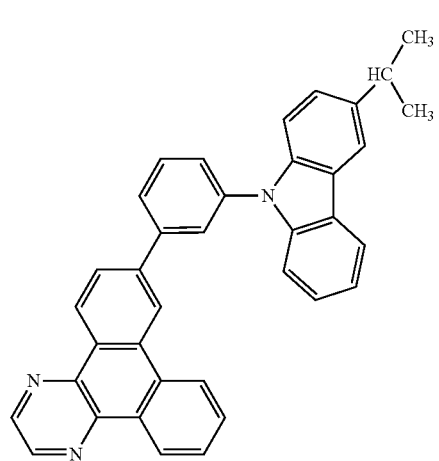
(317)
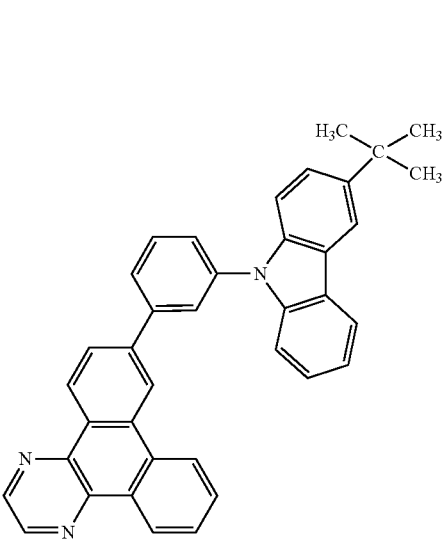
(318)
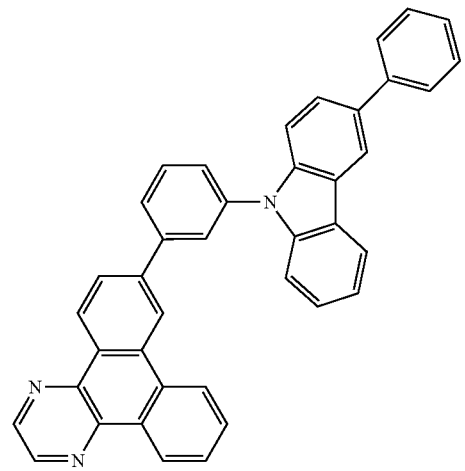
(319)
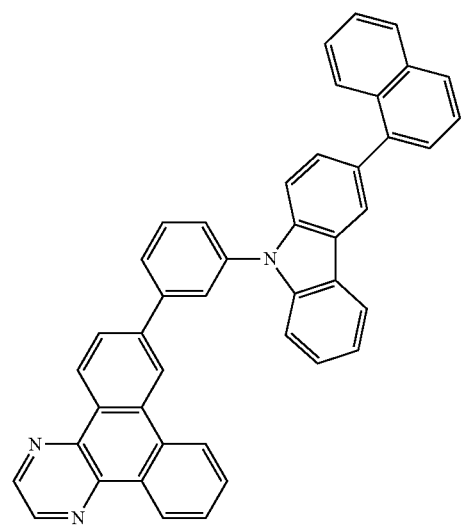
(320)
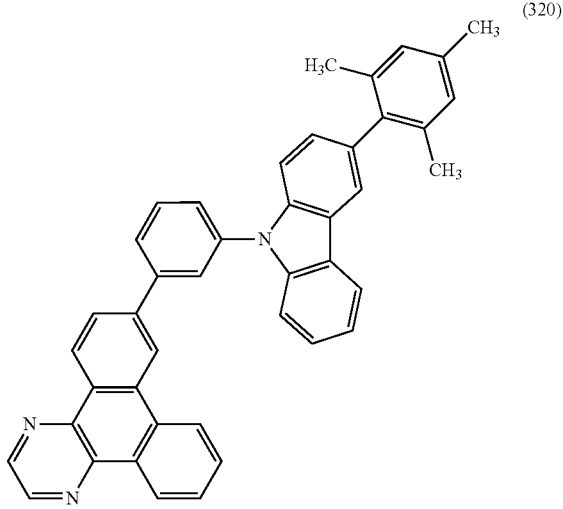

(321)
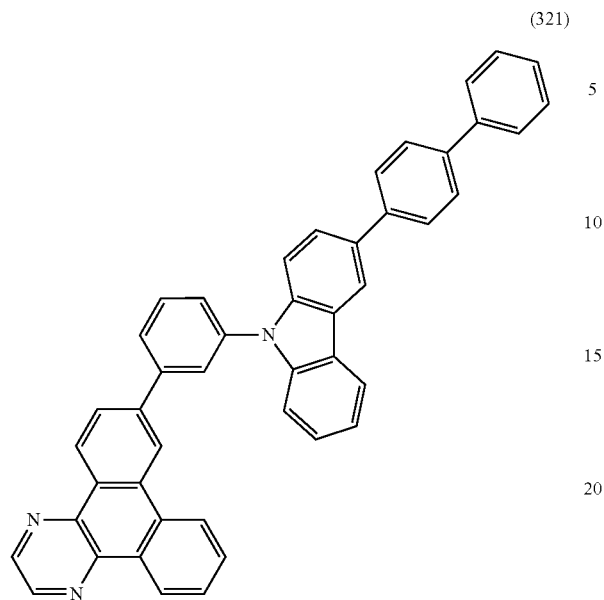
(322)
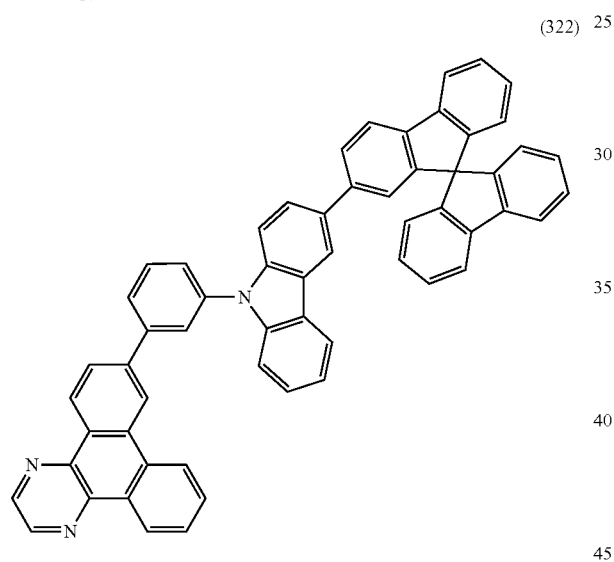
[Chemical Formula 32]
(323)
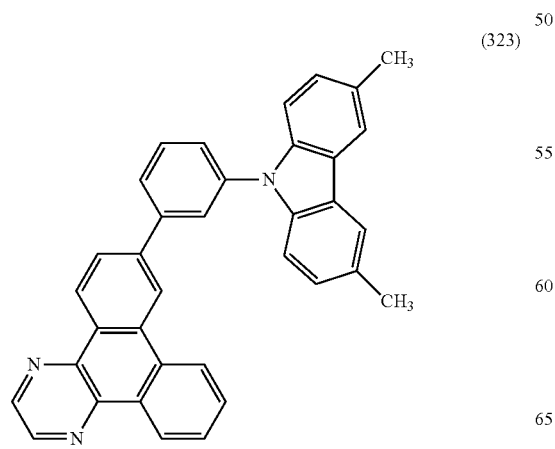
(324)
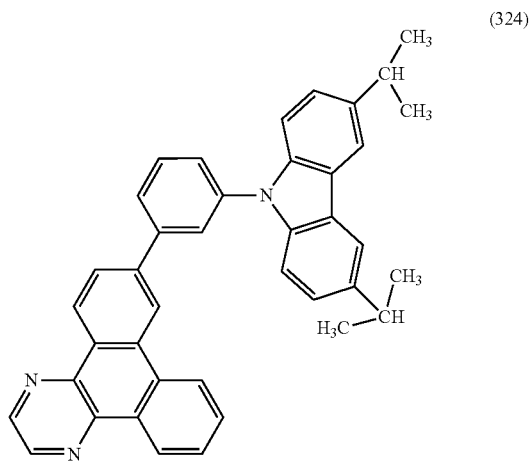
(325)
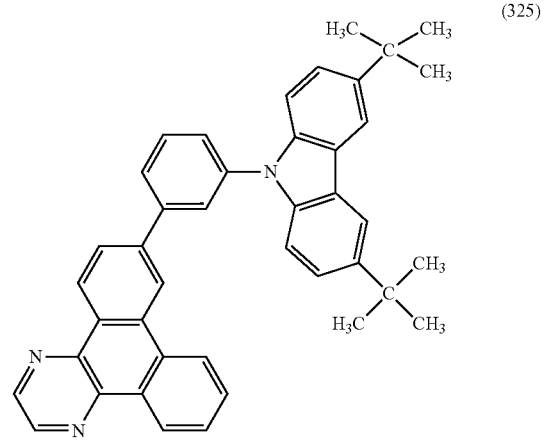
(326)
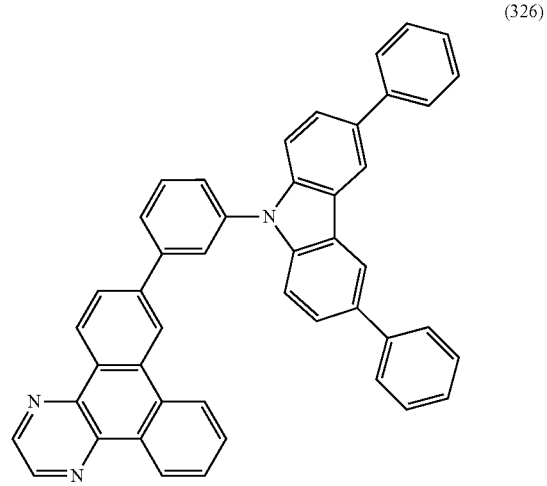

-continued
(327)
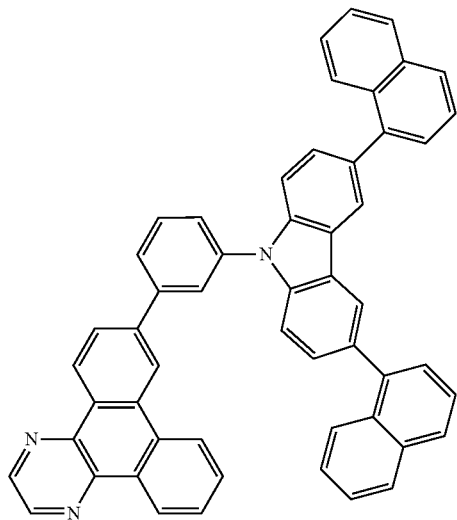
(328)
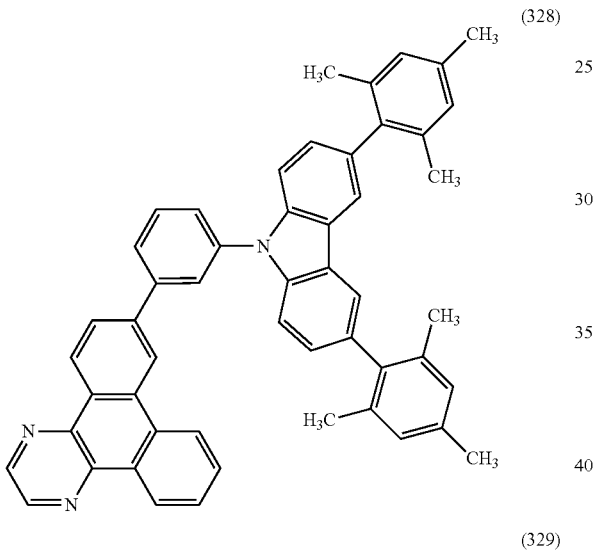
(329)
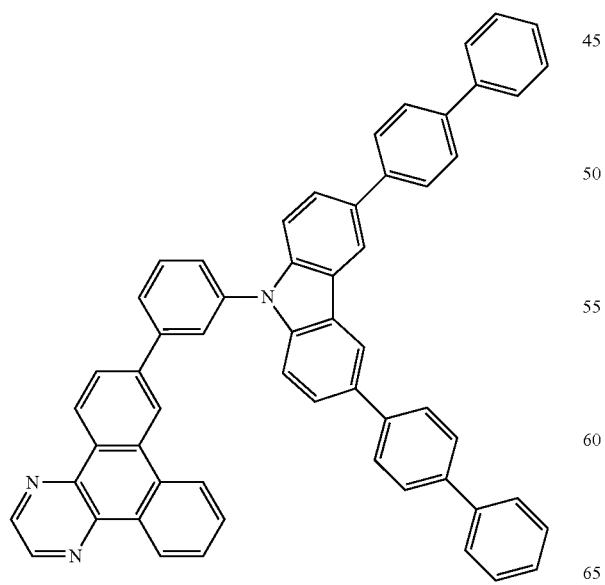
-continued
(330)
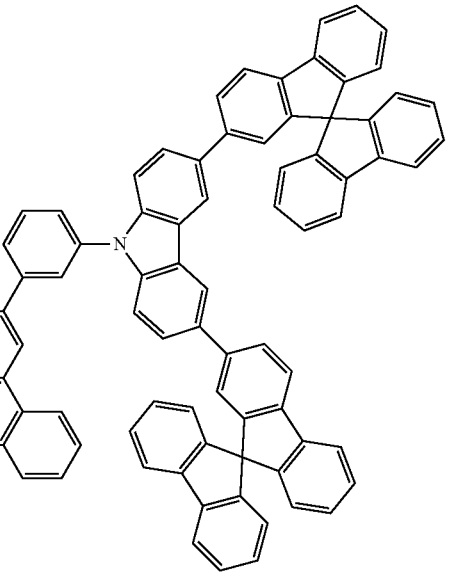
[Chemical Formula 33]
(331)
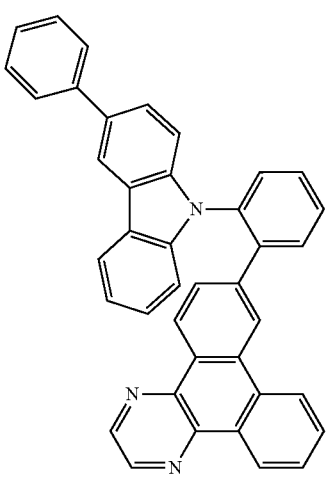
(332)

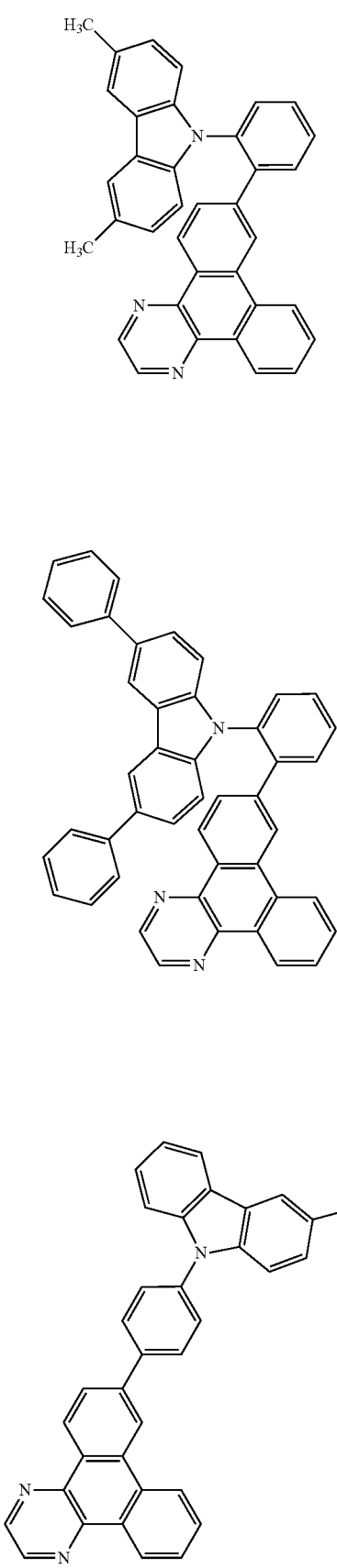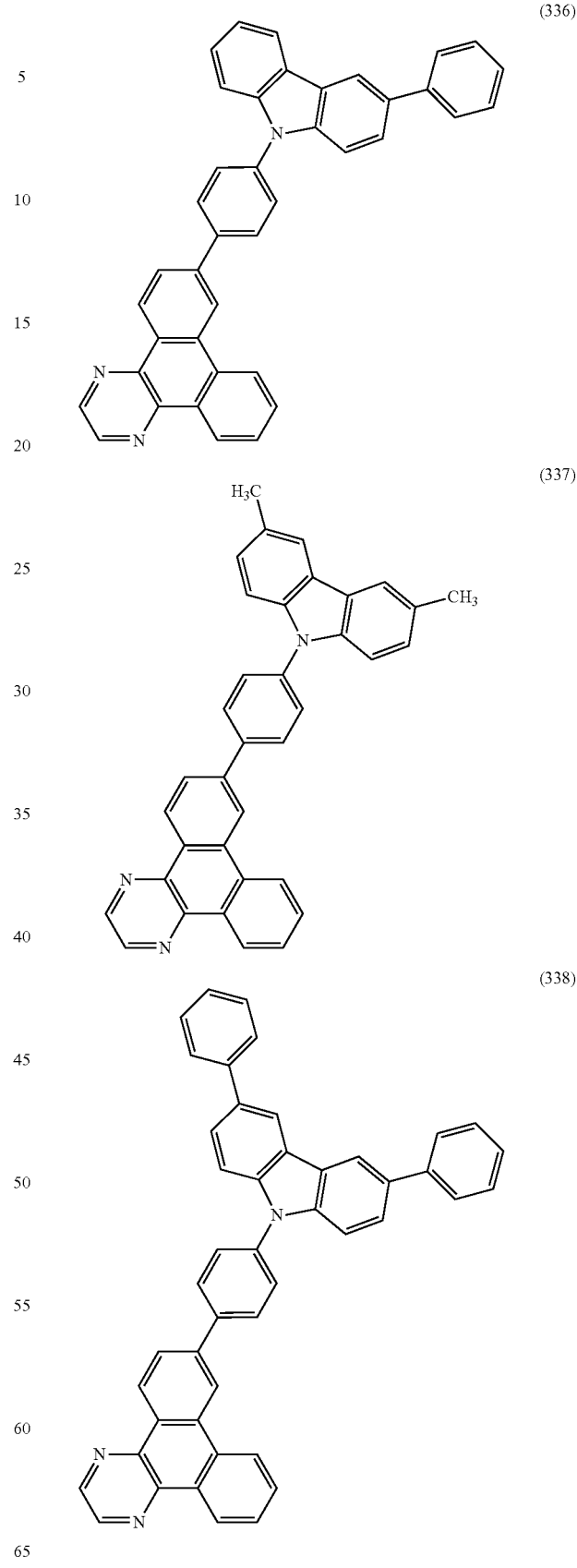

[Chemical Formula 34]
(339)
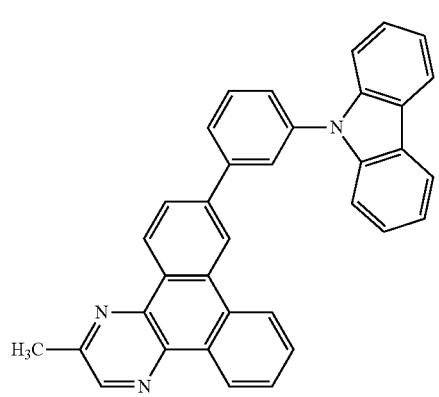
(340)
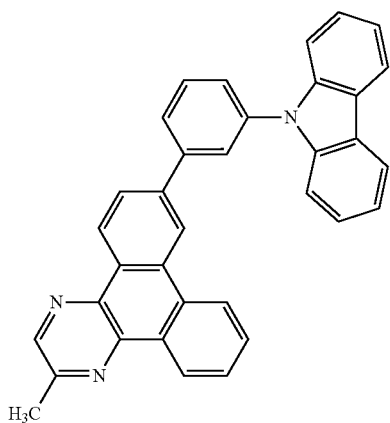
(341)
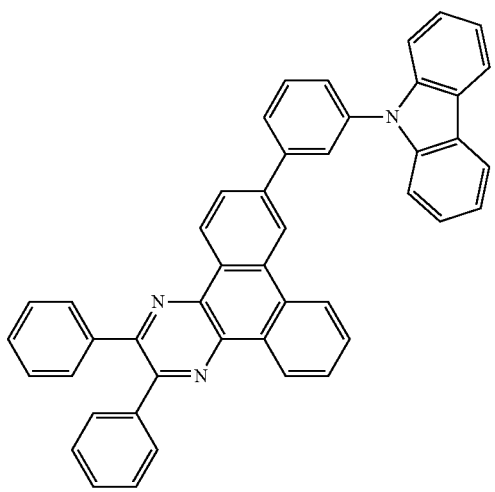
(342)
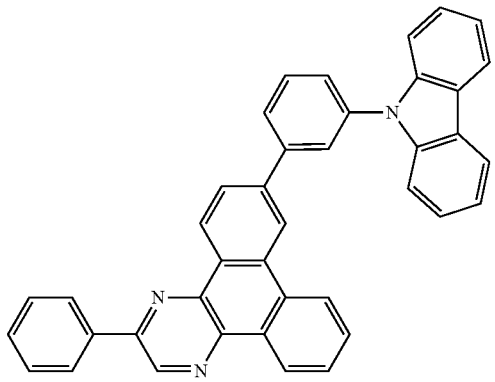
(343)
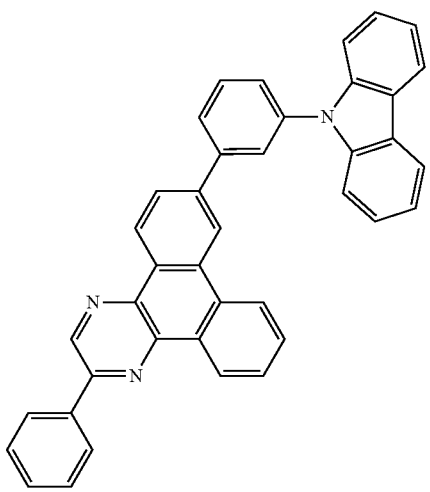
(344)
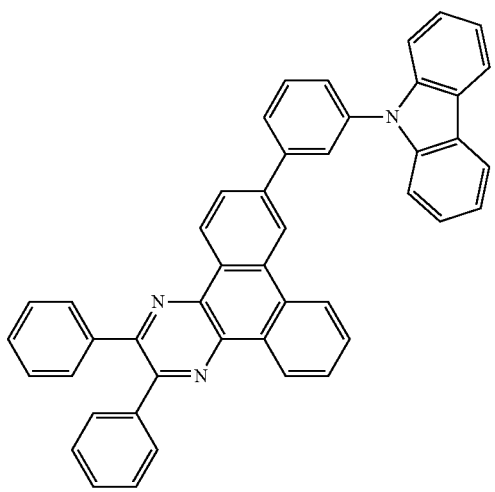

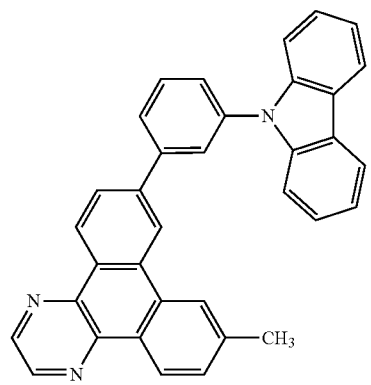
(345)
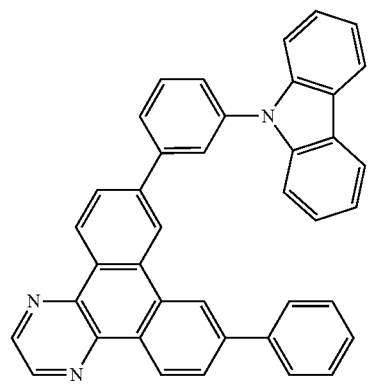
(346)
[Chemical Formula 35]
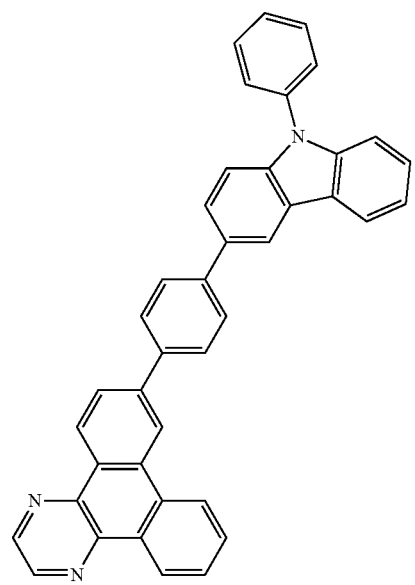
(400)
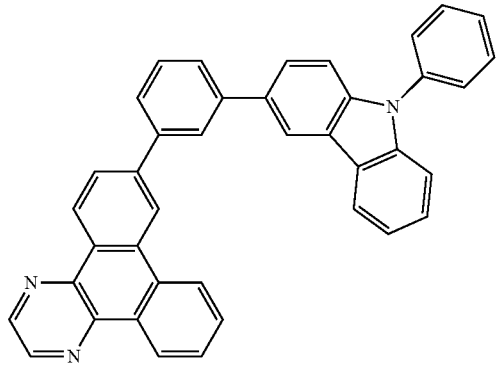
(401)
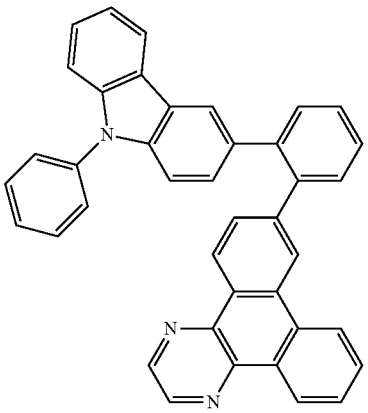
(402)
(403)

-continued
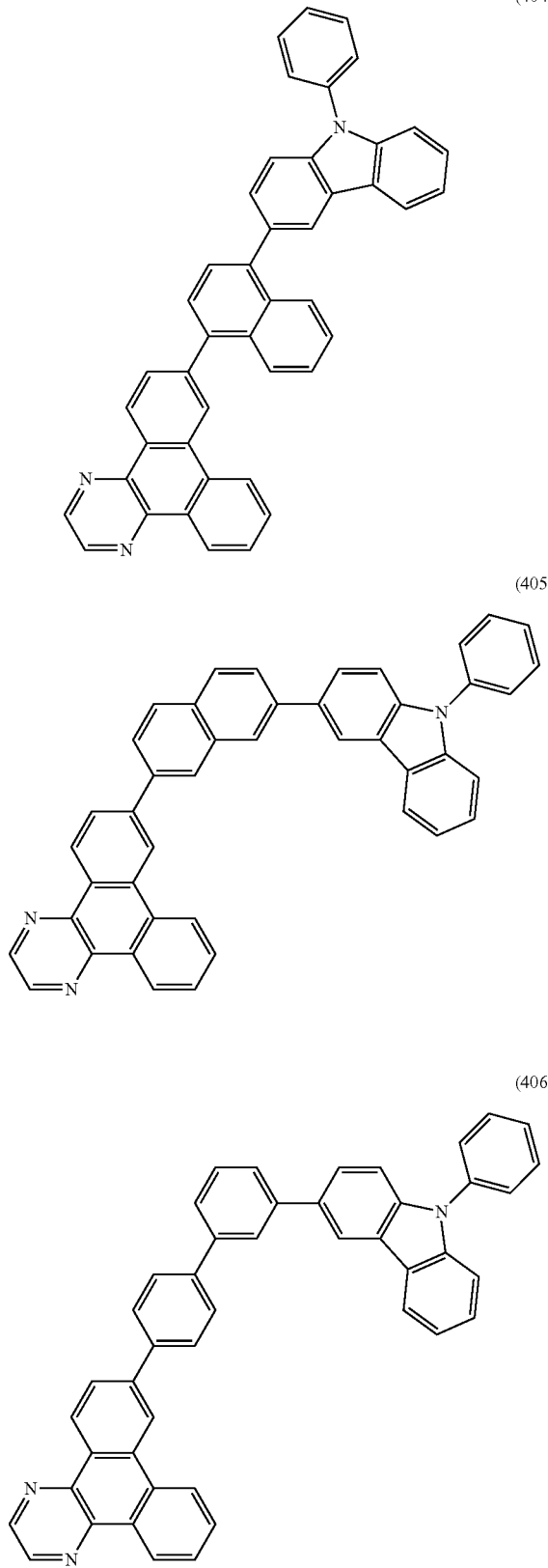
[Chemical Formula 36]
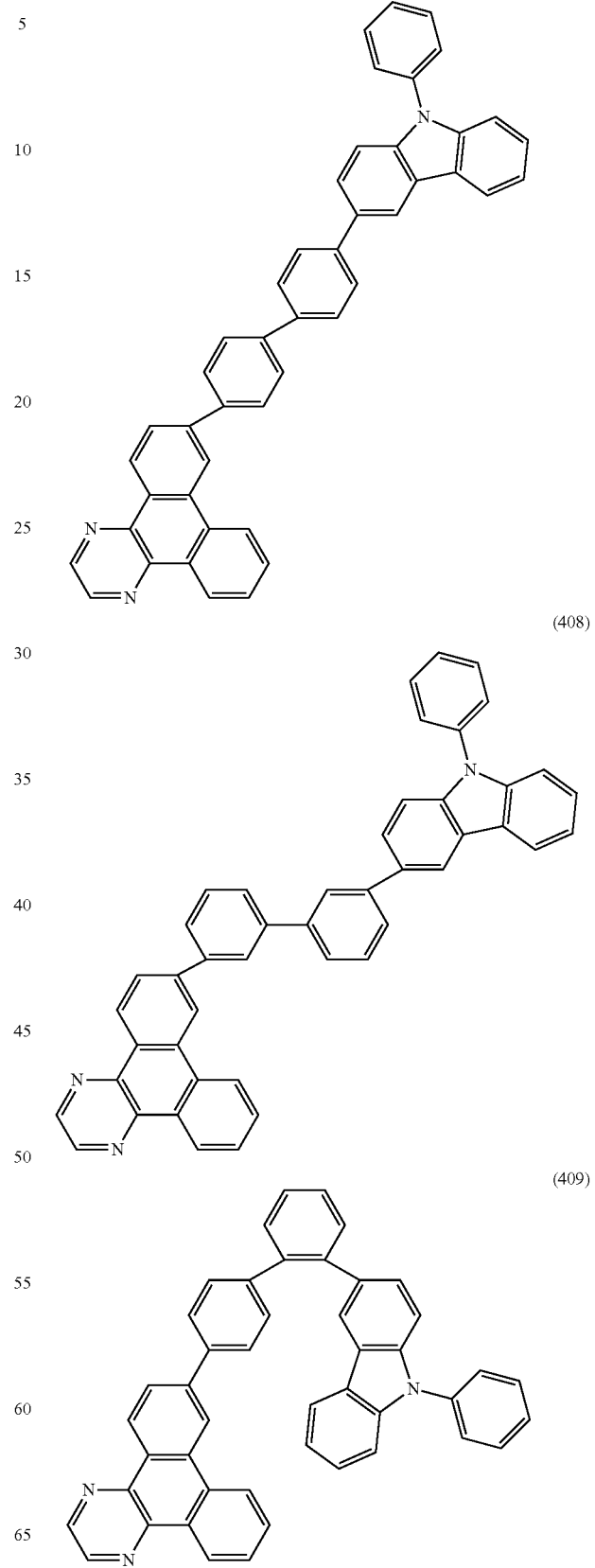

(410)
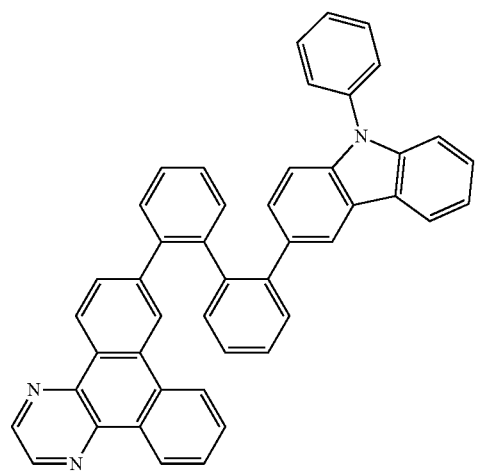
(411)
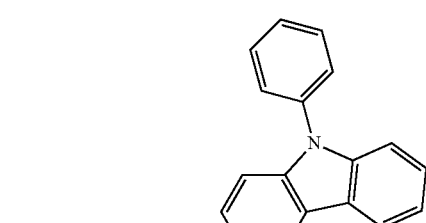
(412)
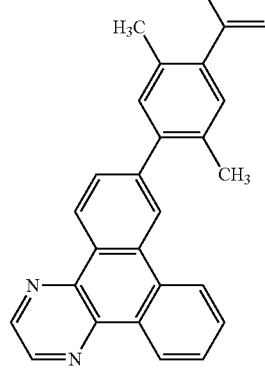
[Chemical Formula 37]
(413)
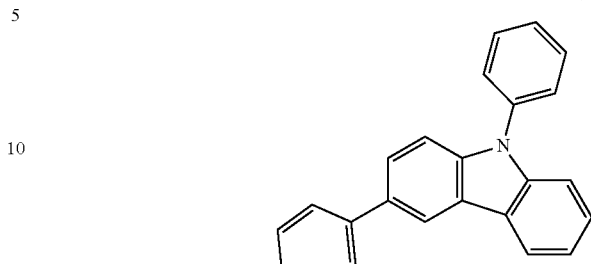
(414)
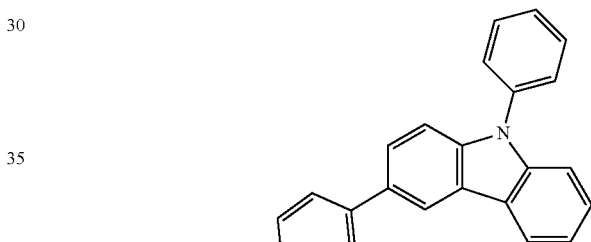
(415)
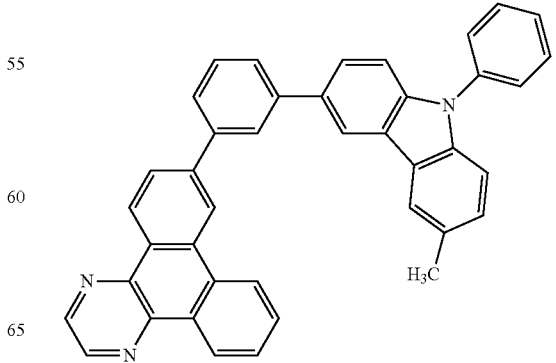

[Chemcial Formula 38]

-continued
(423)
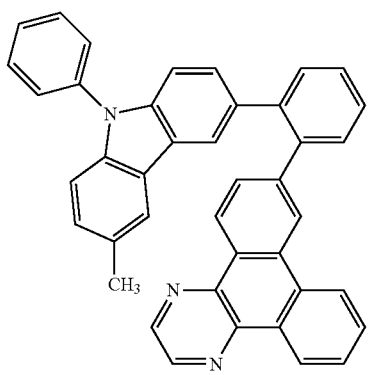
(424)
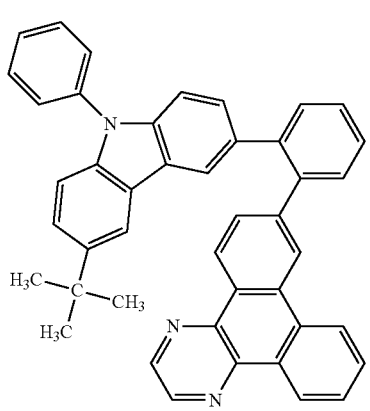
[Chemical Formula 39]
(425)
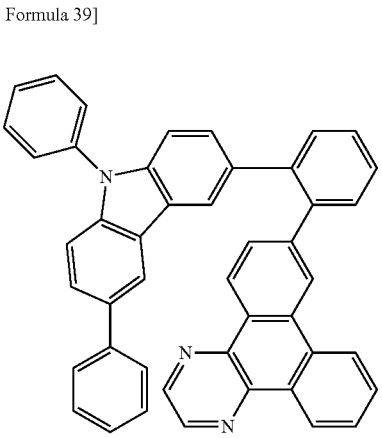
-continued
(426)
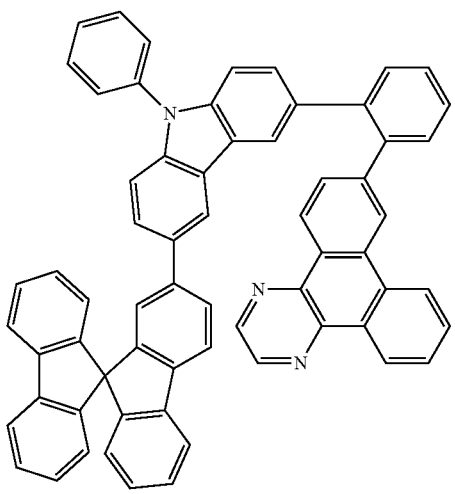
(427)
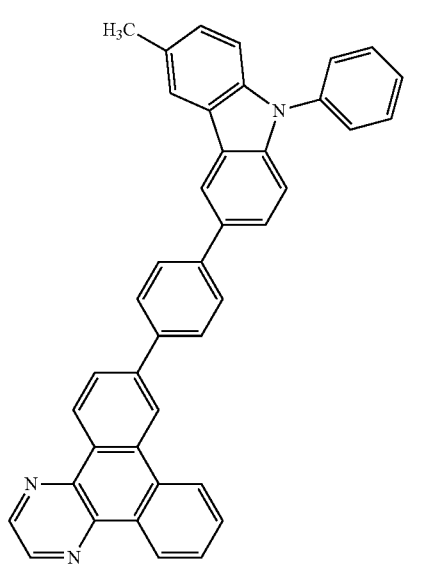
(428)
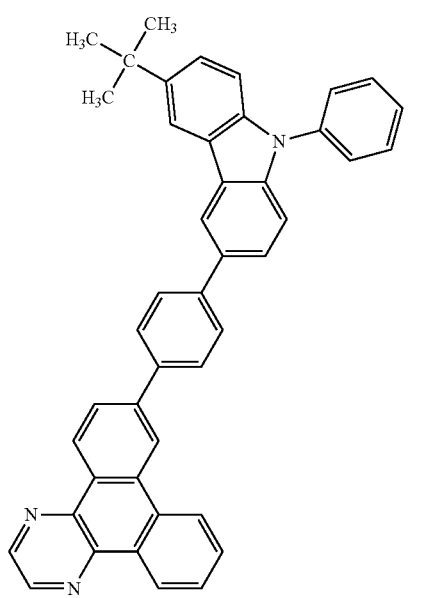

(429)
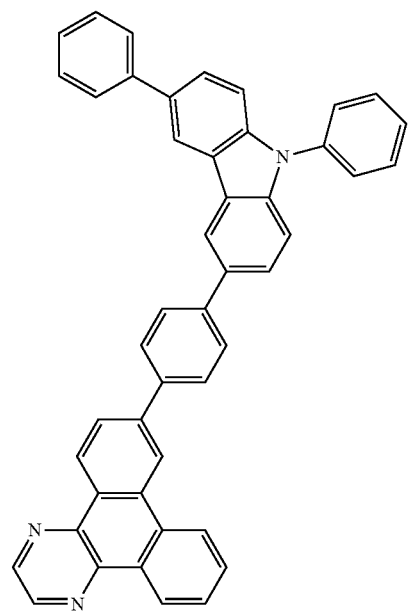
(430)
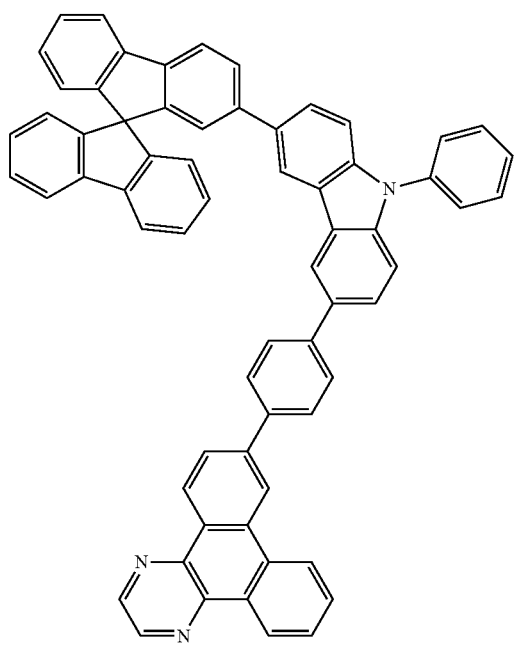
[Chemical Formula 40]
(431)
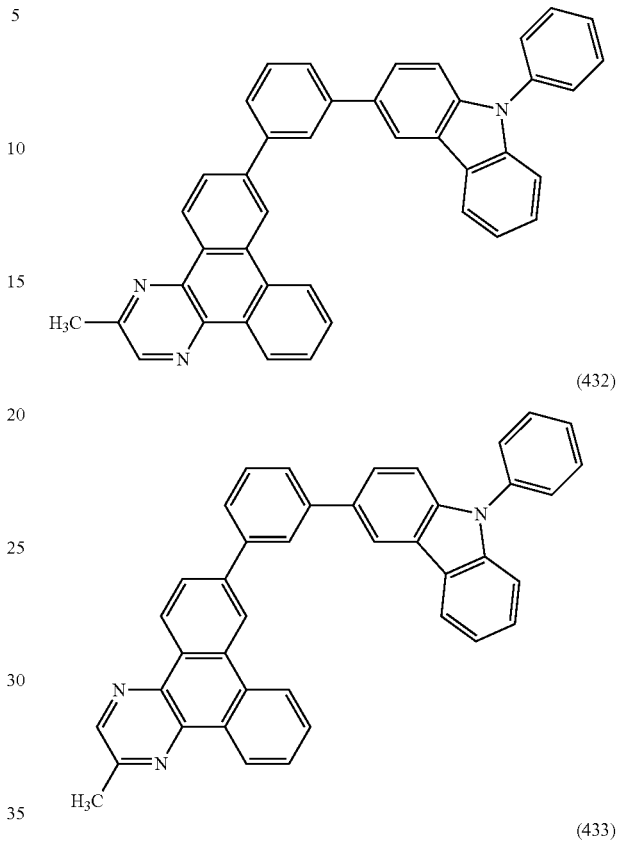
(432)
(433)
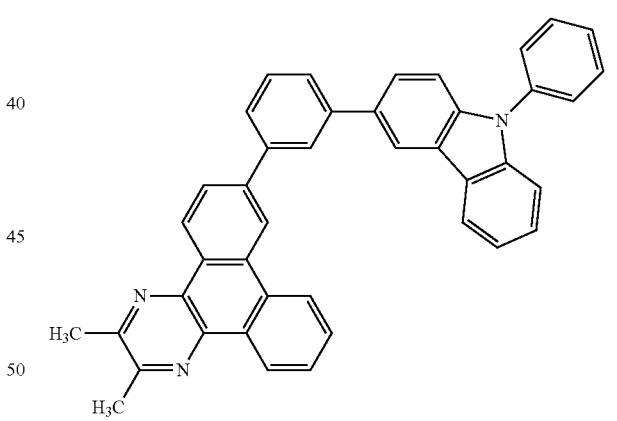
(434)
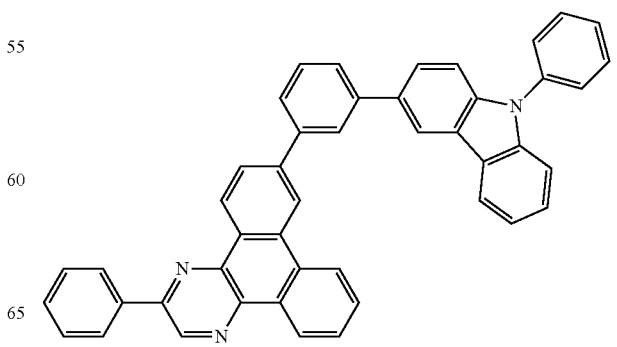

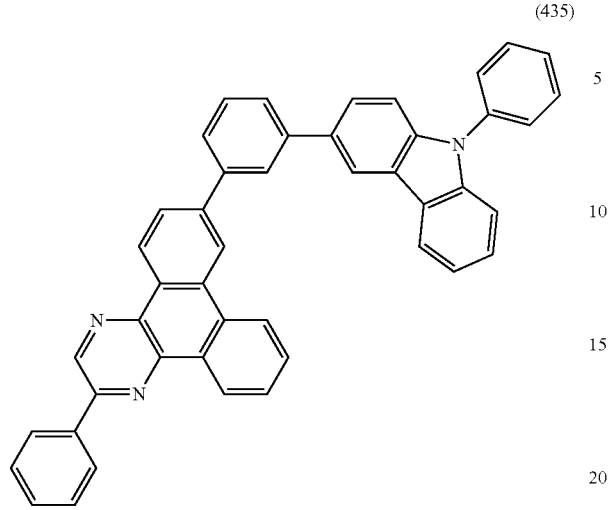
[Chemical Formula 41]
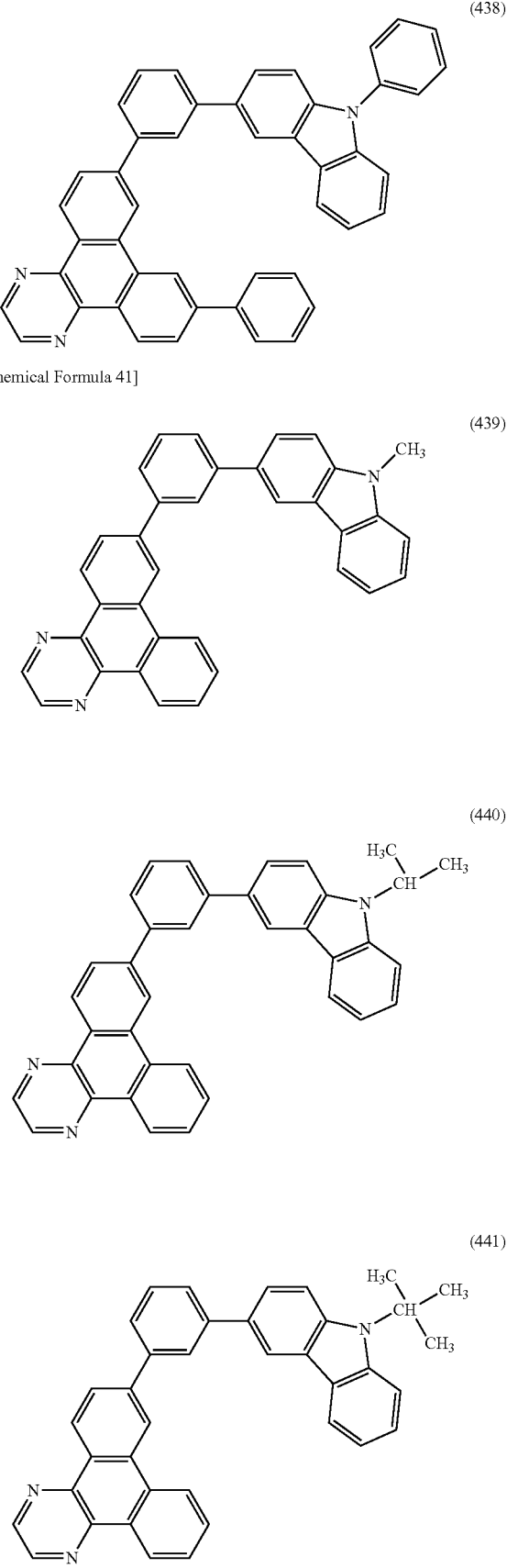

(442)
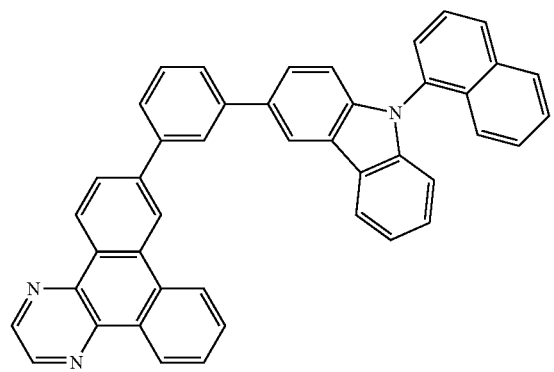
(443)
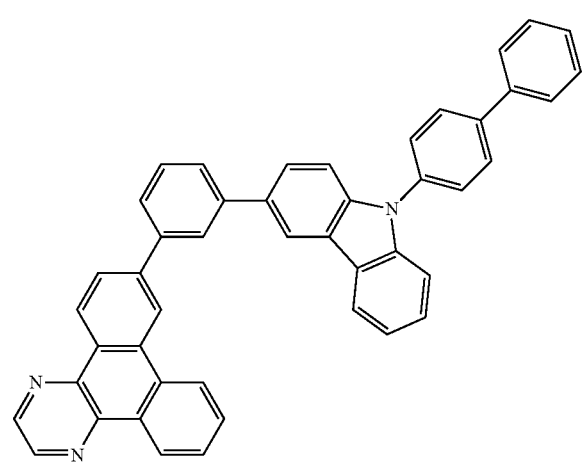
(444)
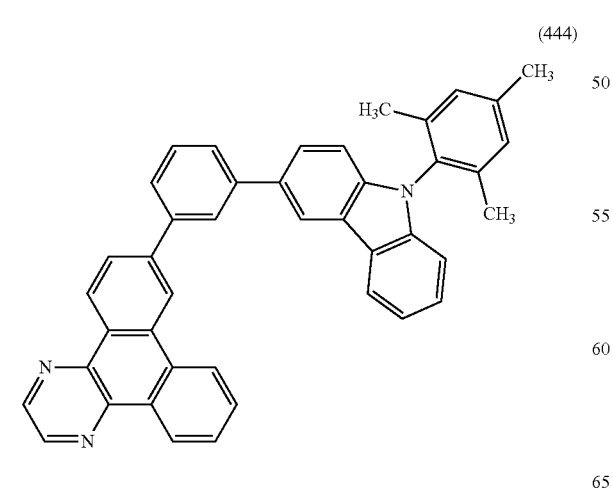
(445)
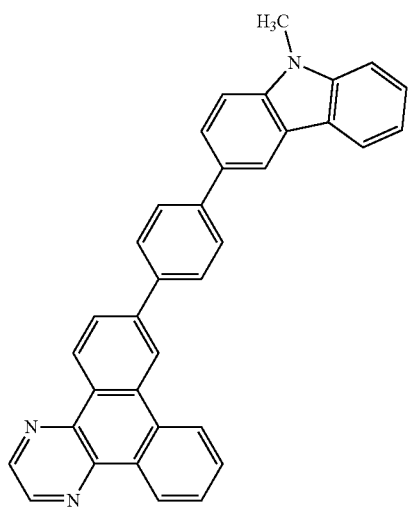
[Chemical Formula 42]
(446)
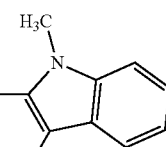
(447)
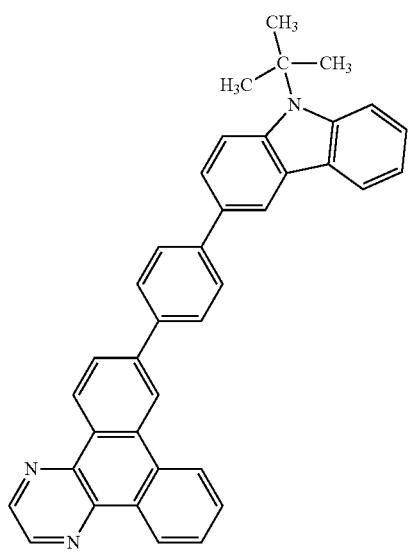

(448)
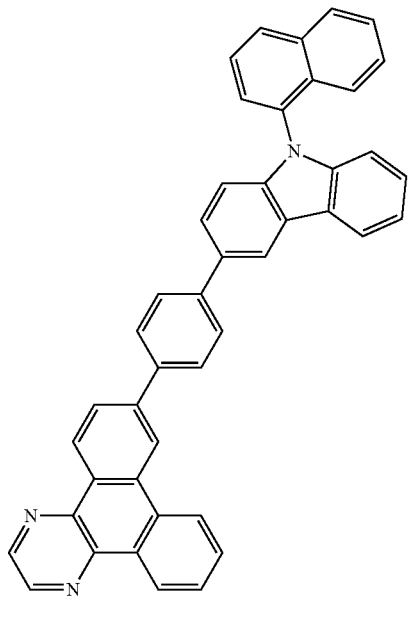
(449)
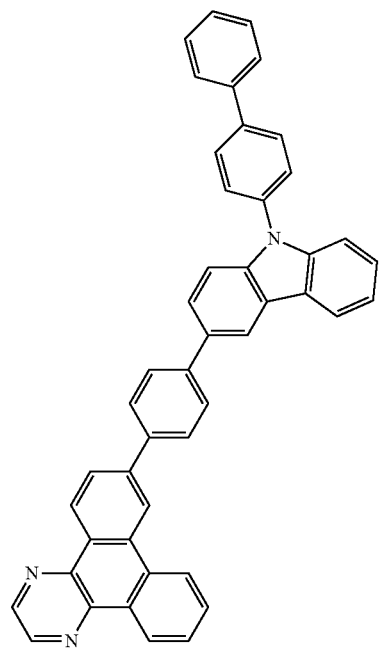
(450)
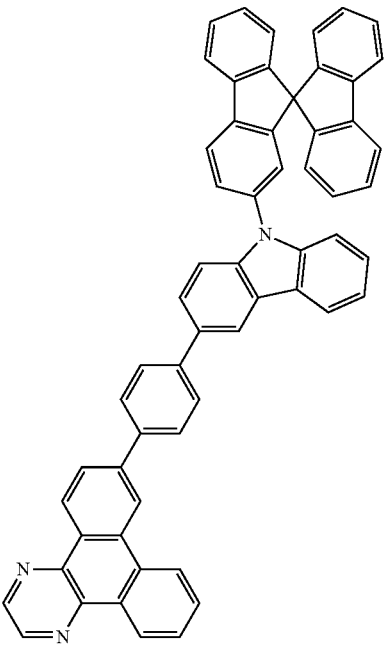
(451)
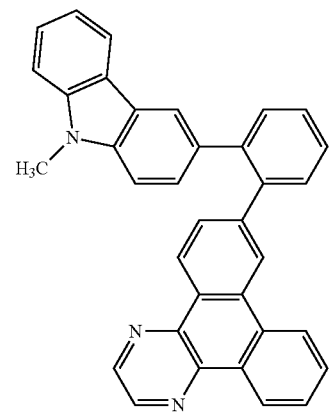
(452)
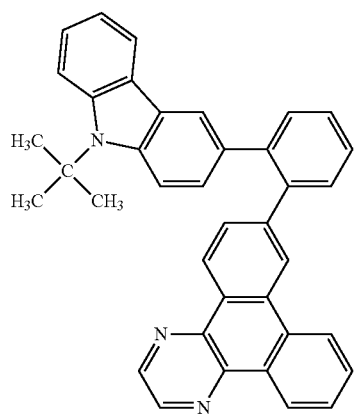

[Chemical Formula 43]
(453)
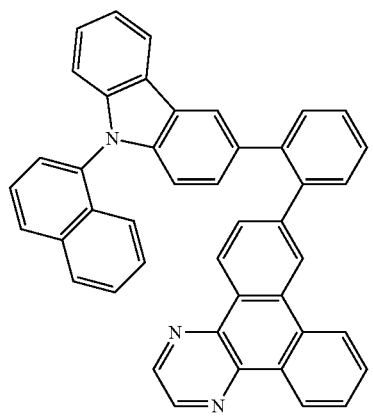
(454)
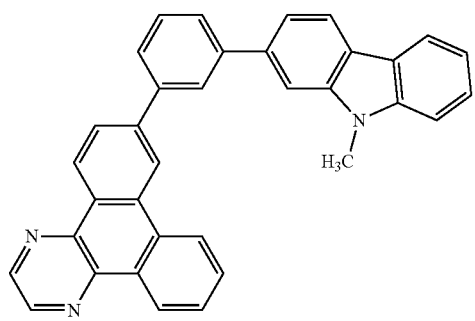
(455)
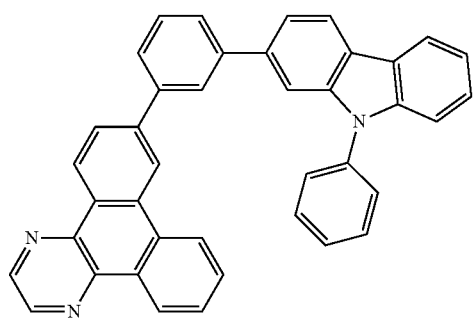
(456)
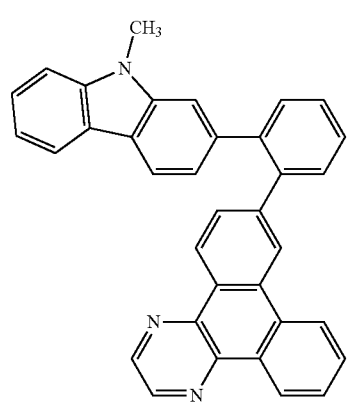
(457)
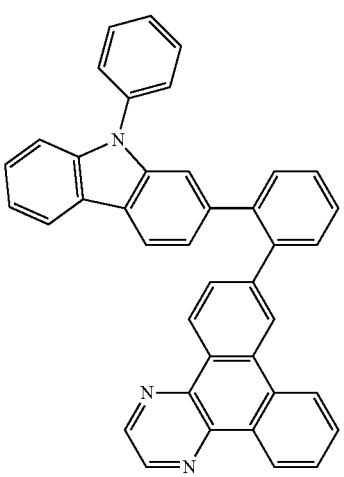
(458)
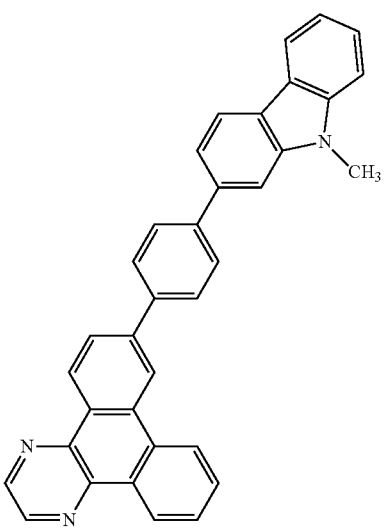
(459)
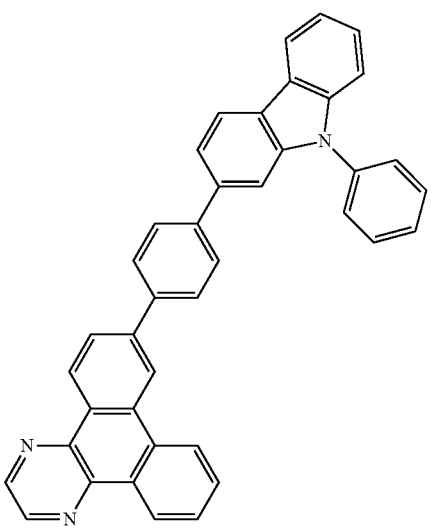

[Chemical Formula 44]
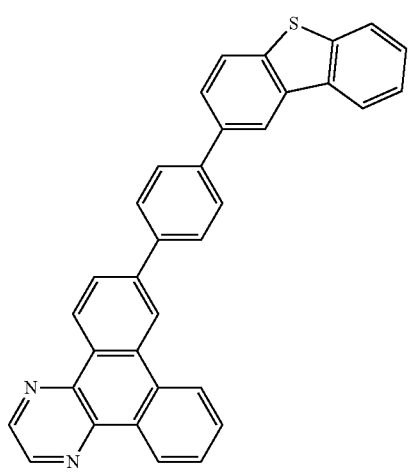
(500)
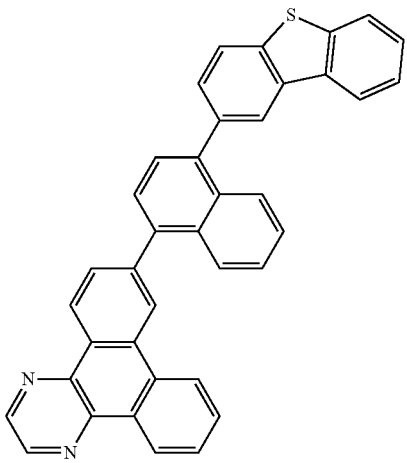
(503)
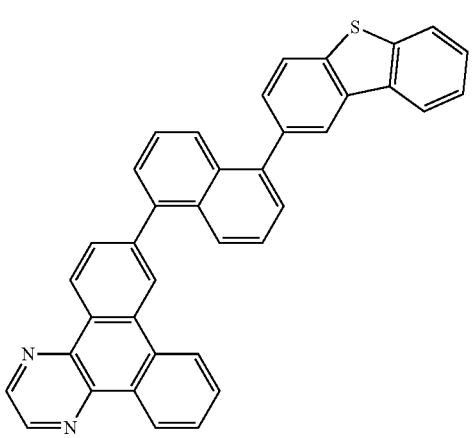
(504)
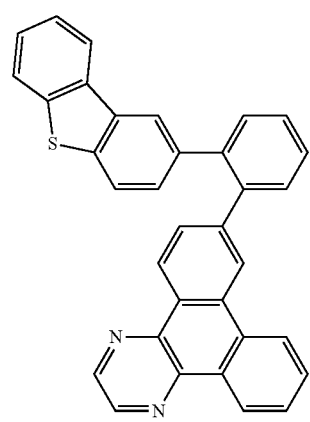
(501)
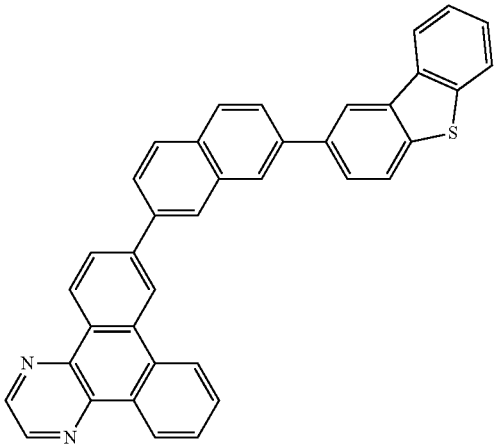
(505)
(502)

[Chemical Formula 45]
(506) 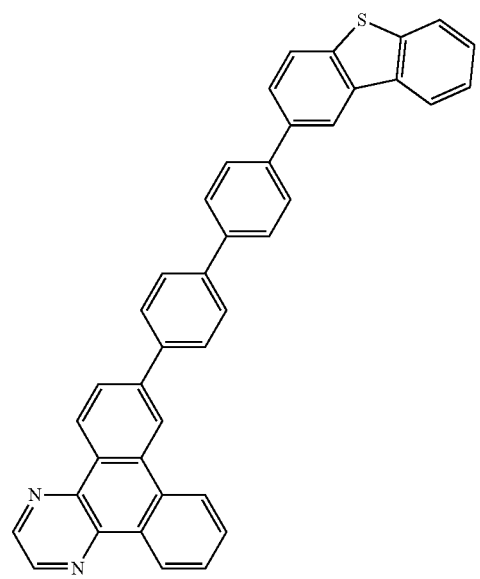
(507) 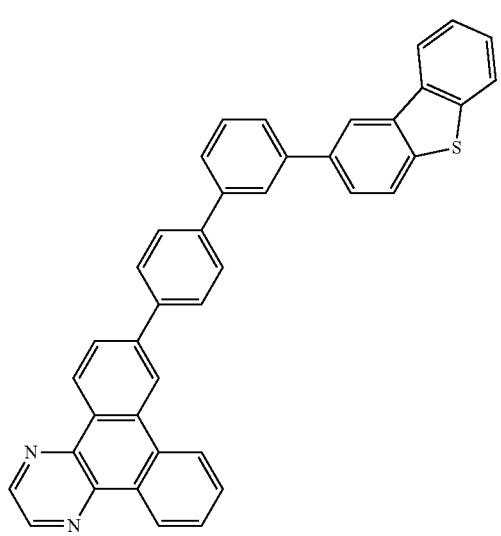
(508) 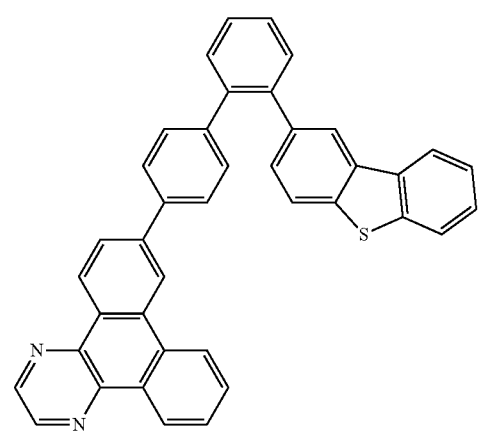
(509) 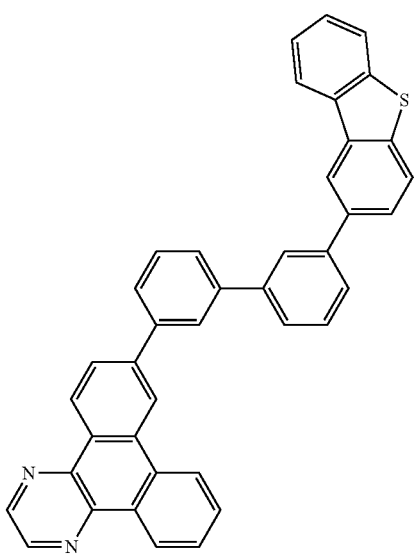
(510) 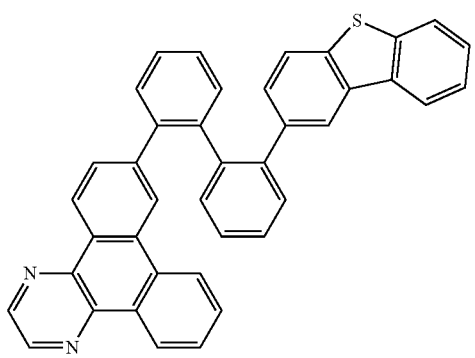
(511) 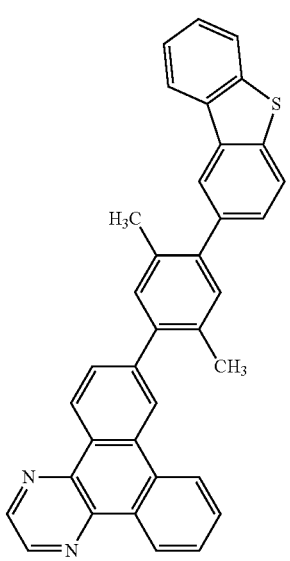

(512)
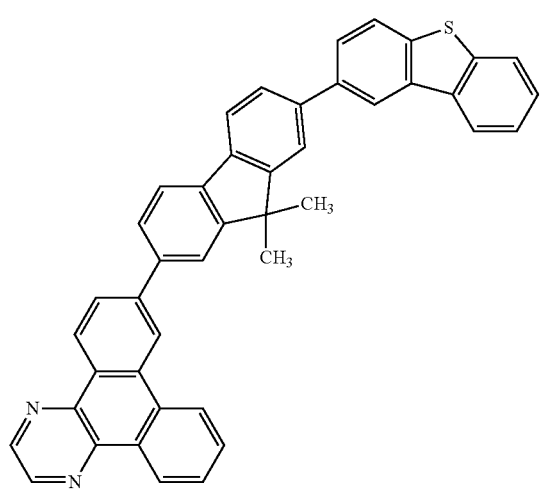
(513)
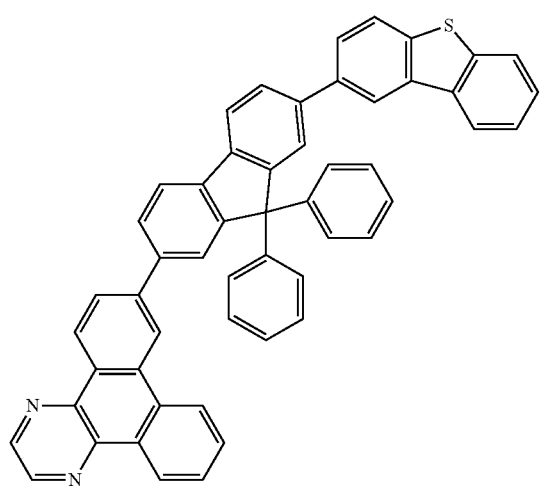
(514)
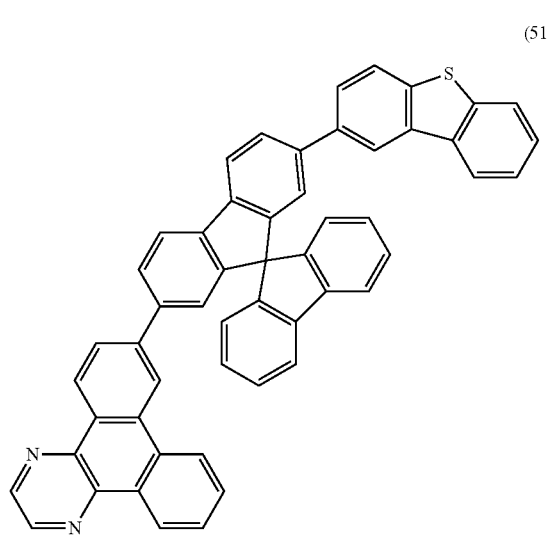
(515)
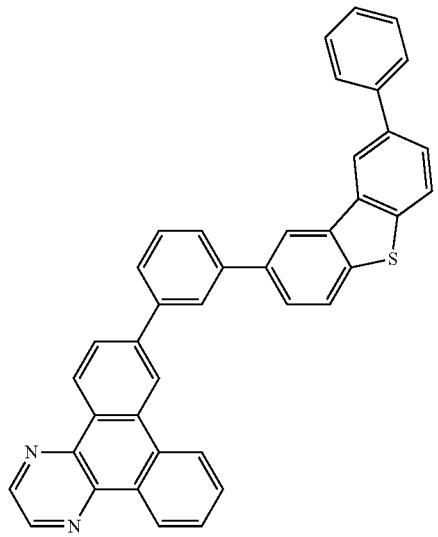
[Chemical Formula 46]
(516)
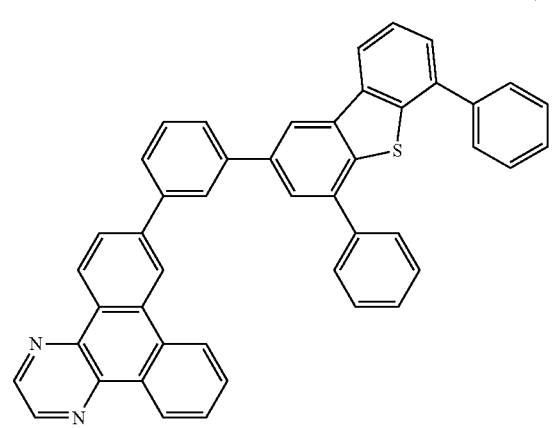
(517)
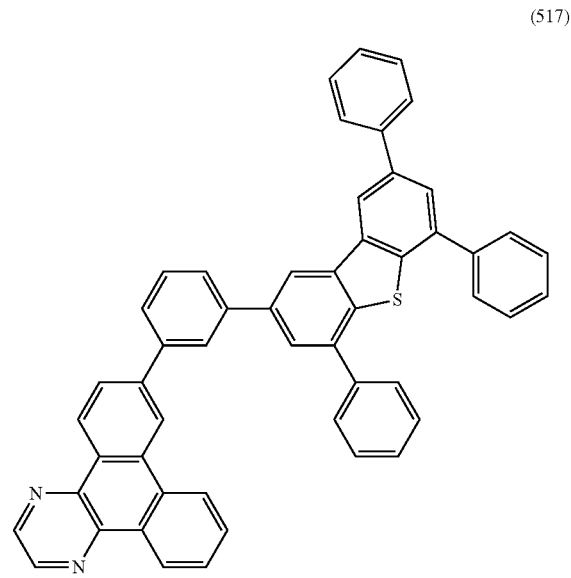

(518)
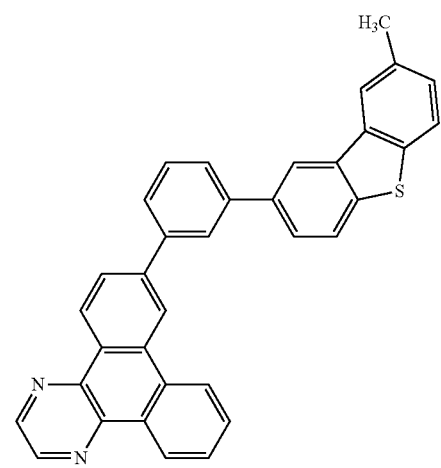
(519)
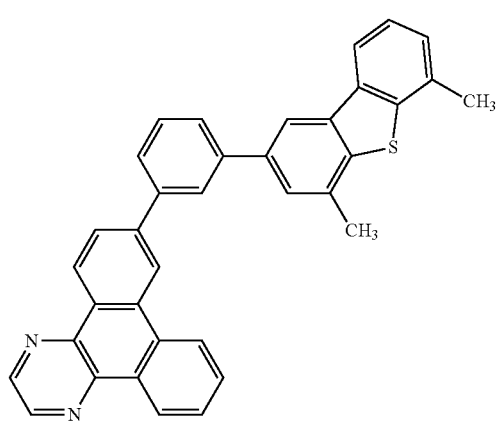
(520)
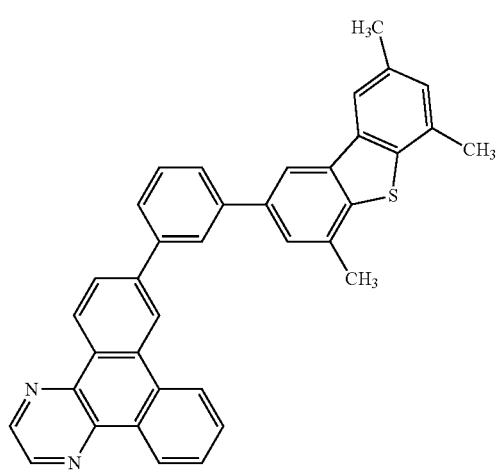
(521)
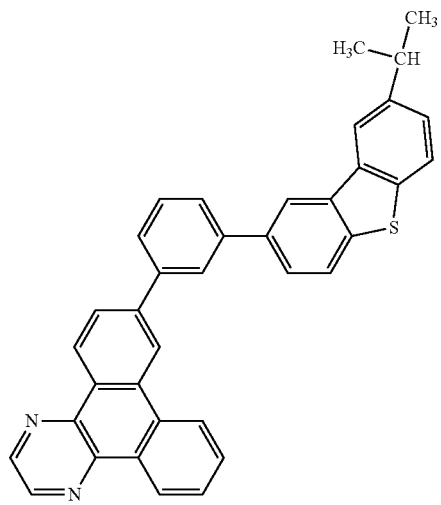
(522)
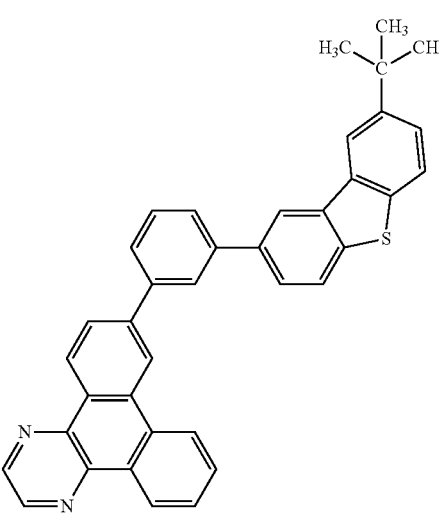
(523)
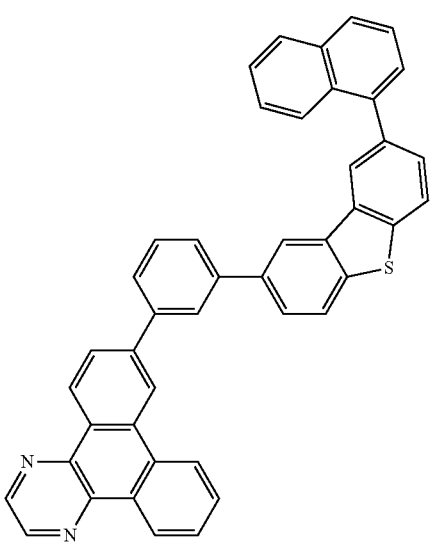

[Chemical Formula 47]
(524)
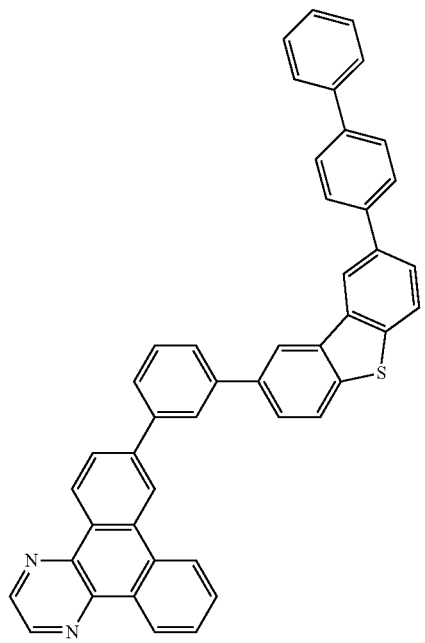
(525)
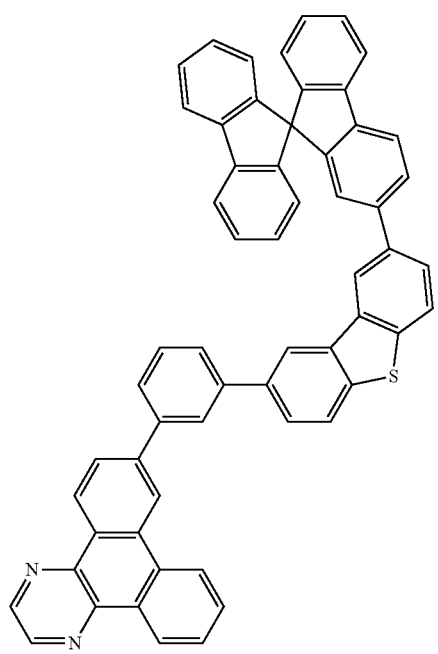
(526)
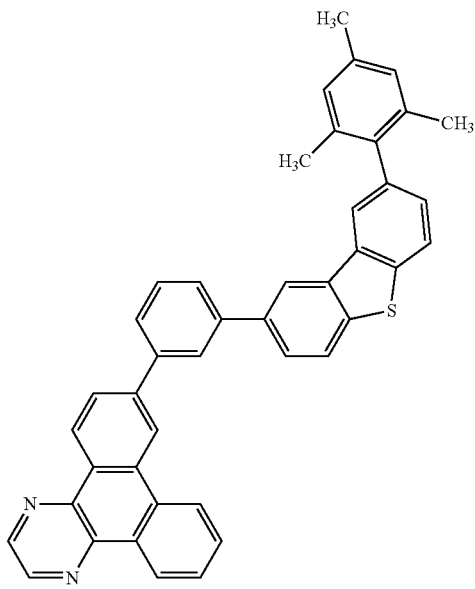
(527)
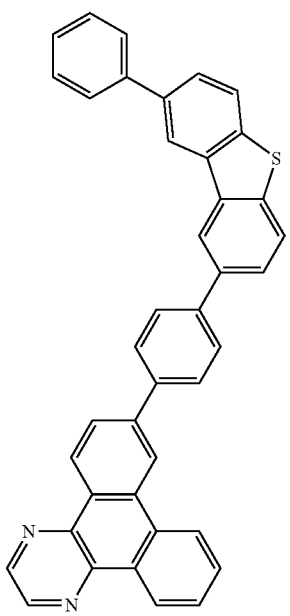

(528)
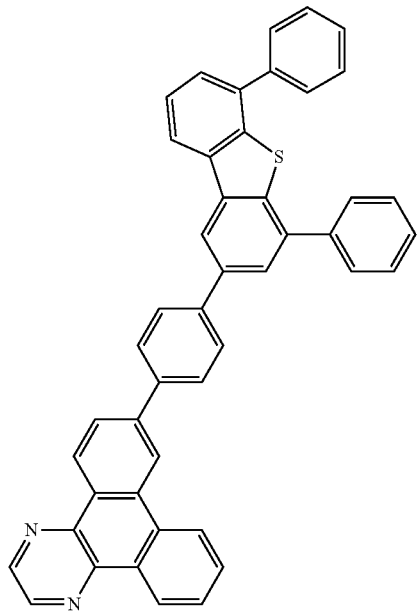
(529)
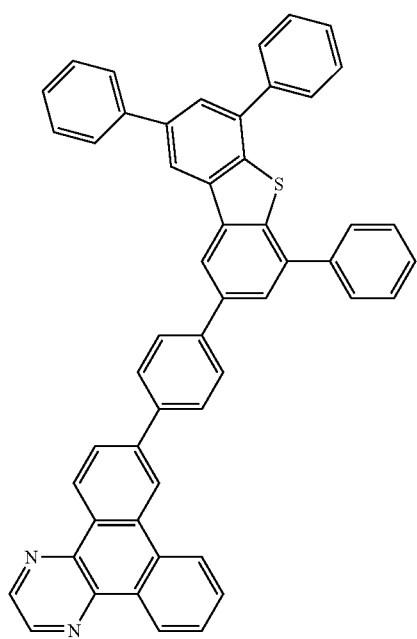
(530)
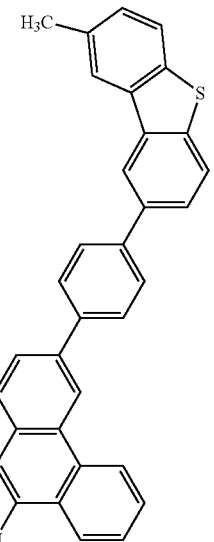
(531)
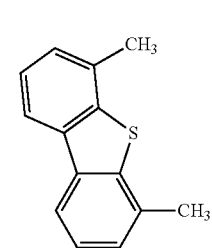
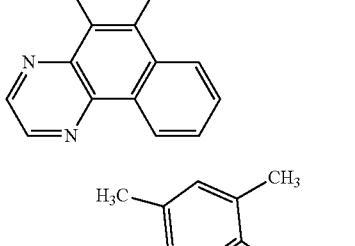
(532)
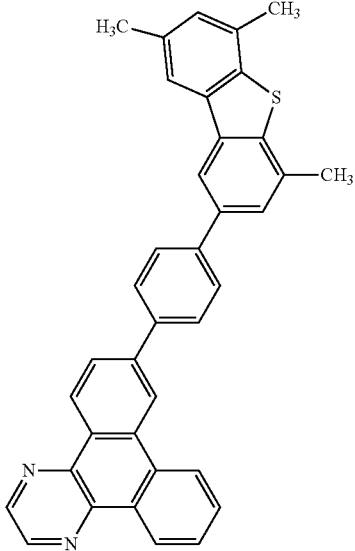

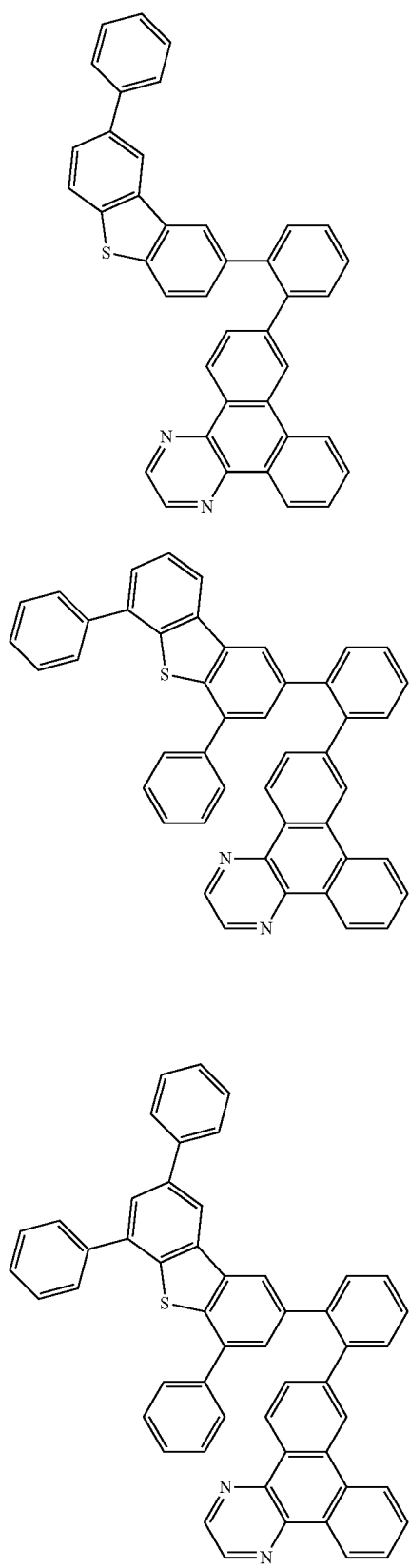
(533)
(534)
(535)
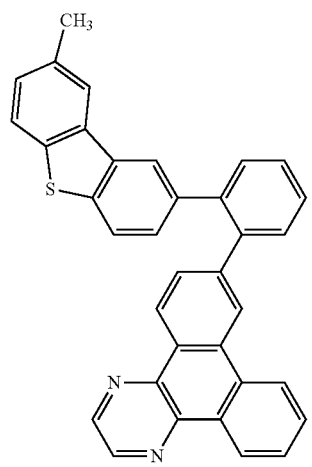
(536)
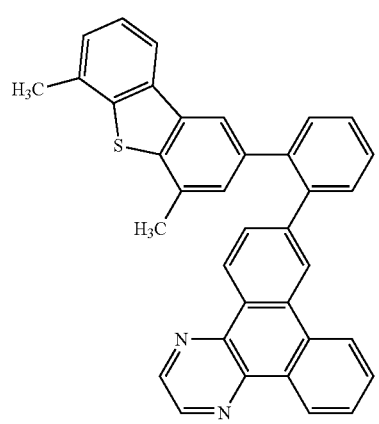
(537)
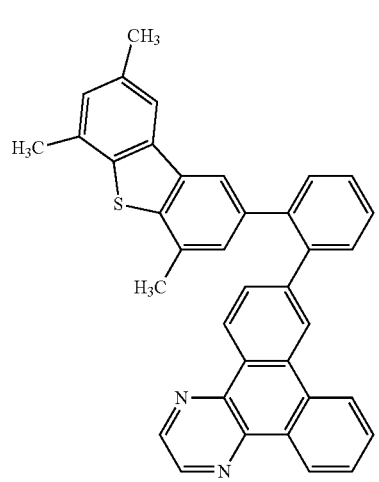
(538)

-continued
(539)
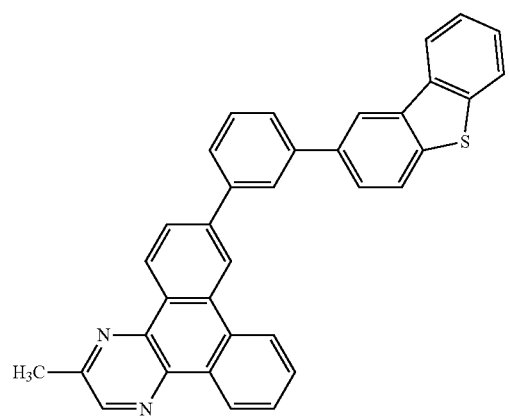
(540)
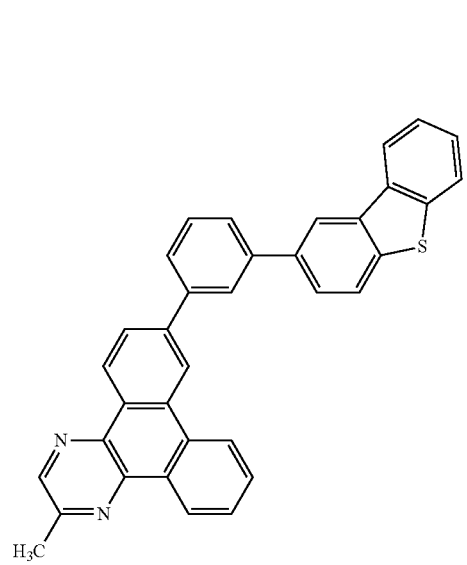
[Chemical Formula 49]
(541)
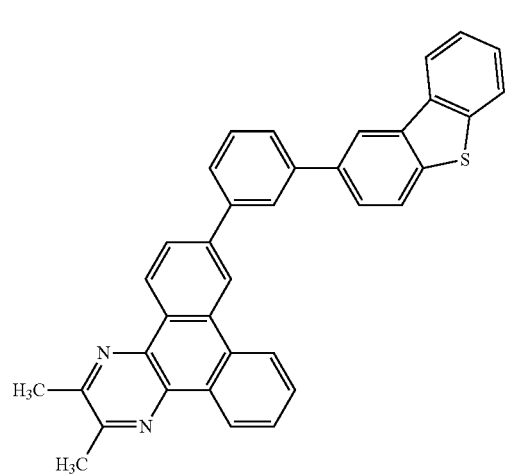
-continued
(542)
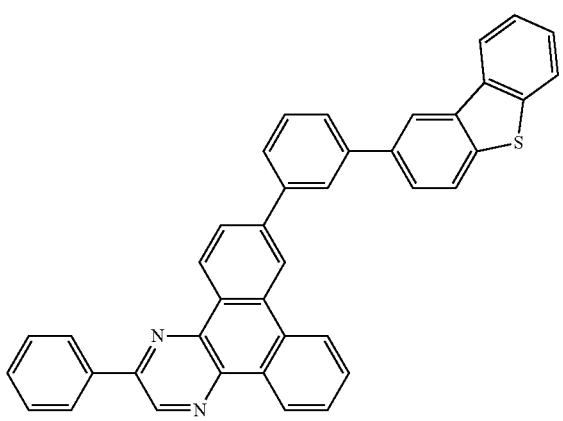
(543)
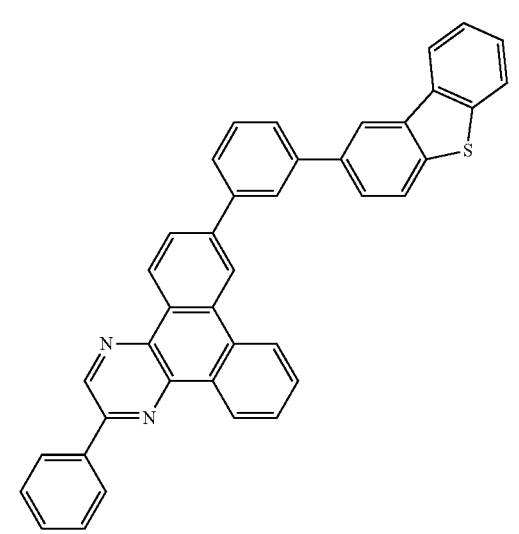
(544)
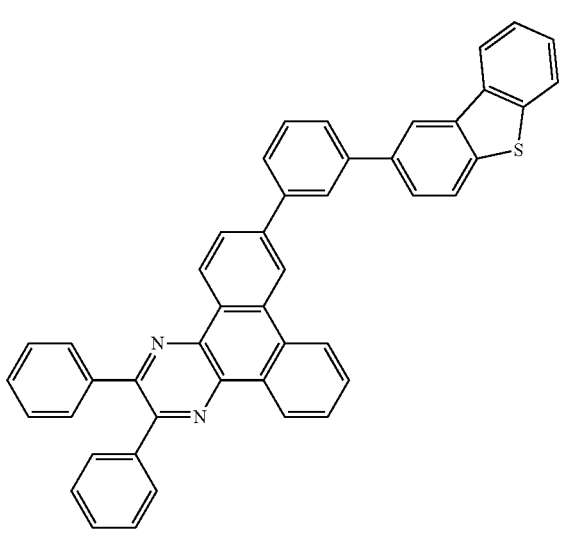

(545)
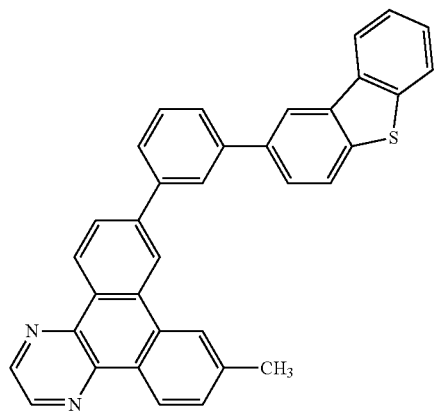
(546)
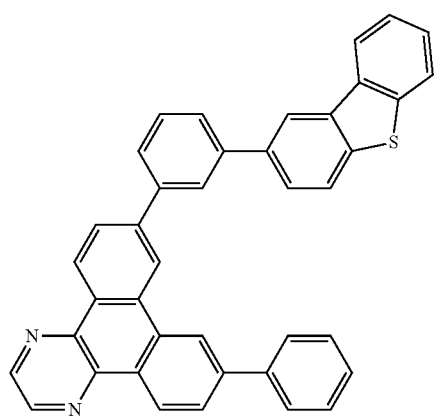
[Chemical Formula 50]
(600)
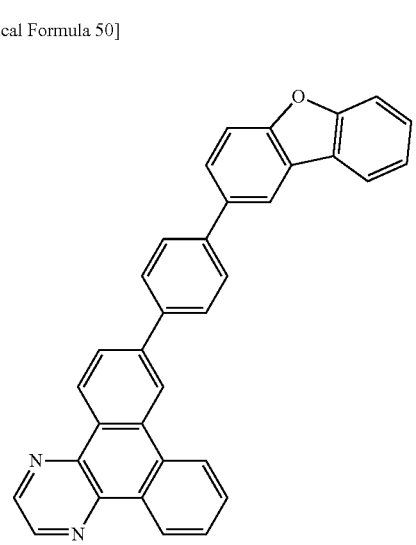
(601)
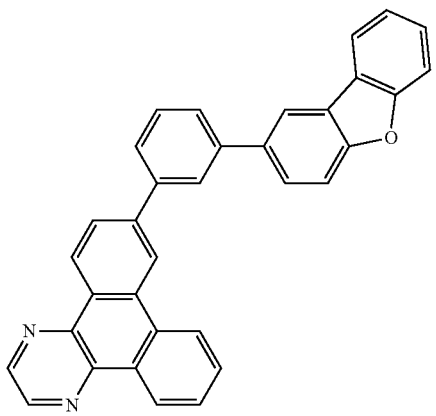
(602)
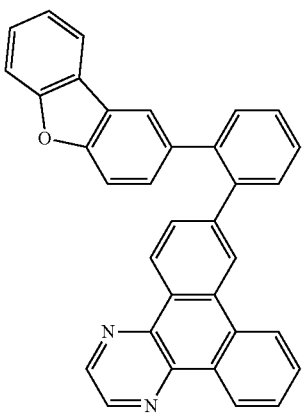
(603)
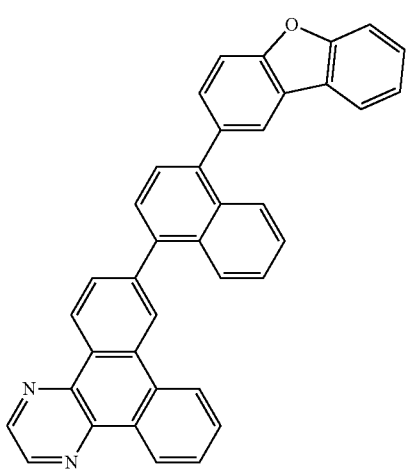

(604)
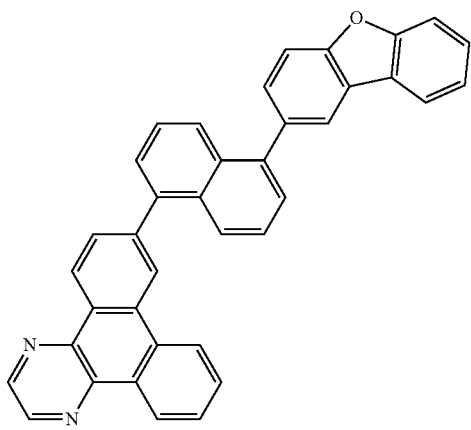
(605)
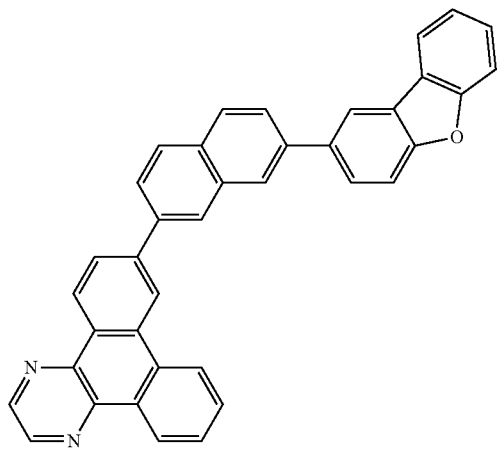
(606)
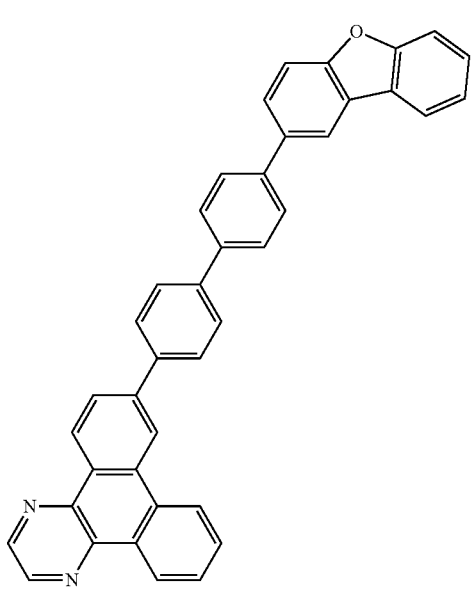
(607)
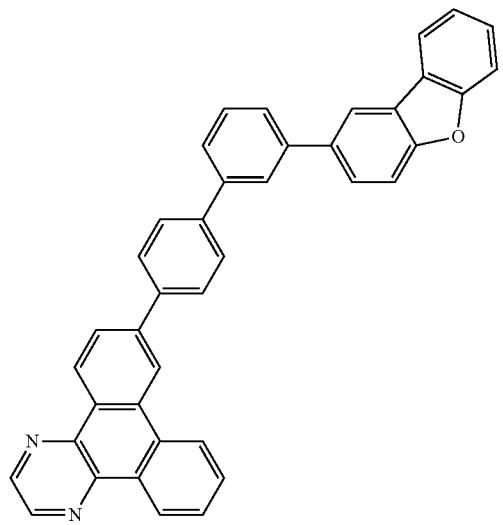
(608)
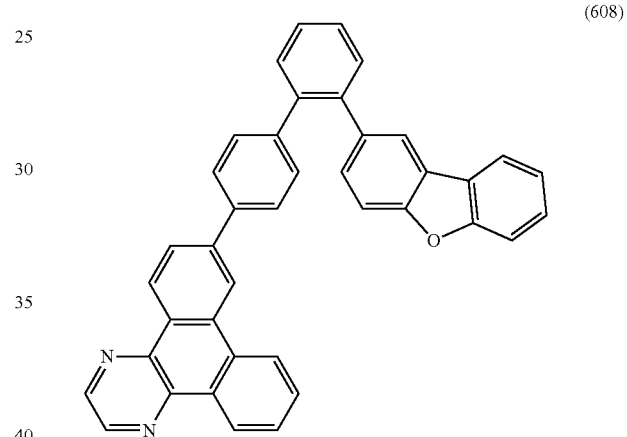
[Chemical Formula 51]
(609)
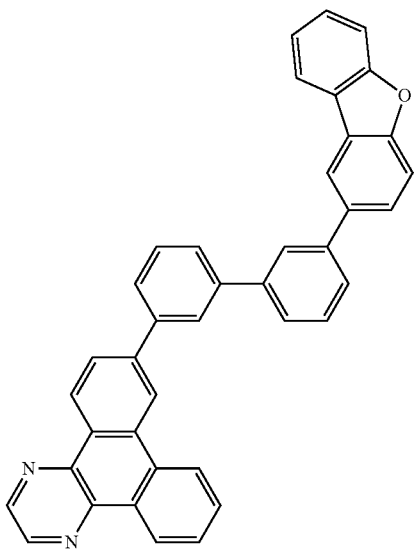

(610)
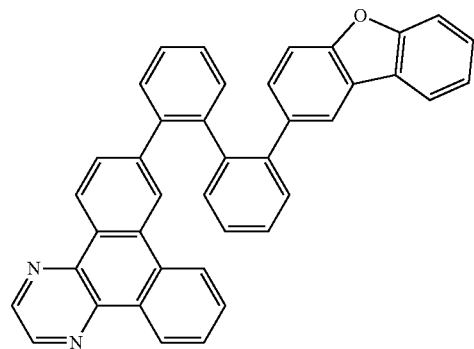
(611)
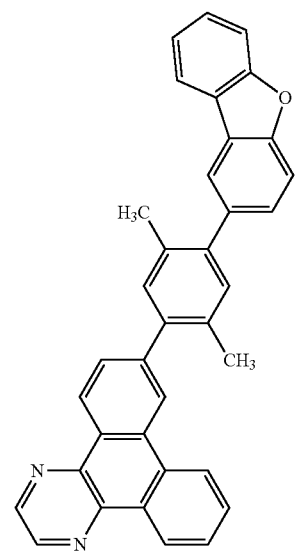
(612)
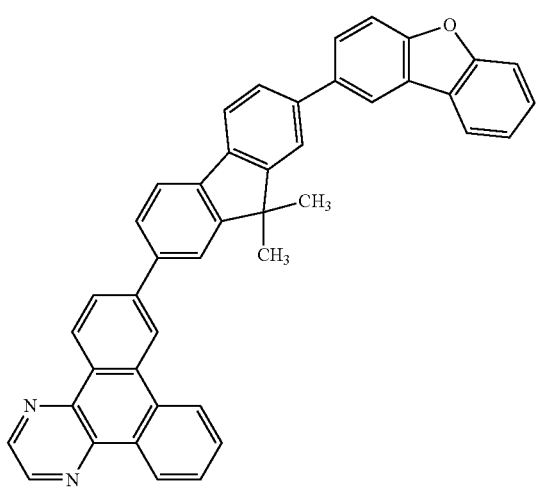
(613)
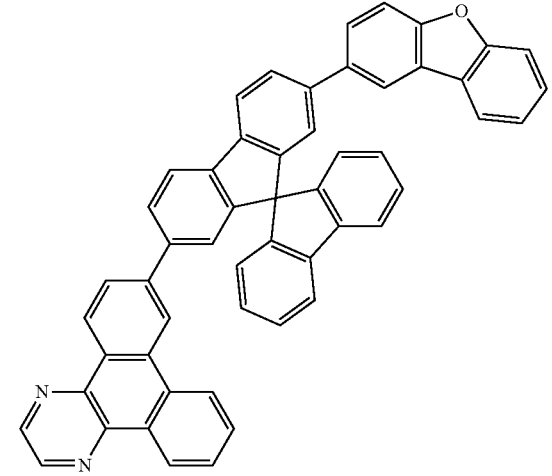
(614)
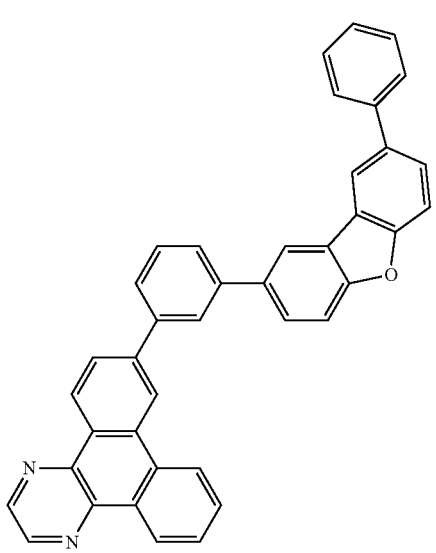
(615)
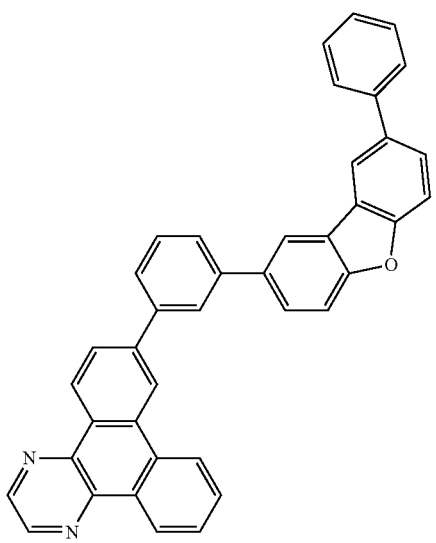

[Chemical Formula 52]
(616)
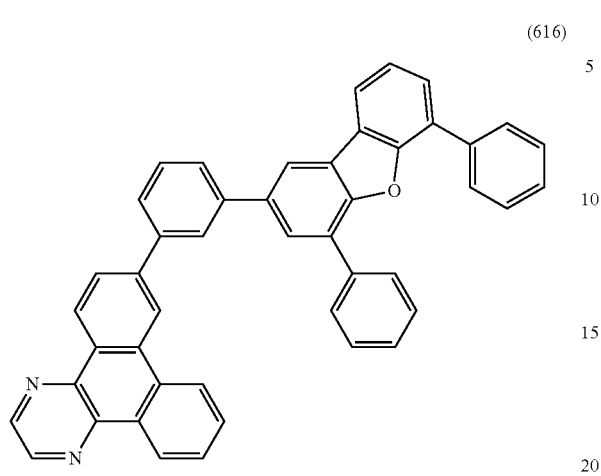
(617)
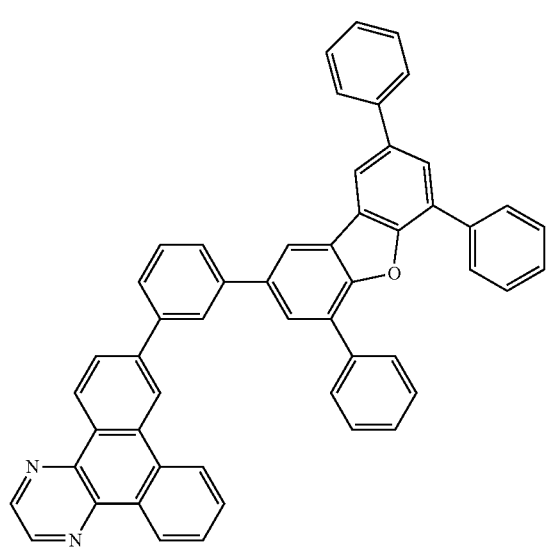
(618)
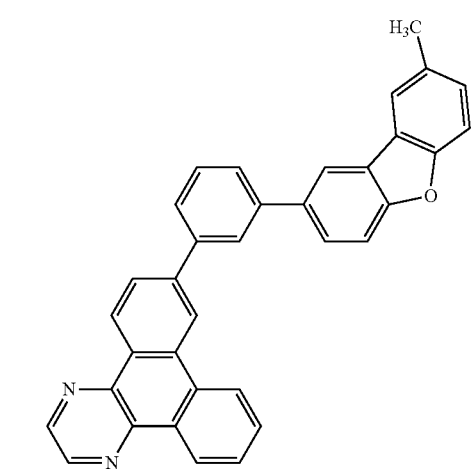
(619)
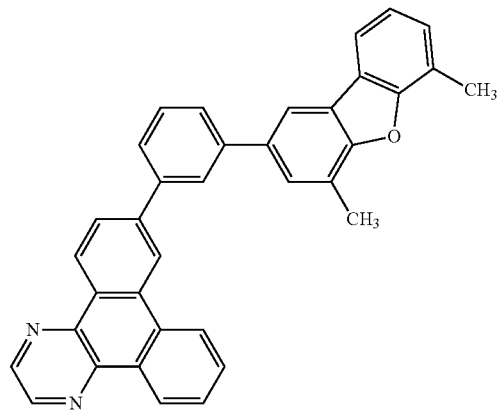
(620)
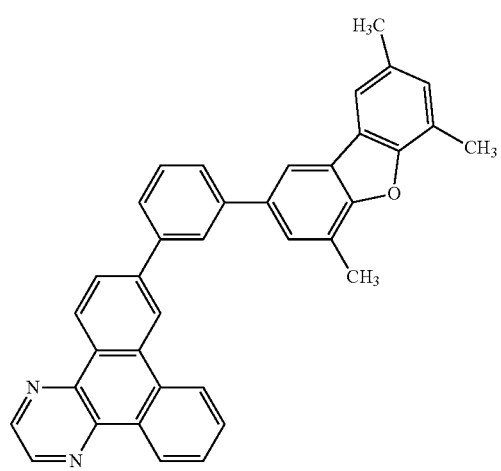
(621)
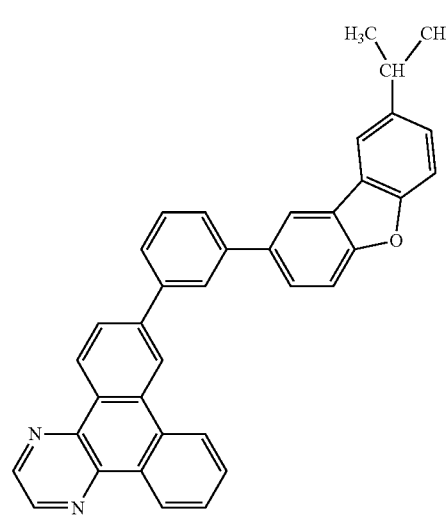

(622)
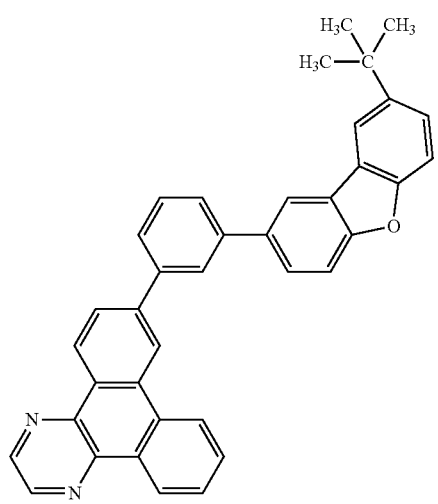
(623)
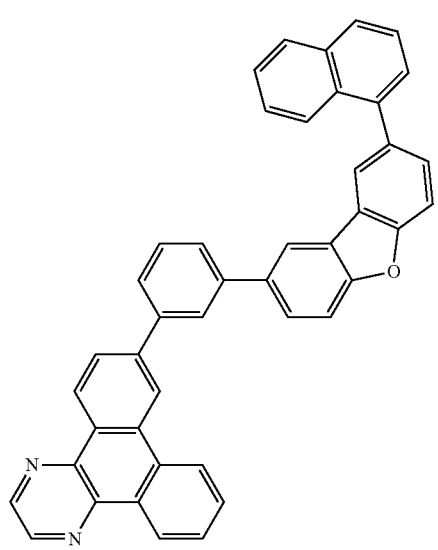
[Chemical Formula 53]
(624)
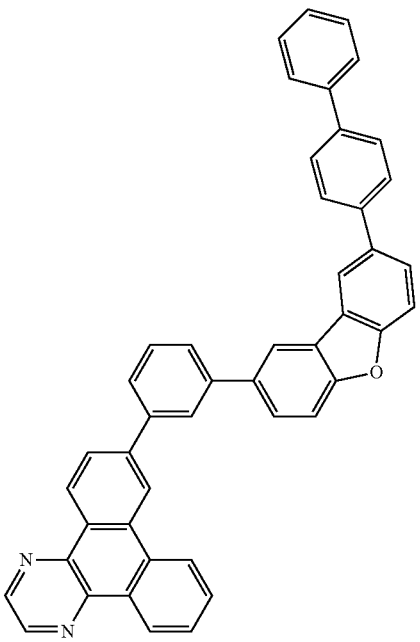
(625)
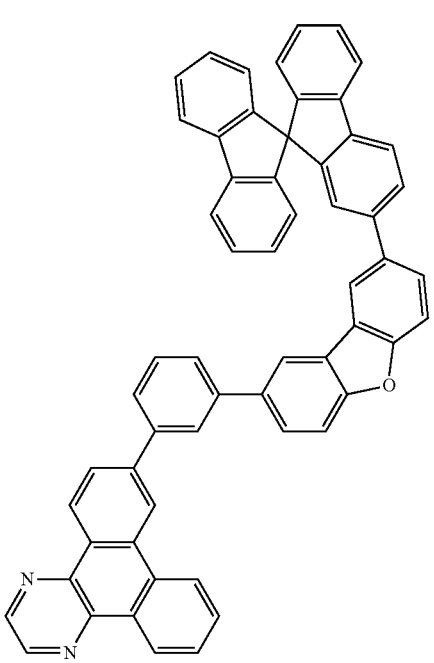

(626)
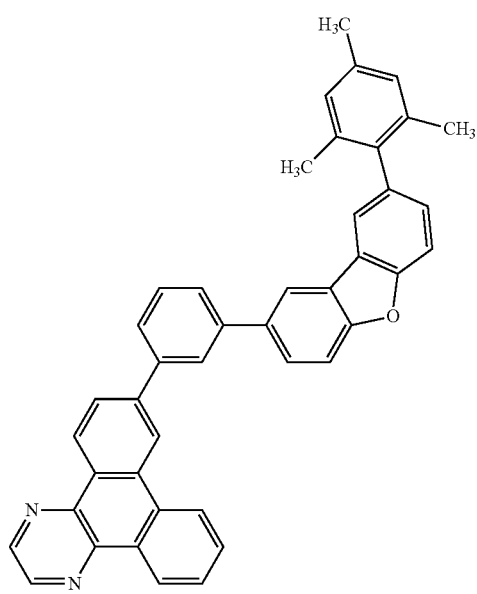
(627)
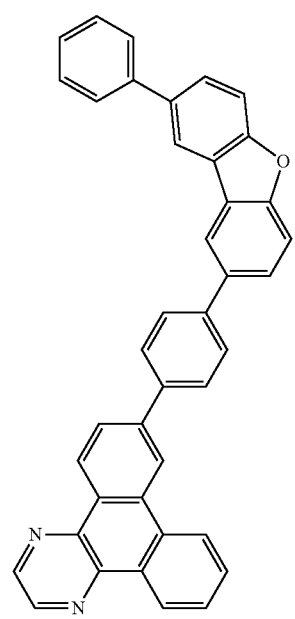
(628)
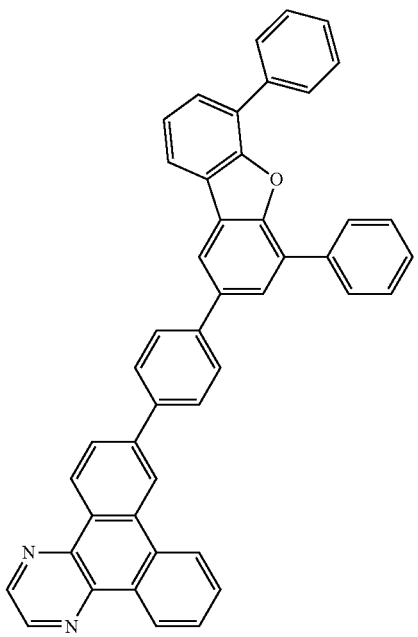
(629)
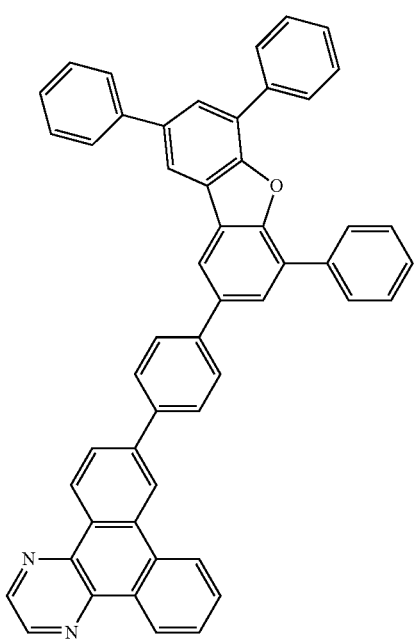

[Chemical Formula 54]
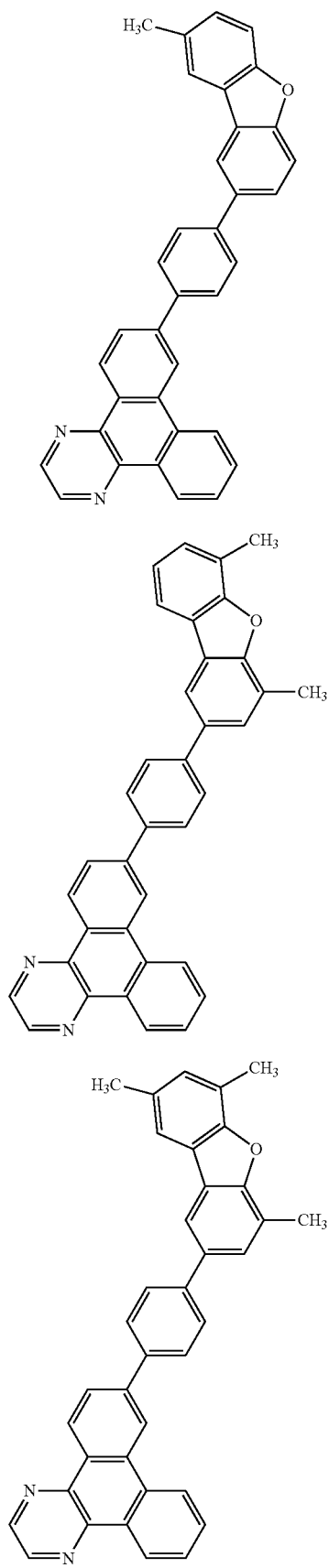
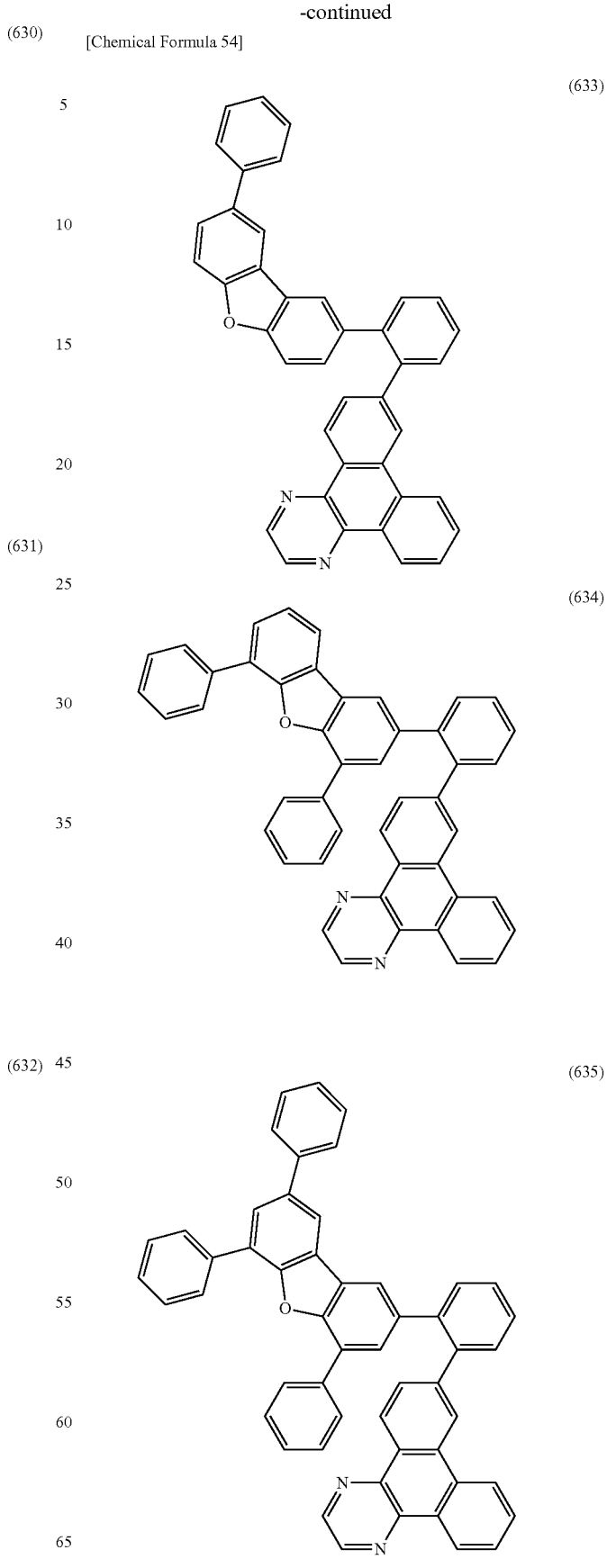

(636)
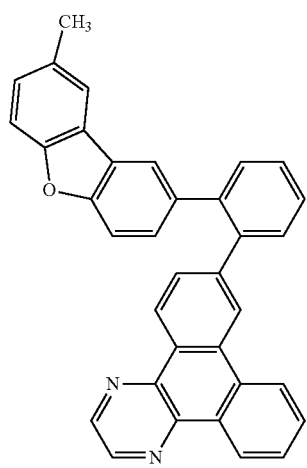
(637)
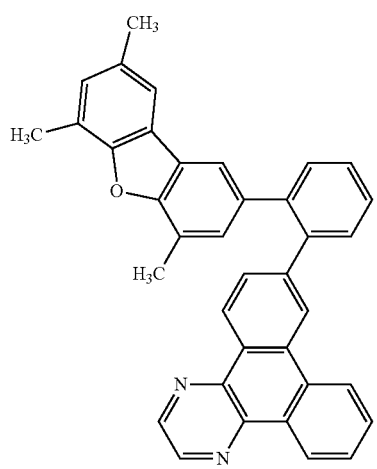
(638)
(639)
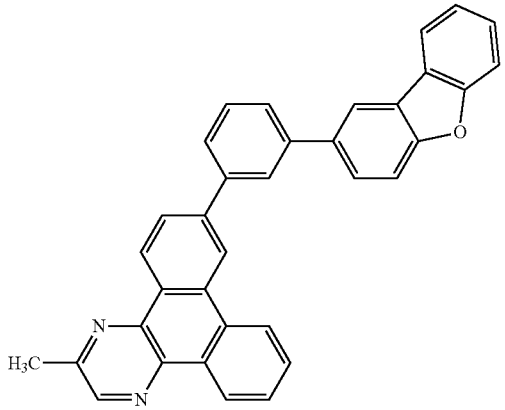
(640)
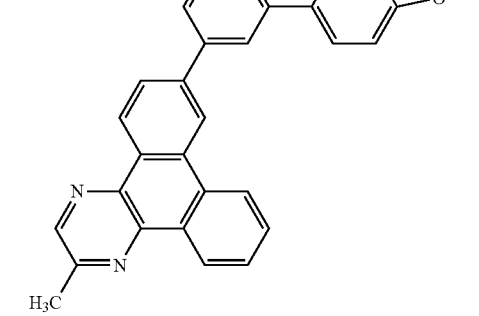
[Chemical Formula 55]
(641)
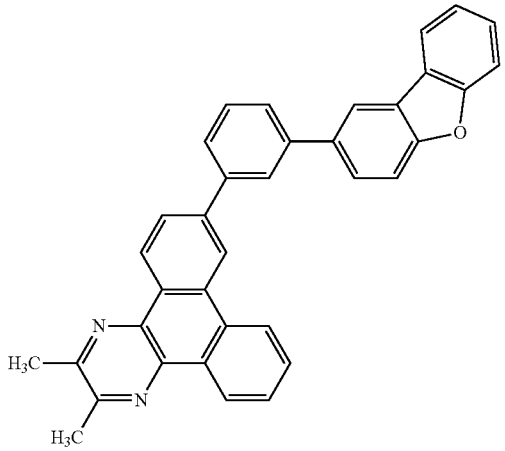

-continued (642)
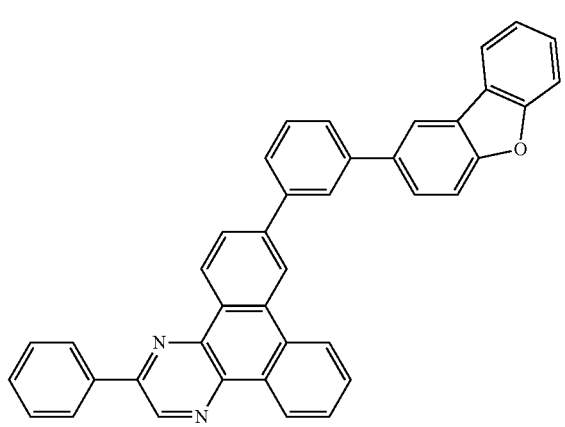

(643)
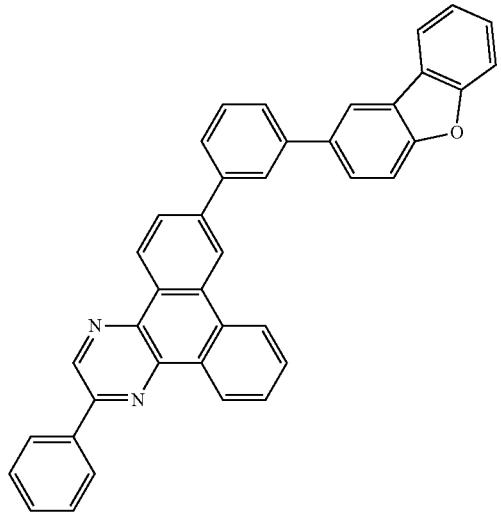

(644)
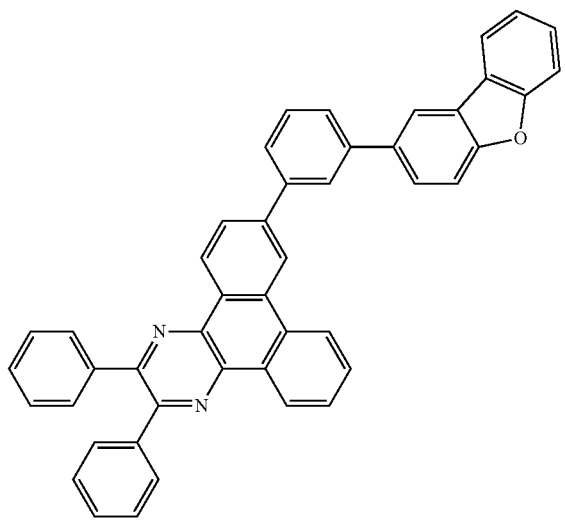

-continued (645)
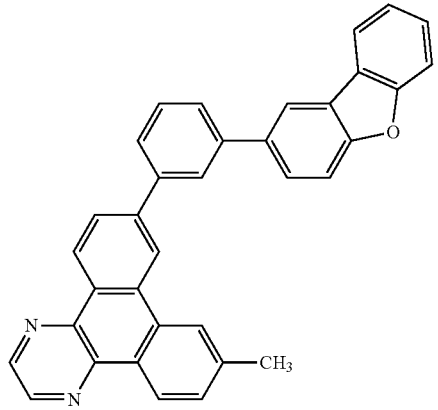

(646)
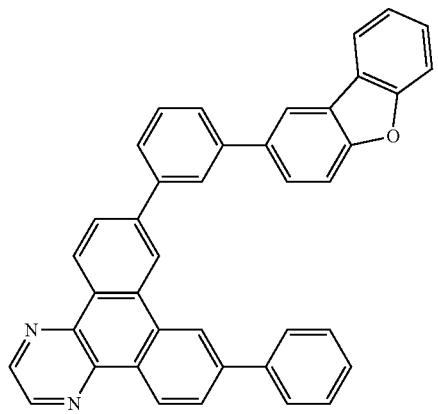

A variety of reactions can be applied to the method of synthesizing the heterocyclic compounds according to one embodiment of the present invention. For example, synthesis reactions described below enable the synthesis of the heterocyclic compound according to one embodiment of the present invention which is represented by the general formula (G1). Note that the method of synthesizing the heterocyclic compounds according to one embodiment of the present invention is not limited to the following synthesis methods.

[Synthesis Method 1 of Heterocyclic Compound Represented by General Formula (G1)]

First, a synthesis scheme (A-1) is illustrated below.

(A-1)

[Chemical Formula 56]

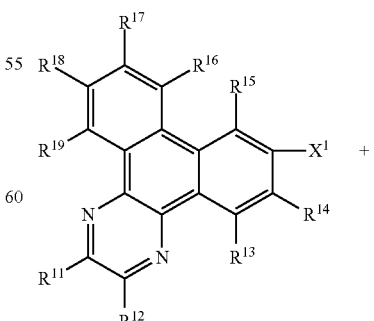

Compound 1

-continued

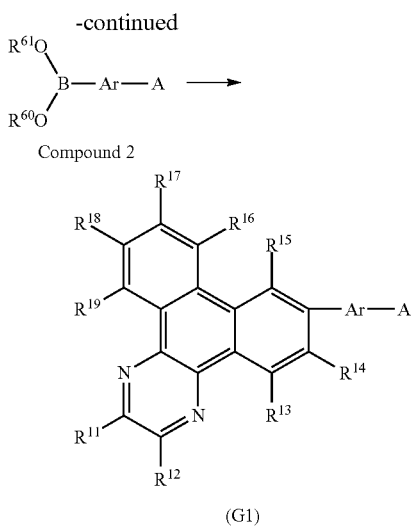

Compound 2

(G1)

The heterocyclic compound (G1) according to one embodiment of the present invention can be synthesized as illustrated in the synthesis scheme (A-1). Specifically, a halide of a dibenzo[f,h]quinoxaline derivative (compound 1) is subjected to coupling with boronic acid or an organoboron compound of a dibenzothiophene derivative, a dibenzofuran derivative, or a carbazole derivative (compound 2) using a Suzuki-Miyaura reaction, so that the heterocyclic compound (G1) described in this embodiment can be obtained.

In the synthesis scheme (A-1), A represents any of a substituted or unsubstituted dibenzothiophenyl group, a substituted or unsubstituted dibenzofuranyl group, and a substituted or unsubstituted carbazolyl group. Further, Ar represents an arylene group having 6 to 13 carbon atoms. The arylene group may have one or more substituents, and the substituents may be bonded to form a ring. Furthermore, $R^{11}$ to $R^{19}$ separately represent any of hydrogen, an alkyl group having 1 to 4 carbon atoms, and a substituted or unsubstituted aryl group having 6 to 13 carbon atoms. In addition, $R^{60}$ and $R^{61}$ separately represent hydrogen or an alkyl group having 1 to 6 carbon atoms. In the synthesis scheme (A-1), $R^{60}$ and $R^{61}$ may be bonded to each other to form a ring. Further, $X^1$ represents a halogen.

Examples of the palladium catalyst that can be used in the synthesis scheme (A-1) are, but not limited to, palladium(II) acetate, tetrakis(triphenylphosphine)palladium(0), bis(triphenylphosphine)palladium(II) dichloride, and the like.

Examples of the ligand of the palladium catalyst which can be used in the synthesis scheme (A-1) are, but not limited to, tri(ortho-tolyl)phosphine, triphenylphosphine, tricyclohexylphosphine, and the like.

Examples of the base that can be used in the synthesis scheme (A-1) are, but not limited to, organic bases such as sodium tert-butoxide, inorganic bases such as potassium carbonate and sodium carbonate, and the like.

Examples of the solvent that can be used in the synthesis scheme (A-1) are, but not limited to, the following: a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like. It is preferable to use a mixed solvent of toluene and water, a mixed solvent of toluene, ethanol, and water, or a mixed solvent of water and an ether such as ethylene glycol dimethyl ether.

As a coupling reaction illustrated in the synthesis scheme (A-1), the Suzuki-Miyaura reaction using the organoboron compound or boronic acid represented by the compound 2 may be replaced with a cross coupling reaction using an organoaluminum compound, an organozirconium compound, an organozinc compound, an organotin compound, or the like. However, the present invention is not limited thereto.

Further, in the Suzuki-Miyaura Coupling Reaction illustrated in the synthesis scheme (A-1), an organoboron compound or boronic acid of a dibenzo[f,h]quinoxaline derivative may be subjected to coupling with a halide of a dibenzothiophene derivative, a dibenzofuran derivative, or a carbazole derivative or with a dibenzothiophene derivative, a dibenzofuran derivative, or a carbazole derivative which has a triflate group as a substituent, using the Suzuki-Miyaura reaction.

Thus, a heterocyclic compound of this embodiment can be synthesized.

[Synthesis Method 2 of Heterocyclic Compound Represented by General Formula (G1)]

Another method of synthesizing the heterocyclic compound represented by the general formula (G1) is described below. First, a synthesis scheme (B-1) in which a boron compound of A is used for a material is illustrated below.

(B-1)

[Chemical Formula 57]

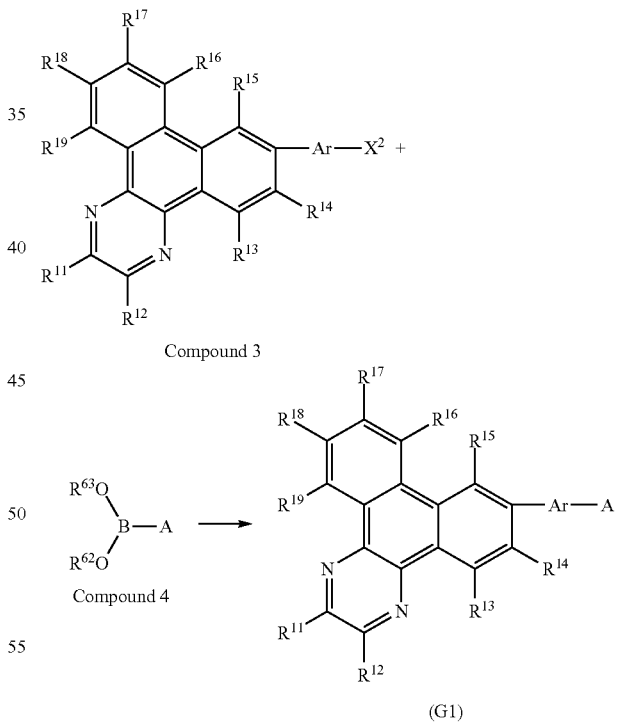

Compound 3

Compound 4

(G1)

As illustrated in the synthesis scheme (B-1), a halide of a dibenzo[f,h]quinoxaline derivative (compound 3) is subjected to coupling with an organoboron compound or boronic acid of a dibenzothiophene derivative, a dibenzofuran derivative, or a carbazole derivative (compound 4) using a Suzuki-Miyaura reaction, so that the heterocyclic compound (G1) described in this embodiment can be obtained.

In the synthesis scheme (B-1), A represents any of a substituted or unsubstituted carbazolyl group, a substituted or unsubstituted dibenzothiophenyl group, and a substituted or unsubstituted dibenzofuranyl group. Further, Ar represents an arylene group having 6 to 13 carbon atoms. The arylene group may have one or more substituents, and the substituents may be bonded to form a ring. Furthermore, $R^{11}$ to $R^{19}$ separately represent any of hydrogen, an alkyl group having 1 to 4 carbon atoms, and a substituted or unsubstituted aryl group having 6 to 13 carbon atoms. In addition, $R^{62}$ and $R^{63}$ separately represent hydrogen or an alkyl group having 1 to 6 carbon atoms. In the synthesis scheme (B-1), $R^{62}$ and $R^{63}$ may be bonded to each other to form a ring. Further, $X^2$ represents a halogen or a triflate group, and, as the halogen, preferably iodine or bromine.

Examples of the palladium catalyst that can be used in the synthesis scheme (B-1) are, but not limited to, palladium(II) acetate, tetrakis(triphenylphosphine)palladium(0), bis(triphenylphosphine)palladium(II) dichloride, and the like.

Examples of the ligand of the palladium catalyst which can be used in the synthesis scheme (B-1) are, but not limited to, tri(ortho-tolyl)phosphine, triphenylphosphine, tricyclohexylphosphine, and the like.

Examples of the base that can be used in the synthesis scheme (B-1) are, but not limited to, organic bases such as sodium tert-butoxide, inorganic bases such as potassium carbonate and sodium carbonate, and the like.

Examples of the solvent that can be used in the synthesis scheme (B-1) are, but not limited to, the following: a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like. It is preferable to use a mixed solvent of toluene and water, a mixed solvent of toluene, ethanol, and water, or a mixed solvent of water and an ether such as ethylene glycol dimethyl ether.

As a coupling reaction illustrated in the synthesis scheme (B-1), the Suzuki-Miyaura reaction using the organoboron compound or boronic acid represented by Compound 4 may be replaced with a cross coupling reaction using an organoaluminum compound, an organozirconium compound, an organozinc compound, an organotin compound, or the like. However, the present invention is not limited thereto. Further, in this coupling, a triflate group or the like may be used other than a halogen; however, the present invention is not limited thereto.

Further, in the Suzuki-Miyaura Coupling Reaction illustrated in the synthesis scheme (B-1), an organoboron compound or boronic acid of a dibenzo[f,h]quinoxaline derivative may be subjected to coupling with a halide of a dibenzothiophene derivative, a dibenzofuran derivative, or a carbazole derivative or with a dibenzothiophene derivative, a dibenzofuran derivative, or a carbazole derivative which has a triflate group as a substituent, using the Suzuki-Miyaura reaction.

When the heterocyclic compound represented by the general formula (G1) in which A is a substituted or unsubstituted N-carbazolyl group is synthesized, the synthesis is performed according to a synthesis scheme (B-2) below, so that the heterocyclic compound represented by the general formula (G2-2) can be obtained.

[Chemical Formula 58]

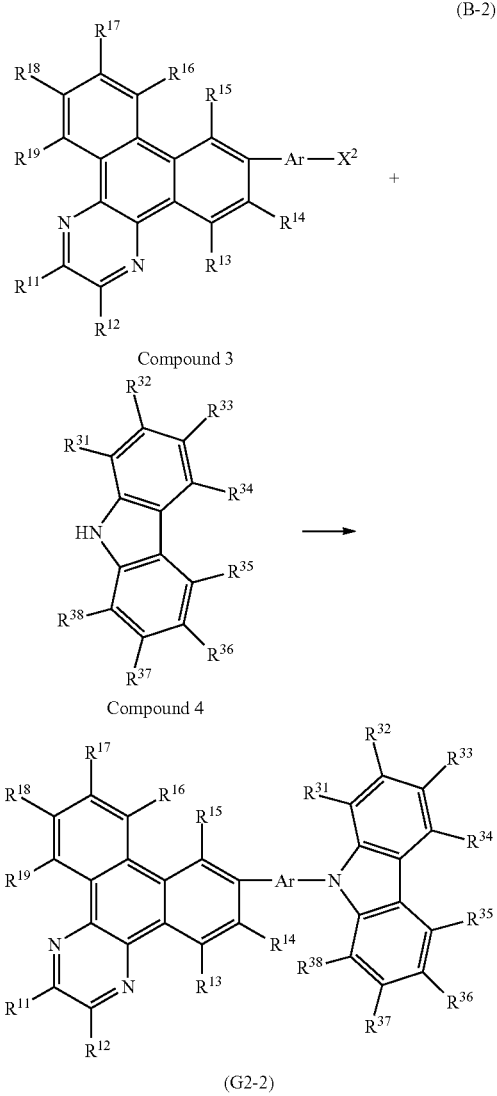

As illustrated in the synthesis scheme (B-2), the halide of a dibenzo[f,h]quinoxaline derivative (compound 3) a 9H-carbazole derivative (compound 5) are subjected to coupling using a metal catalyst, metal, or a metal compound in the presence of a base, so that the heterocyclic compound (G2-2) described in this embodiment can be obtained.

In the synthesis scheme (B-2), $R^{11}$ to $R^{19}$ separately represent any of hydrogen, an alkyl group having 1 to 4 carbon atoms, and a substituted or unsubstituted aryl group having 6 to 13 carbon atoms. Further, Ar represents an arylene group having 6 to 13 carbon atoms. The arylene group may have one or more substituents, and the substituents may be bonded to form a ring. Furthermore, $R^{31}$ to $R^{38}$ separately represent any of hydrogen, an alkyl group having 1 to 4 carbon atoms, and a substituted or unsubstituted aryl group having 6 to 13 carbon atoms. Further, $X^3$ represents a halogen or a triflate group, and, as a halogen, preferably iodine or bromine.

In the case where the Hartwig-Buchwald reaction is performed in the synthesis scheme (B-2), bis(dibenzylideneacetone)palladium(0), palladium(II) acetate, or the like can be given as the palladium catalyst that can be used.

Examples of the ligand of the palladium catalyst which can be used in the synthesis scheme (B-2) include tri(tert-butyl)phosphine, tri(n-hexyl)phosphine, tricyclohexylphosphine, and the like.

Examples of the base that can be used in the synthesis scheme (B-2) include organic bases such as sodium tert-butoxide, inorganic bases such as potassium carbonate, and the like.

Examples of the solvent that can be used in the synthesis scheme (B-2) include toluene, xylene, benzene, tetrahydrofuran, and the like.

Other than the Hartwig-Buchwald reaction, the Ullmann reaction or the like may be used, and the reaction that can be used is not limited to these.

Thus, the heterocyclic compound of this embodiment can be synthesized.

Since the heterocyclic compounds of this embodiment have a wide energy gap, high current efficiency can be obtained by use of any of the heterocyclic compounds for a light-emitting element as a host material of a light-emitting layer in which a light-emitting substance is dispersed. In particular, the heterocyclic compounds of this embodiment are suitable for a host material in which a phosphorescent compound is dispersed. Further, since the heterocyclic compounds of this embodiment are substances having a high electron-transport property, any of the heterocyclic compounds can be suitably used for a material of an electron-transport layer in a light-emitting element. By use of any of the heterocyclic compounds of this embodiment, it is possible to realize a light-emitting element having low driving voltage, a light-emitting element having high current efficiency, or a light-emitting element having a long lifetime. Furthermore, by use of this light-emitting element, a light-emitting device, an electronic device, and a lighting device each having reduced power consumption can be obtained.

Embodiment 2

In this embodiment, as one mode of the present invention, a light-emitting element in which any of the heterocyclic compounds described in Embodiment 1 is used for a light-emitting layer is described with reference to FIGS. 1A to 1C.

A light-emitting element having an EL layer 102 between a first electrode 103 and a second electrode 108 is illustrated in FIG. 1A. The light-emitting element illustrated in FIG. 1A includes a hole-injection layer 701, a hole-transport layer 702, a light-emitting layer 703, an electron-transport layer 704, and an electron-injection layer 705 which are stacked in this order over the first electrode 103, and the second electrode 108 provided over the layers. The light-emitting layer 703 includes any of the heterocyclic compounds according to one embodiment of the present invention which are described in Embodiment 1.

For the first electrode 103, any of metals, alloys, electrically conductive compounds, mixtures thereof, and the like which has a high work function (specifically, 4.0 eV or more) is preferably used. Specific examples are indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide (IWZO), and the like. Films of these conductive metal oxides are usually formed by sputtering, but may be formed by application of a sol-gel method or the like. For example, a film of indium oxide-zinc oxide can be formed by a sputtering method using a target obtained by addition of 1 wt % to 20 wt % of zinc oxide to indium oxide. Further, an IWZO film can be formed by a sputtering method using a target obtained by addition of 0.5 wt % to 5 wt % of tungsten oxide and 0.1 wt % to 1 wt % of zinc oxide to indium oxide. Other examples are graphene, gold, platinum, nickel, tungsten, chromium, molybdenum, iron, cobalt, copper, palladium, nitrides of metal materials (e.g. titanium nitride), and the like.

However, when a layer which is in contact with the first electrode 103 and included in the EL layer 102 is formed using a composite material described later in which an organic compound and an electron acceptor (acceptor) are mixed, as a substance used for the first electrode 103, any of a variety of metals, alloys, and electrically conductive compounds, a mixture thereof, and the like can be used regardless of work function. For example, aluminum, silver, an alloy containing aluminum (e.g. Al—Si), or the like can also be used.

The first electrode 103 can be formed by, for example, a sputtering method, an evaporation method (including a vacuum evaporation method), or the like.

For the second electrode 108, any of metals, alloys, electrically conductive compounds, mixtures thereof, and the like which has a low work function (preferably, 3.8 eV or less) is preferably used. Specifically, in addition to elements that belong to Group 1 or Group 2 in the periodic table, that is, alkali metals such as lithium and cesium, alkaline earth metals such as calcium and strontium, magnesium, alloys thereof (e.g. Mg—Ag and Al—Li), rare earth metals such as europium and ytterbium, and alloys thereof, aluminum, silver, or the like can be used.

When a composite material described later in which an organic compound and an electron donor (donor) is used for a layer included in the EL layer 102 which is formed in contact with the second electrode 108, a variety of conductive materials such as Al, Ag, ITO, and indium oxide-tin oxide containing silicon or silicon oxide can be used regardless of work function.

When the second electrode 108 is formed, a vacuum evaporation method or a sputtering method can be used. When a silver paste or the like is used, a coating method, an inkjet method, or the like can be used.

The EL layer 102 has at least the light-emitting layer 703, which is formed so as to include any of the heterocyclic compounds according to one embodiment of the present invention. A known substance can also be used for a part of the EL layer 102, and either a low molecular compound or a high molecular compound can be used. Note that a substance included in the EL layer 102 is not limited to an organic compound, and may be a structure in which an inorganic compound is included as a part.

As illustrated in FIG. 1A, the EL layer 102 is formed in such a way that, in addition to the light-emitting layer 703, the hole-injection layer 701 which includes a substance having a high hole-injection property, the hole-transport layer 702 which includes a substance having a high hole-transport property, the electron-transport layer 704 which includes a substance having a high electron-transport property, the electron-injection layer 705 which includes a substance having a high electron-injection property, and the like are combined and stacked as appropriate.

The hole-injection layer 701 is a layer that includes a substance having a high hole-injection property. As the substance having a high hole-injection property, a metal oxide such as molybdenum oxide, titanium oxide, vanadium oxide, rhenium oxide, ruthenium oxide, chromium oxide, zirconium oxide, hafnium oxide, tantalum oxide, silver oxide, tungsten oxide, or manganese oxide can be used. A phthalocyanine-based compound such as phthalocyanine (abbreviation: H₂Pc), or copper(II) phthalocyanine (abbreviation: CuPc) can also be used.

Any of the following aromatic amine compounds which are low molecular organic compounds can also be used: 4,4',4"-tris(N,N'-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

A high molecular compound (e.g. an oligomer, a dendrimer, or a polymer) can also be used. Examples are high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). A high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can also be used.

For the hole-injection layer 701, the composite material in which an organic compound and an electron acceptor (acceptor) are mixed may be used. Such a composite material is excellent in a hole-injection property and a hole-transport property because the electron acceptor causes hole generation in the organic compound. In this case, the organic compound is preferably a material excellent in transporting the generated holes (a substance having a high hole-transport property).

As the organic compound used for the composite material, any of a variety of compounds such as aromatic amine compounds, carbazole derivatives, aromatic hydrocarbons, and high molecular compounds (e.g. oligomers, dendrimers, and polymers) can be used. The organic compound used for the composite material is preferably an organic compound having a high hole-transport property. Specifically, a substance having a hole mobility of $10^{-6}$ cm²/Vs or more is preferably used. Note that other than these substances, a substance that has a property of transporting more holes than electrons may be used. The organic compounds which can be used for the composite material are specifically given below.

Examples of the organic compounds that can be used for the composite material include the following: aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP); and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)phenyl]-10-phenylanthracene (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl]-2,3,5,6-tetraphenylbenzene.

Any of the following aromatic hydrocarbon compounds can be used: 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, and 2,3,6,7-tetramethyl-9,10-di(1-naphthyl)anthracene.

Any of the following aromatic hydrocarbon compounds can be used: 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

Examples of the electron acceptor include organic compounds such as 7,7,8,8-tetracyano-2,3,5,6-tetrafluoroquinodimethane (abbreviation: F₄-TCNQ) and chloranil and transition metal oxides. Other examples include oxides of metals that belong to any of Groups 4 to 8 in the periodic table. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide, which is easy to handle owing to its stability in the air and low hygroscopic property, is particularly preferred.

The composite material may be formed using the above-described electron acceptor and the above-described high molecular compound such as PVK, PVTPA, PTPDMA, or Poly-TPD, and used for the hole-injection layer 701.

The hole-transport layer 702 is a layer that includes a substance having a high hole-transport property. Examples of the substance having a high hole-transport property include aromatic amine compounds such as NPB, TPD, BPAFLP, 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances mentioned here are mainly substances that have a hole mobility of $10^{-6}$ cm²/Vs or more. Note that other than these substances, a substance that has a property of transporting more holes than electrons may be used. Note that the layer that includes a substance having a high hole-transport property is not limited to a single layer, and may be a stack of two or more layers including any of the above substances.

For the hole-transport layer 702, a carbazole derivative such as CBP, CzPA, or PCzPA or an anthracene derivative such as t-BuDNA, DNA, or DPAnth may also be used.

For the hole-transport layer 702, a high molecular compound such as PVK, PVTPA, PTPDMA, or Poly-TPD can also be used.

The light-emitting layer 703 is a layer that includes a light-emitting substance. The light-emitting layer 703 of this embodiment includes any of the heterocyclic compounds according to one embodiment of the present invention. In the light-emitting layer in which a light-emitting substance (guest material) is dispersed in another substance (host material), the heterocyclic compound according to one embodiment of the present invention can be used for the host material. The guest material which is a light-emitting substance is dispersed in the heterocyclic compound according to one embodiment of the present invention, so that light emission from the guest material can be obtained.

In addition, a plurality of kinds of substances can be used as the substances (host materials) in which the light-emitting substance (guest material) is dispersed. The light-emitting layer may thus include another material as a host material in addition to the heterocyclic compound according to one embodiment of the present invention.

As the light-emitting substance, for example, a fluorescent compound which emits fluorescence or a phosphorescent compound which emits phosphorescence can be used. Examples of a fluorescent substance that can be used for the light-emitting layer 703 are the following light-emitting materials: materials that emit blue light, such as N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and 4-(10-phenyl-9-anthryl)-4'-(9-phenyl-9H-carbazol-3-yl) triphenylamine (abbreviation: PCBAPA); materials that emit green light, such as N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), and N,N,9-triphenylanthracen-9-amine (abbreviation: DPhAPhA); materials that emit yellow light, such as rubrene and 5,12-bis(1,1'-biphenyl-4-yl)-6,11-diphenyltetracene (abbreviation: BPT); and materials that emit red light, such as N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-a]fluoranthene-3,10-diamine (abbreviation: p-mPhAFD).

In addition, the phosphorescent compounds that can be used for the light-emitting layer 703 are the following light-emitting materials, for example: materials that emit green light, such as tris(2-phenylpyridinato-N,$C^{2'}$)iridium (III) (abbreviation: [Ir(ppy)$_3$]), bis(2-phenylpyridinato-N, $C^{2'}$)iridium(III)acetylacetonate (abbreviation: [Ir(ppy)$_2$(acac)]), bis(1,2-diphenyl-1H-benzimidazolato)iridium(III) acetylacetonate (abbreviation: [Ir(pbi)$_2$(acac)]), bis(benzo[h]quinolinato)iridium(III)acetylacetonate (abbreviation: [Ir(bzq)$_2$(acac)]), tris(benzo[h]quinolinato)iridium(III) (abbreviation: [Ir(bzq)$_3$]); materials that emit yellow light, such as bis(2,4-diphenyl-1,3-oxazolato-N,$C^{2'}$)iridium(III) acetylacetonate (abbreviation: [Ir(dpo)$_2$(acac)]), bis {2-[4'-(perfluorophenylphenyl)]pyridinato-N,$C^{2'}$}iridium(III) acetylacetonate (abbreviation: [Ir(p-PF-ph)$_2$(acac)]), bis(2-phenylbenzothiazolato-N,$C^{2'}$)iridium(III)acetylacetonate (abbreviation: [Ir(bt)$_2$(acac)]), (acetylacetonato)bis[2,3-bis(4-fluorophenyl)-5-methylpyrazinato]iridium (III) (abbreviation: [Ir(Fdppr-Me)$_2$(acac)]), and (acetylacetonato)bis[2-(4-methoxyphenyl)-3,5-dimethylpyrazinato]iridium(III) (abbreviation: [Ir(dmmoppr)$_2$(acac)]); materials that emit orange light, such as tris(2-phenylquinolinato-N,$C^{2'}$)iridium (III) (abbreviation: [Ir(pq)$_3$]), bis(2-phenylquinolinato-N, $C^{2'}$)iridium(III)acetylacetonate (abbreviation: [Ir(pq)$_2$(acac)]), (acetylacetonato)bis(3,5-dimethyl-2-phenylpyrazinato)iridium(III) (abbreviation: [Ir(mppr-Me)$_2$(acac)]), (acetylacetonato)bis(5-isopropyl-3-methyl-2-phenylpyrazinato)iridium(III) (abbreviation: [Ir(mppr-iPr)$_2$ (acac)]); and materials that emit red light, examples of which are organometallic complexes such as bis[2-(2'-benzo[4,5-α]thienyl)pyridinato-N,$C^{3'}$)iridium(III)acetylacetonate (abbreviation: [Ir(btp)$_2$(acac)]), bis(1-phenylisoquinolinato-N, $C^{2'}$)iridium(III)acetylacetonate (abbreviation: [Ir(piq)$_2$(acac)]), (acetylacetonato)bis[2,3-bis(4-fluorophenyl)quinoxalinato]iridium(III) (abbreviation: [Ir(Fdpq)$_2$(acac)]), (acetylacetonato)bis(2,3,5-triphenylpyrazinato)iridium(III) (abbreviation: [Ir(tppr)$_2$(acac)]), (dipivaloylmethanato)bis (2,3,5-triphenylpyrazinato)iridium(III) (abbreviation: [Ir(tppr)$_2$(dpm)]), and (2,3,7,8,12,13,17,18-octaethyl-21H, 23H-porphine)platinum(II) (abbreviation: PtOEP). As the phosphorescent compound, any of the following rare earth metal complexes can be used: tris(acetylacetonato)(monophenanthroline)terbium(III) (abbreviation: [Tb(acac)$_3$ (Phen)]), tris(1,3-diphenyl-1,3-propanedionato)(monophenanthroline)europium(III) (abbreviation: [Eu(DBM)$_3$ (Phen)]), and tris[1-(2-thenoyl)-3,3,3-trifluoroacetonato] (monophenanthroline)europium (III) (abbreviation: [Eu (TTA)$_3$(Phen)]), because their light emission is from the rare earth metal ion (electron transfer between different multiplicities) in such a rare earth metal complex.

As the light-emitting substance, a high molecular compound can be used. Specific examples are the following light-emitting materials: materials that emit blue light, such as poly(9,9-dioctylfluorene-2,7-diyl) (abbreviation: PFO), poly[(9,9-dioctylfluorene-2,7-diyl)-co-(2,5-dimethoxybenzene-1,4-diyl)] (abbreviation: PF-DMOP), and poly{(9,9-dioctylfluorene-2,7-diyl)-co-[N,N'-di-(p-butylphenyl)-1,4-diaminobenzene]} (abbreviation: TAB-PFH); materials that emit green light, such as poly(p-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), and poly[(9,9-dioctyl-2,7-divinylenefluorenylene)-alt-co-(2-methoxy-5-(2-ethylhexyloxy)-1,4-phenylene)]; and materials that emit orange to red light, such as poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{9,9-dihexyl-2,7-bis(1-cyanovinylene)fluorenylene]-alt-co-[2,5-bis(N,N'-diphenylamino)-1,4-phenylene]}, and poly{[2-methoxy-5-(2-ethylhexyloxy)-1,4-bis(1-cyanovinylenephenylene)]-alt-co-[2, 5-bis(N,N'-diphenylamino)-1,4-phenylene]} (abbreviation: CN-PPV-DPD).

Further, when a plurality of light-emitting layers are provided and emission colors of the layers are made different, light emission of a desired color can be obtained from the light-emitting element as a whole. For example, the emission colors of first and second light-emitting layers are complementary in a light-emitting element having the two light-emitting layers, so that the light-emitting element can be made to emit white light as a whole. Note that the term "complementary" means color relationship in which an achromatic color is obtained when colors are mixed. That is, emission of white light can be obtained by mixture of light emitted from substances whose emission colors are complementary colors. Further, the same applies to a light-emitting element having three or more light-emitting layers.

The electron-transport layer 704 is a layer that includes a substance having a high electron-transport property. Examples of the substance for the electron-transport layer 704 include metal complexes such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, and bis[2-(2-hydroxyphenyl)benzothiazolato]zinc (abbreviation: Zn(BTZ)$_2$). A heteroaromatic compound can be used, such as 2-(4-biphenylyl)-5-(4-tertbutylphenyl)-1,3,4-oxadiazole (abbreviation: PBD), 1,3-bis [5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs). A high molecular compound can be used, such as poly(2,5-pyridinediyl) (abbreviation: PPy), poly[(9,9-dihexylfluorene-2,7-diye-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy). The substances described here are mainly substances having an electron mobility of $10^{-6}$ cm$^2$/Vs or more. Other than the above substances, a substance that has a property of transporting electrons holes than holes may be used.

Further, the electron-transport layer is not limited to a single layer, and may be a stack of two or more layers including any of the above substances.

The electron-injection layer 705 is a layer that includes a substance having a high electron-injection property. For the electron-injection layer 705, an alkali metal, an alkaline earth metal, and a compound thereof, such as lithium, cesium, calcium, lithium fluoride, cesium fluoride, calcium fluoride, or lithium oxide can be used. A rare earth metal compound such as erbium fluoride can be used. The above-mentioned substances for forming the electron-transport layer 704 can also be used.

Alternatively, the composite material in which an organic compound and an electron donor (donor) are mixed may be used for the electron-injection layer 705. Such a composite material is excellent in an electron-injection property and an electron-transport property because the electron donor causes electron generation in the organic compound. In this case, the organic compound is preferably a material excellent in transporting the generated electrons. Specifically, for example, the substances for forming the electron-transport layer 704 (e.g. a metal complex or a heteroaromatic compound), which are described above, can be used. The electron donor is preferably a substance showing an electron-donating property with respect to the organic compound. Specifically, an alkali metal, an alkaline earth metal, and a rare earth metal are preferable, and lithium, cesium, magnesium, calcium, erbium, ytterbium, and the like can be given. Alkali metal oxides or alkaline earth metal oxides are also preferable and examples are lithium oxide, calcium oxide, barium oxide, and the like. A Lewis base such as magnesium oxide can also be used. An organic compound such as tetrathiafulvalene (abbreviation: TTF) can also be used.

Note that the hole-injection layer 701, the hole-transport layer 702, the light-emitting layer 703, the electron-transport layer 704, and the electron-injection layer 705 which are described above can be formed by a method, such as an evaporation method (e.g. a vacuum evaporation method), an inkjet method, or a coating method.

Figure 1B:
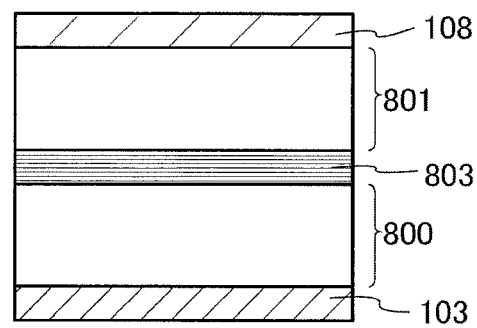

As illustrated in FIG. 1B, a plurality of EL layers may be stacked between the first electrode 103 and the second electrode 108. In this case, a charge generation layer 803 is preferably provided between a first EL layer 800 and a second EL layer 801 which are stacked. The charge generation layer 803 can be formed with either of the above-mentioned composite materials. Further, the charge generation layer 803 may have a stacked structure including a layer formed of the composite material and a layer formed of another material; in this case, as the layer formed of another material, a layer that includes a substance having an electron-donating property and a substance having a high electron-transport property, a layer formed of a transparent conductive film, or the like can be used. A light-emitting element having such a structure is less likely to have problems such as energy transfer and quenching, and gives an extensive choice of materials, and, accordingly, can easily be a light-emitting element having both high emission efficiency and a long lifetime. Further, a structure in which phosphorescence is obtained from one of the EL layers and fluorescence is obtained from the other is easily obtained. This structure can be combined with the above-mentioned structures of the EL layer.

Furthermore, when emission colors of EL layers are made different, light of a desired color can be obtained from the light-emitting element as a whole. For example, the emission colors of first and second EL layers are complementary in a light-emitting element having the two EL layers, so that the light-emitting element can be made to emit white light as a whole. Further, the same applies to a light-emitting element having three or more EL layers.

Figure 1C:
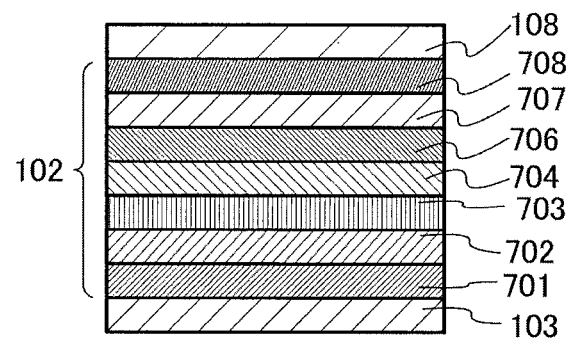

As illustrated in FIG. 1C, the EL layer 102 may include the hole-injection layer 701, the hole-transport layer 702, the light-emitting layer 703, the electron-transport layer 704, an electron-injection buffer layer 706, an electron-relay layer 707, and a composite material layer 708 which is in contact with the second electrode 108, between the first electrode 103 and the second electrode 108.

It is preferable to provide the composite material layer 708 which is in contact with the second electrode 108, because, in this case, damage to the EL layer 102 caused particularly when the second electrode 108 is formed by a sputtering method can be reduced. The composite material layer 708 can be formed using the above-described composite material in which a substance having an acceptor property is contained with an organic compound having a high hole-transport property.

Further, with the electron-injection buffer layer 706, an injection barrier between the composite material layer 708 and the electron-transport layer 704 can be reduced; thus, electrons generated in the composite material layer 708 can be easily injected into the electron-transport layer 704.

A substance having a high electron-injection property, such as an alkali metal, an alkaline earth metal, a rare earth metal, a compound of the above metal (e.g. an alkali metal compound (e.g. an oxide such as lithium oxide, a halide, or a carbonate such as lithium carbonate or cesium carbonate), an alkaline earth metal compound (e.g. an oxide, a halide, or a carbonate), or a rare earth metal compound (e.g. an oxide, a halide, or a carbonate), can be used for the electron-injection buffer layer 706.

Further, in the case where the electron-injection buffer layer 706 includes a substance having a high electron-transport property and a substance having a donor property, the substance having a donor property is preferably added so that the mass ratio thereof to the substance having a high electron-transport property is greater than or equal to 0.001 and less than or equal to 0.1. Note that as the substance having a donor property, an organic compound such as tetrathianaphthacene (abbreviation: TTN), nickelocene, or decamethylnickelocene can be used as well as an alkali metal, an alkaline earth metal, a rare earth metal, a compound of the above metal (e.g. an alkali metal compound (including an oxide of lithium oxide or the like, a halide, and a carbonate such as lithium carbonate or cesium carbonate), an alkaline earth metal compound (including an oxide, a halide, and a carbonate), and a rare earth metal compound (including an oxide, a halide, and a carbonate)). Note also that as the substance having a high electron-transport property, a material similar to the material for the electron-transport layer 704 described above can be used.

Furthermore, it is preferable that the electron-relay layer 707 be formed between the electron-injection buffer layer 706 and the composite material layer 708. The electron-relay layer 707 is not necessarily provided; however, with the electron-relay layer 707 having a high electron-transport property, electrons can be rapidly transported to the electron-injection buffer layer 706.

The structure in which the electron-relay layer 707 is interposed between the composite material layer 708 and the electron-injection buffer layer 706 is a structure in which the substance having an acceptor property included in the composite material layer 708 and the substance having a donor property included in the electron-injection buffer layer 706 are less likely to interact with each other, and thus their functions hardly interfere with each other. Accordingly, an increase in driving voltage can be suppressed.

The electron-relay layer 707 includes a substance having a high electron-transport property and is formed so that the LUMO level of the substance having a high electron-transport property is located between the LUMO level of the substance having an acceptor property included in the composite material layer 708 and the LUMO level of the substance having a high electron-transport property included in the electron-transport layer 704. In the case where the electron-relay layer 707 includes a donor substance, the donor level of the donor substance is controlled so as to be located between the LUMO level of the substance having an acceptor property included in the composite material layer 708 and the LUMO level of the substance having a high electron-transport property included in the electron-transport layer 704. As a specific value of the energy level, the LUMO level of the substance having a high electron-transport property included in the electron-relay layer 707 is preferably higher than or equal to −5.0 eV, more preferably higher than or equal to −5.0 eV and lower than or equal to −3.0 eV.

As the substance having a high electron-transport property included in the electron-relay layer 707, a phthalocyanine-based material or a metal complex having a metal-oxygen bond and an aromatic ligand is preferably used.

As the phthalocyanine-based material included in the electron-relay layer 707, any of the following is preferably used: CuPc, SnPc (phthalocyanine tin(II) complex), ZnPc (phthalocyanine zinc complex), CoPc (cobalt(II) phthalocyanine, β-form), FePc (phthalocyanine iron), and PhO-VOPc (vanadyl 2,9,16,23-tetraphenoxy-29H,31H-phthalocyanine).

A metal complex having a metal-oxygen double bond is preferably used as the metal complex having a metal-oxygen bond and an aromatic ligand, which is included in the electron-relay layer 707. The metal-oxygen double bond has an acceptor property (a property of easily accepting electrons); accordingly, electrons can be transferred (donated and accepted) more easily. Further, the metal complex having a metal-oxygen double bond is considered stable. Thus, the use of the metal complex having the metal-oxygen double bond enables the light-emitting element to be driven more stably at low voltage.

As the metal complex having a metal-oxygen bond and an aromatic ligand, a phthalocyanine-based material is preferable. Specifically, any of VOPc (vanadyl phthalocyanine), SnOPc (phthalocyanine tin(IV) oxide complex), and TiOPc (phthalocyanine titanium oxide complex) is preferable because a metal-oxygen double bond is likely to act on another molecule in terms of a molecular structure and an acceptor property is high.

Note that as the phthalocyanine-based materials described above, a phthalocyanine-based material having a phenoxy group is preferable. Specifically, a phthalocyanine derivative having a phenoxy group, such as PhO-VOPc, is preferable. The phthalocyanine derivative having a phenoxy group is soluble in a solvent and therefore has the advantage of being easy to handle during formation of a light-emitting element and the advantage of facilitating maintenance of an apparatus used for film formation.

The electron-relay layer 707 may further include a substance having a donor property. As the substance having a donor property, an organic compound such as tetrathianaphthacene (abbreviation: TTN), nickelocene, or decamethylnickelocene can be used as well as an alkali metal, an alkaline earth metal, a rare earth metal, and a compound of the above metal (e.g. an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate)). When such a substance having a donor property is included in the electron-relay layer 707, electrons can be transferred easily and the light-emitting element can be driven at lower voltage.

In the case where the substance having a donor property is included in the electron-relay layer 707, other than the materials described above as the substance having a high electron-transport property, a substance having a LUMO level higher than the acceptor level of the substance having an acceptor property included in the composite material layer 708 can be used. Specifically, it is preferable to use a substance having a LUMO level higher than or equal to −5.0 eV, preferably higher than or equal to −5.0 eV and lower than or equal to −3.0 eV. Examples of sixth a substance are perylene derivatives, nitrogen-containing condensed aromatic compounds, and the like. Note that a nitrogen-containing condensed aromatic compound is preferably used for a material used for formation of the electron-relay layer 707 because of its stability.

Specific examples of the perylene derivative are 3,4,9,10-perylenetetracarboxylic dianhydride (abbreviation: PTCDA), 3,4,9,10-perylenetetracarboxylic-bis-benzimidazole (abbreviation: PTCBI), N,N'-dioctyl-3,4,9,10-perylenetetracarboxylic diimide (abbreviation: PTCDI-C8H), N,N'-dihexyl-3,4,9,10-perylenetetracarboxylic diimide (abbreviation: Hex PTC), and the like.

Specific examples of the nitrogen-containing condensed aromatic compound are pirazino[2,3-f][1,10]phenanthroline-2,3-dicarbonitrile (abbreviation: PPDN), 2,3,6,7,10,11-hexacyano-1,4,5,8,9,12-hexaazatriphenylene (abbreviation: HAT(CN)$_6$), 2,3-diphenylpyrido[2,3-b]pyrazine (abbreviation: 2PYPR), 2,3-bis(4-fluorophenyl)pyrido[2,3-b]pyrazine (abbreviation: F2PYPR), and the like.

Besides, 7,7,8,8-tetracyanoquinodimethane (abbreviation: TCNQ), 1,4,5,8-naphthalenetetracarboxylic dianhydride (abbreviation: NTCDA), perfluoropentacene, copper hexadecafluorophthalocyanine (abbreviation: F$_{16}$CuPc), N,N'-bis(2,2,3,3,4,4,5,5,6,6,7,7,8,8-pentadecafluorooctyl)-1,4,5,8-naphthalenetetracarboxylic diimide (abbreviation: NTCDI-C8F), 3',4'-dibutyl-5,5"-bis(dicyanomethylene)-5,5"-dihydro-2,2':5',2"-terthiophene (abbreviation: DCMT), a methanofullerene (e.g. [6,6]-phenyl C$_{61}$ butyric acid methyl ester), or the like can be used.

Note that in the case where the substance having a donor property is included in the electron-relay layer 707, the electron-relay layer 707 can be formed by a method such as co-evaporation of the substance having a high electron-transport property and the substance having a donor property.

The hole-injection layer 701, the hole-transport layer 702, the light-emitting layer 703, and the electron-transport layer 704 can be formed using any of the above-described materials.

As described above, the EL layer 102 of this embodiment can be fabricated.

In the above-described light-emitting element, a current flows due to a potential difference generated between the first electrode 103 and the second electrode 108, and holes and electrons recombine in the EL layer 102, which leads to light emission. Then, this light emission is extracted out through one or both of the first electrode 103 and the second electrode 108. One or both of the first electrode 103 and the second electrode 108 thus have a property of transmitting visible light.

Further, the structure of the layers provided between the first electrode 103 and the second electrode 108 is not limited to the above-described structure. A structure other than the above may be employed as long as a light-emitting region in which holes and electrons recombine is provided in a portion away from the first electrode 103 and the second electrode 108 so as to prevent quenching due to proximity of the light-emitting region to metal.

In other words, there is no particular limitation on a stacked structure of the layers. A layer that includes a substance having a high electron-transport property, a substance having a high hole-transport property, a substance having a high electron-injection property, a substance having a high hole-injection property, a bipolar substance (a substance having a high electron-transport property and a high hole-transport property), a hole-blocking material, or the like can be freely combined with a light-emitting layer including any of the heterocyclic compounds according to one embodiment of the present invention as a host material.

Since the heterocyclic compounds according to one embodiment of the present invention are substances having a high electron-transport property, any of the heterocyclic compounds according to one embodiment of the present invention can also be used for the electron-transport layer.

Furthermore, when any of the heterocyclic compounds according to one embodiment of the present invention is applied to both for a host material in the light-emitting layer and for the electron-transport layer, extremely low-voltage driving can be realized.

With the use of a light-emitting element described in this embodiment, a passive matrix light-emitting device or an active matrix light-emitting device in which driving of the light-emitting element is controlled by a transistor can be manufactured.

In fabrication of an active matrix light-emitting device, there is no particular limitation on the structure of the transistor; for example, a staggered transistor or an inverted staggered transistor can be used as appropriate. In addition, a driver circuit formed over a substrate may be formed with an n-type transistor and a p-type transistor, or with either an n-type transistor or a p-type transistor. Further, there is no particular limitation on the crystallinity of a semiconductor film used for the transistor; for example, an amorphous semiconductor film or a crystalline semiconductor film can be used. As a material of the semiconductor film, a compound semiconductor such as GaAs, InP, SiC, ZnSe, GaN, or SiGe can be used in addition to an elemental substance such as silicon or germanium. An oxide semiconductor such as zinc oxide, tin oxide, magnesium zinc oxide, gallium oxide, or indium oxide, an oxide semiconductor including two or more of the above oxide semiconductors, or the like can be used.

Thus, a light-emitting element can be fabricated using any of the heterocyclic compounds according to one embodiment of the present invention. By use of any of the heterocyclic compounds according to one embodiment of the present invention for a light-emitting element, it is possible to obtain a light-emitting element having low driving voltage, a light-emitting element having high current efficiency, or a light-emitting element having a long lifetime.

Furthermore, a light-emitting device (such as an image display device) using a light-emitting element according to one embodiment of the present invention which is obtained as above can have low power consumption.

Embodiment 3

In this embodiment, a light-emitting device to which one embodiment of the present invention is applied is described with reference to FIGS. 2A and 2B. Note that FIG. 2A is a top view illustrating the light-emitting device, and FIG. 2B is a cross-sectional view taken along lines A-B and C-D of FIG. 2A.

The light-emitting device of this embodiment includes a source side driver circuit 401 and a gate side driver circuit 403 which are driver circuit portions, a pixel portion 402, a sealing substrate 404, a sealing material 405, a flexible printed circuit (FPC) 409, and an element substrate 410. A portion enclosed by the sealing material 405 is a space.

A lead wiring 408 is a wiring for transmitting signals that are to be input to the source side driver circuit 401 and the gate side driver circuit 403, and receives a video signal, a clock signal, a start signal, a reset signal, and the like from the FPC 409 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

Figure 2A:
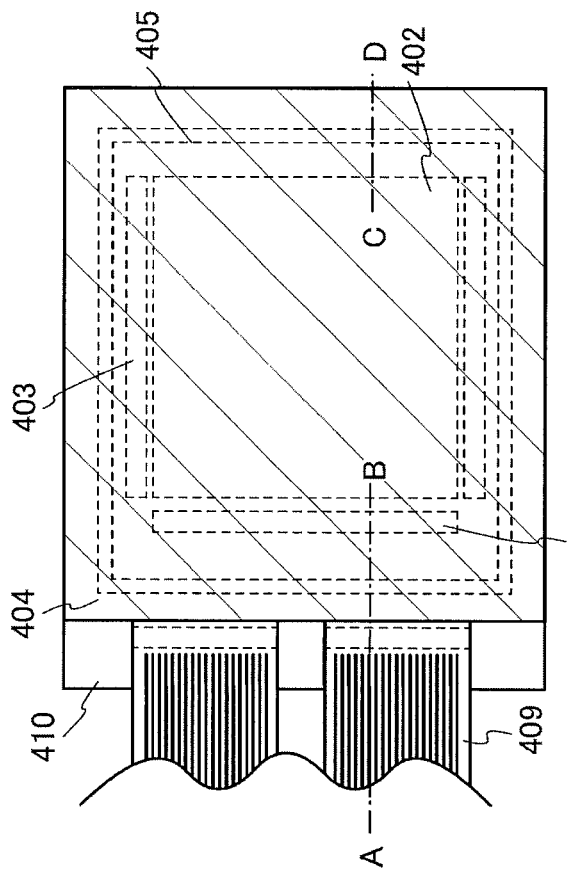
FIGS. 2A and 2B illustrate a light-emitting device according to one embodiment of the present invention.
Figure 2B:
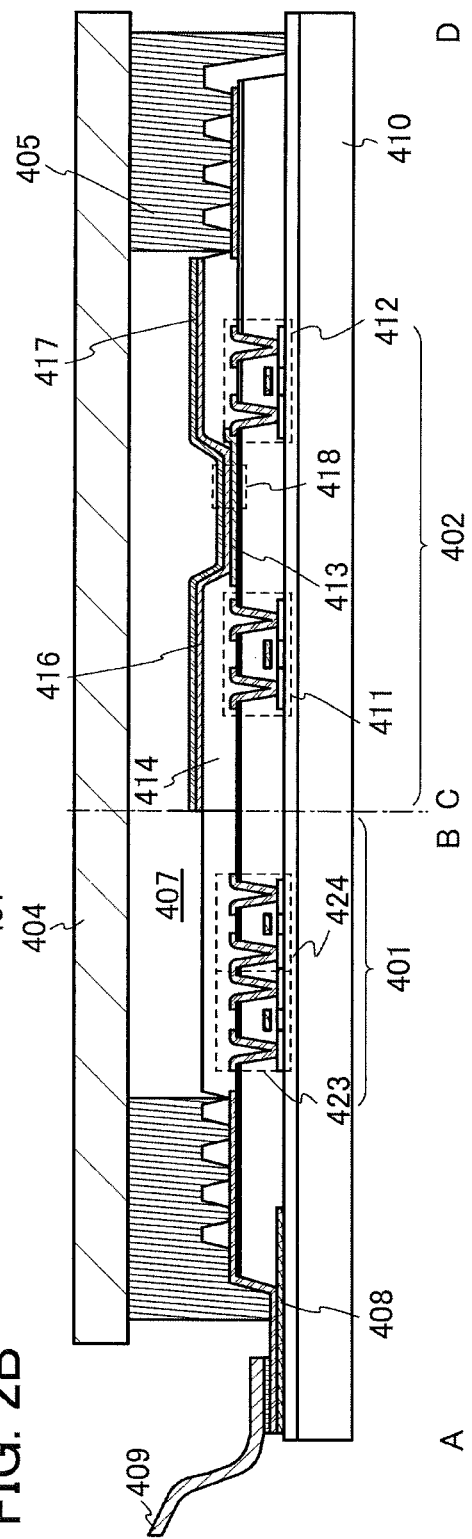

The driver circuit portion and the pixel portion are formed over an element substrate 410 illustrated in FIG. 2A. In FIG. 2B, the source side driver circuit 401 which is the driver circuit portion and one pixel in the pixel portion 402 are illustrated.

Note that as the source side driver circuit 401, a CMOS circuit in which an n-channel TFT 423 and a p-channel TFT 424 are combined is formed. The driver circuit may be any of a variety of circuits formed with TFTs, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 402 includes a plurality of pixels having a switching TFT 411, a current control TFT 412, and a first electrode 413 electrically connected to a drain of the current control TFT 412. Note that an insulator 414 is formed to cover an end portion of the first electrode 413. Here, the insulator 414 is formed by use of a positive type photosensitive acrylic resin film.

In order to improve coverage, the insulator 414 is provided such that either an upper end portion or a lower end portion of the insulator 414 has a curved surface with a curvature. For example, when positive photosensitive acrylic is used as a material for the insulator 414, it is preferable that only an upper end portion of the insulator 414 have a curved surface with a radius of curvature (0.2 μm to 3 μm). For the insulator 414, it is also possible to use either a negative type photosensitive material that becomes insoluble in an etchant by light irradiation or a positive type one that becomes soluble in an etchant by light irradiation.

An EL layer 416 and a second electrode 417 are formed over the first electrode 413. The first electrode, the EL layer, and the second electrode can be formed with materials given in Embodiment 2. In addition, the EL layer 416 includes any of the heterocyclic compounds according to one embodiment of the present invention.

Further, the sealing substrate 404 is attached to the element substrate 410 with the sealing material 405, so that a light-emitting element 418 is provided in a space 407 enclosed by the element substrate 410, the sealing substrate 404, and the sealing material 405. The space 407 is filled with a filler, and may be filled with an inert gas (such as nitrogen or argon) or the sealing material.

Note that an epoxy-based resin is preferably used as the sealing material 405. Such a material preferably allows as little moisture and oxygen as possible to penetrate. As a material used for the sealing substrate 404, a plastic substrate formed of fiberglass-reinforced plastics (FRP), polyvinyl fluoride (PVF), polyester, acrylic, or the like can be used other than a glass substrate or a quartz substrate.

As described above, the active matrix light-emitting device including the light-emitting element according to one embodiment of the present invention can be obtained.

Figure 3A:
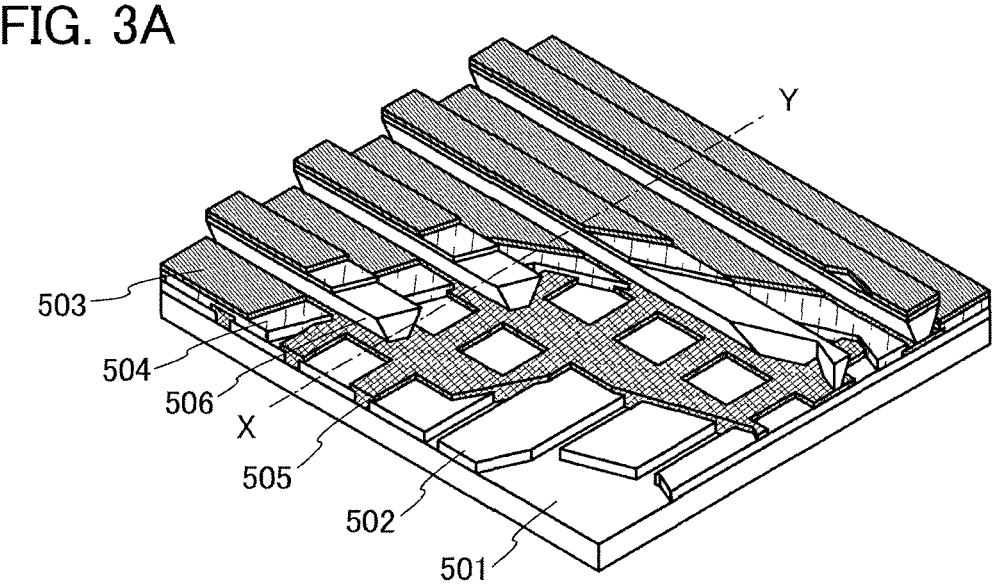
FIGS. 3A and 3B illustrate a light-emitting device according to one embodiment of the present invention.
Figure 3B:
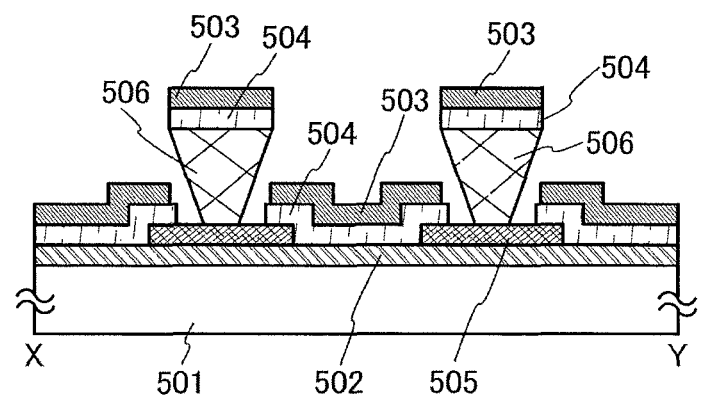

Further, a light-emitting element according to one embodiment of the present invention can be used for a passive matrix light-emitting device as well as the above active matrix light-emitting device. FIGS. 3A and 3B illustrate a perspective view and a cross-sectional view of a passive matrix light-emitting device including a light-emitting element according to one embodiment of the present invention. Note that FIG. 3A is a perspective view of the light-emitting device, and FIG. 3B is a cross-sectional view taken along line X-Y of FIG. 3A.

In FIGS. 3A and 3B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that a distance between both the sidewalls is gradually narrowed toward the surface of the substrate. In other words, a cross section taken along the direction of the short side of the partition layer 506 is trapezoidal, and the base (side in contact with the insulating layer 505) is shorter than the upper side (side not in contact with the insulating layer 505). With the partition layer 506 provided in such a way, a defect of a light-emitting element due to crosstalk or the like can be prevented.

Figure 14A:
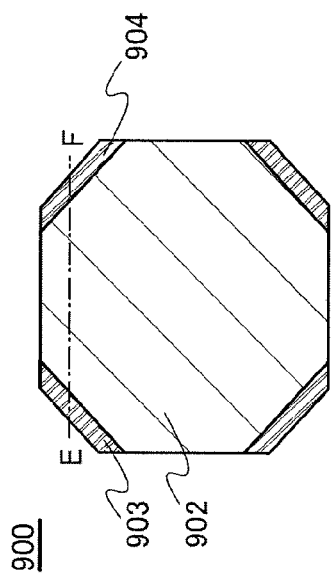
FIGS. 14A to 14C illustrate light-emitting devices according to one embodiment of the present invention.
Figure 14B:
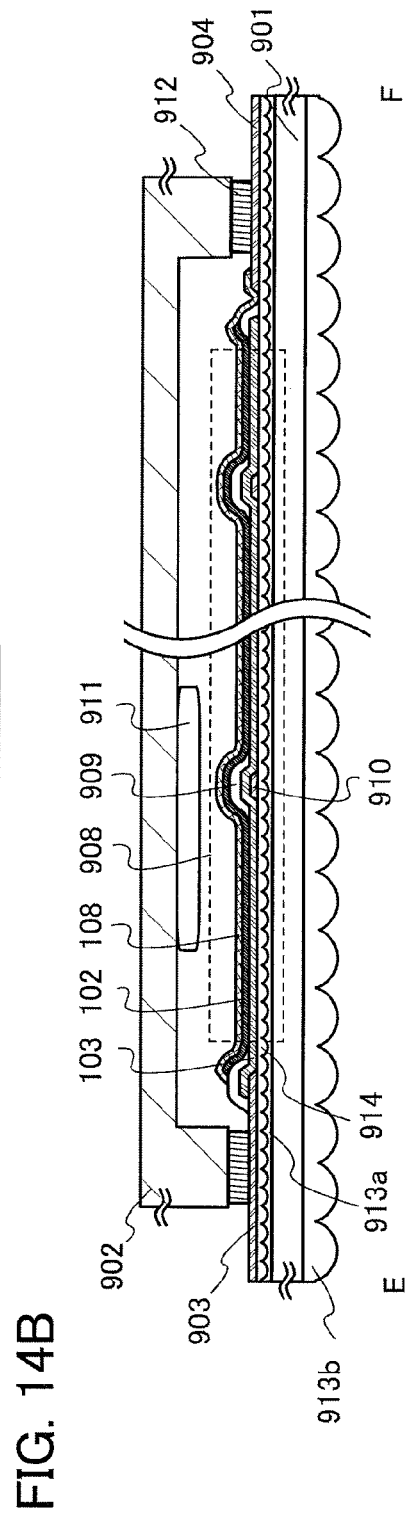
Figure 14C:
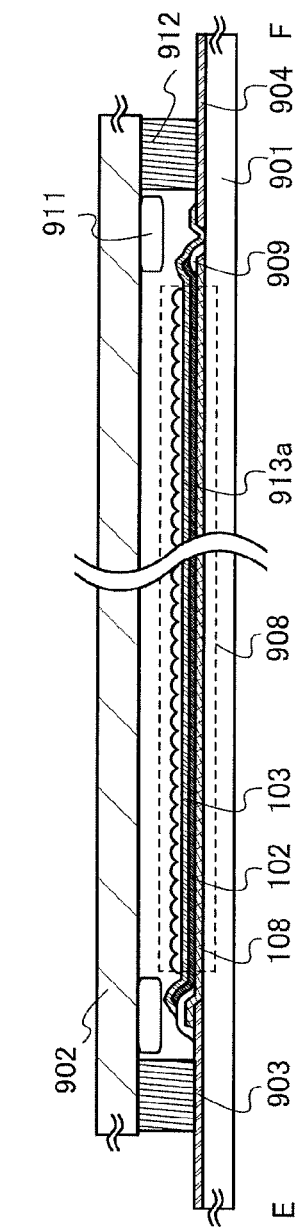

Examples of light-emitting devices to which one embodiment of the present invention is applied are illustrated in FIGS. 14A to 14C. FIG. 14A is a top view illustrating the light-emitting devices, and FIGS. 14B and 14C are cross-sectional views taken along line E-F in FIG. 14A.

Light-emitting devices 900 illustrated in FIGS. 14A to 14C include a light-emitting element 908 (a first electrode 103, an EL layer 102, and a second electrode 108) over a first substrate 901. The light-emitting element 908 can be formed using any of the materials described in Embodiment 2. The EL layer 102 includes any of the heterocyclic compounds according to one embodiment of the present invention.

To the light-emitting devices of this embodiment, any of the following structures can be applied: a structure in which a light-emitting element emits light upward (such a structure is also referred to as a top emission structure); a structure in which a light-emitting element emits light upward and downward (such a structure is also referred to as a dual emission structure); and a structure in which a light-emitting element emits light downward (such a structure is also referred to as a bottom emission structure).

A light-emitting device having a bottom emission structure is illustrated in FIG. 14B.

The light-emitting device illustrated in FIG. 14B has the first electrode 103 over the first substrate 901, the EL layer 102 over the first electrode 103, and the second electrode 108 over the EL layer 102.

A first terminal 903 is electrically connected to an auxiliary wiring 910 and the first electrode 103, and a second terminal 904 is electrically connected to the second electrode 108. Further, an insulating layer 909 is formed between end portions of the first electrode 103 and the second electrode 108 and between the auxiliary wiring 910 and the EL layer 102. Note that although a structure in which the first electrode 103 is formed over the auxiliary wiring 910 is illustrated in FIG. 14B, a structure in which the auxiliary wiring 910 is formed over the first electrode 103 may be possible.

In addition, the first substrate 901 and the second substrate 902 are bonded together by a sealing material 912. Further, a desiccant 911 may be included between the first substrate 901 and the second substrate 902.

Further, the upper and/or lower portions of the first substrate 901 may be provided with a light extraction structure. As the light extraction structure, an uneven structure can be provided at an interface through which light is transmitted from the side having a high refractive index to the side having a low refractive index. A specific example is as follows: as illustrated in FIG. 14B, a light extraction structure 913a with minute unevenness is provided between the light-emitting element 908 having a high refractive index and the first substrate 901 having a lower refractive index, and a light extraction structure 913b with unevenness is provided between the first substrate 901 and the air.

However, in the light-emitting element, unevenness of the first electrode 103 might cause leakage current generation in the EL layer 102 formed over the first electrode 103. Therefore, in this embodiment, a planarization layer 914 having a refractive index higher than or equal to that of the EL layer 102 is provided in contact with the light extraction structure 913a. Accordingly, the first electrode 103 can be a flat film, and the leakage current generation in the EL layer due to the unevenness of the first electrode 103 can be suppressed. Further, because of the light extraction structure 913a at an interface between the planarization layer 914 and the first substrate 901, light which cannot be extracted to the air due to total reflection can be reduced, so that the light extraction efficiency of the light-emitting device can be increased.

The present invention is not limited to the structure in which the first substrate 901, the light extraction structure 913a, and the light extraction structure 913b are different components as in FIG. 14B. Two or all of these may be formed as one component. The light extraction structure 913a may be all formed inside a sealing region.

A light-emitting device having a top emission structure is illustrated in FIG. 14C.

The light-emitting device illustrated in FIG. 14C has the second electrode 108 over the first substrate 901, the EL layer 102 over the second electrode 108, and the first electrode 103 over the EL layer 102.

The first terminal 903 is electrically connected to the second electrode 108, and the second terminal 904 is electrically connected to the first electrode 103. Further, the insulating layer 909 is formed between end portions of the first electrode 103 and the second electrode 108.

In addition, the first substrate 901 and the second substrate 902 are bonded together by the sealing material 912. Further, an auxiliary wiring may be formed over the first electrode 103. Furthermore, the desiccant 911 may be included between the first substrate 901 and the second substrate 902. The desiccant 911 is preferably provided at a position that does not overlap a light-emitting region of a light-emitting element. Alternatively, a desiccant that transmits light from the light-emitting element is preferably used.

Although the light-emitting device 900 illustrated in FIG. 14A is octagonal, the present invention is not limited to this shape. The light-emitting device 900 and the light-emitting element 908 may have other polygonal shapes or a shape having a curve. As the shape of the light-emitting device 900, a triangle, a quadrangle, a hexagon, or the like is particularly preferred. This is because such a shape allows a plurality of light-emitting devices 900 to be provided in a limited area without a space therebetween, and also because such a shape enables effective use of the limited substrate area for formation of the light-emitting device 900. Further, the number of elements formed over the substrate is not limited to one and a plurality of elements may be provided.

As materials of the first substrate 901 and the second substrate 902, a material having a light-transmitting property, such as glass, quartz, or an organic resin can be used. At least one of the first substrate 901 and the second substrate 902 transmits light emitted from the light-emitting element.

In the case where an organic resin is used for the substrates, for example, any of the following can be used as the organic resin: polyester resins such as polyethylene terephthalate (PET) and polyethylene naphthalate (PEN), a polyacrylonitrile resin, a polyimide resin, a polymethylmethacrylate resin, a polycarbonate (PC) resin, a polyethersulfone (PES) resin, a polyamide resin, a cycloolefin resin, a polystyrene resin, a polyamide imide resin, a polyvinylchloride resin, and the like. A substrate in which a glass fiber is impregnated with an organic resin or a substrate in which an inorganic filler is mixed with an organic resin can also be used.

Thus, the light-emitting device to which one embodiment of the present invention is applied can be obtained.

The light-emitting devices described in this embodiment are formed using a light-emitting element according to one embodiment of the present invention, and accordingly, the light-emitting devices have low power consumption.

Note that this embodiment can be implemented in appropriate combination with any of the other embodiments.

Embodiment 4

In this embodiment, with reference to FIGS. 4A to 4E and FIGS. 5A and 5B, description is given of examples of a variety of electronic devices and lighting devices that are each completed by use of a light-emitting device according to one embodiment of the present invention.

Examples of the electronic devices are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pachinko machines, and the like.

An electronic device or a lighting device that has a light-emitting portion with a curved surface can be realized with a light-emitting element including any of the heterocyclic compounds according to one embodiment of the present invention, which is fabricated over a substrate having flexibility.

In addition, an electronic device or a lighting device that has a see-through light-emitting portion can be realized with a light-emitting element including any of the heterocyclic compounds according to one embodiment of the present invention, in which a pair of electrodes is formed using a material having a property of transmitting visible light.

Further, a light-emitting device to which one embodiment of the present invention is applied can also be applied to a lighting device for motor vehicles, examples of which are lighting devices for a dashboard, a windshield, a ceiling, and the like.

Figure 4A:
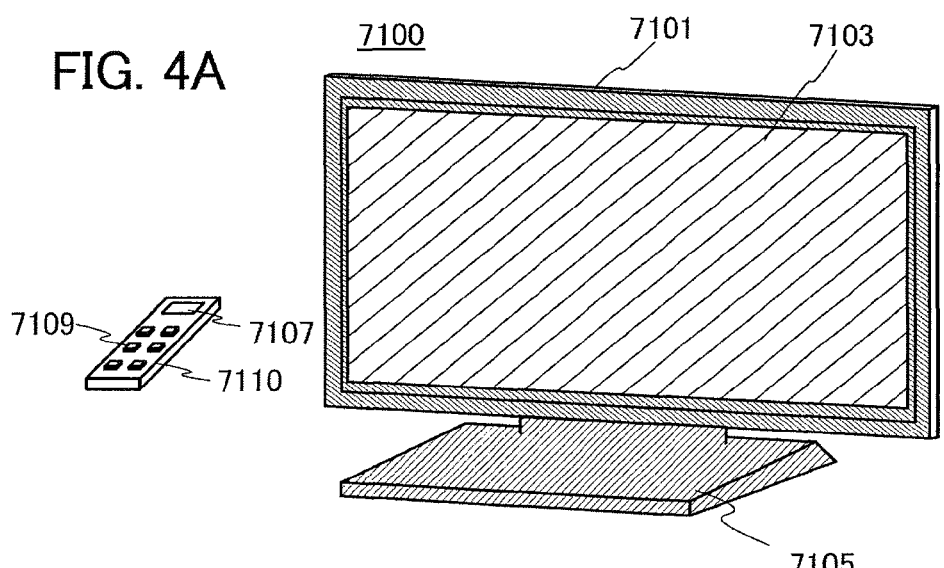
FIGS. 4A to 4E each illustrate an electronic device according to one embodiment of the present invention.

In FIG. 4A, an example of a television device is illustrated. In a television device 7100, a display portion 7103 is incorporated in a housing 7101. The display portion 7103 is capable of displaying images, and the light-emitting device can be used for the display portion 7103. In addition, here, the housing 7101 is supported by a stand 7105.

The television device 7100 can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 4B:
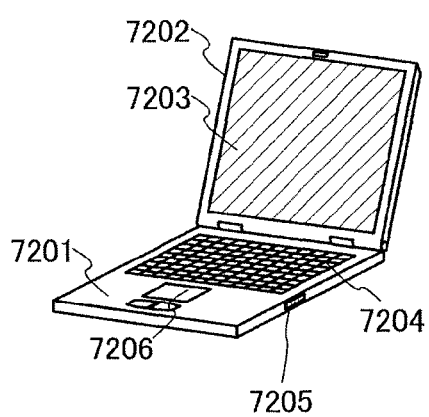

In FIG. 4B, a computer is illustrated, which includes a main body 7201, a housing 7202, a display portion 7203, a keyboard 7204, an external connection port 7205, a pointing device 7206, and the like. This computer is manufactured with the use of the light-emitting device for the display portion 7203.

Figure 4C:
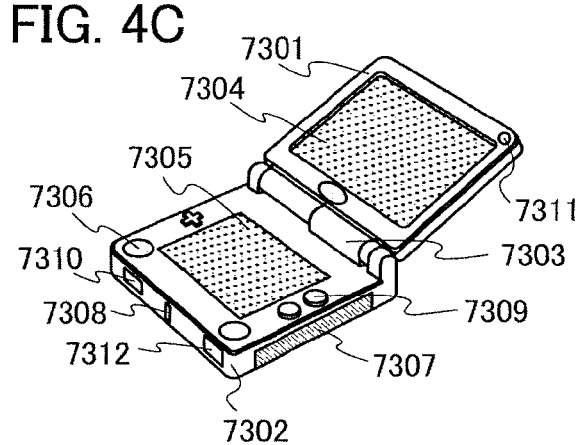

In FIG. 4C, a portable amusement machine is illustrated, which includes two housings, a housing 7301 and a housing 7302, connected with a joint portion 7303 so that the portable amusement machine can be opened or closed. A display portion 7304 is incorporated in the housing 7301 and a display portion 7305 is incorporated in the housing 7302. In addition, the portable amusement machine illustrated in FIG. 4C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substances, sound, time, hardness, electric field, current, voltage, electric power, radiation, flow rate, humidity, gradient, oscillation, odor, or infrared rays), and a microphone 7312), and the like. It is needless to say that the structure of the portable amusement machine is not limited to the above as long as the light-emitting device is used for at least either the display portion 7304 or the display portion 7305, or both, and may include other accessories as appropriate. The portable amusement machine illustrated in FIG. 4C has a function of reading out a program or data stored in a storage medium to display it on the display portion, and a function of sharing information with another portable amusement machine by wireless communication. The portable amusement machine illustrated in FIG. 4C can have a variety of functions without limitation to the above.

Figure 4D:
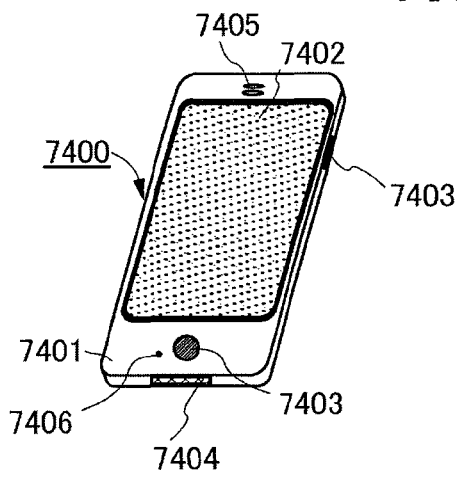

In FIG. 4D, an example of a cellular phone is illustrated. A cellular phone 7400 is provided with a display portion 7402 incorporated in a housing 7401, operation buttons 7403, an external connection port 7404, a speaker 7405, a microphone 7406, and the like. Note that the cellular phone 7400 is manufactured with the use of the light-emitting device for the display portion 7402.

When the display portion 7402 of the cellular phone 7400 illustrated in FIG. 4D is touched with a finger or the like, data can be input to the cellular phone 7400. Further, operations such as making a phone call and writing e-mail can be performed by touch on the display portion 7402 with a finger or the like.

There are mainly three screen modes of the display portion 7402. The first mode is a display mode mainly for displaying an image. The second mode is an input mode mainly for inputting information such as a character. The third mode is a display-and-input mode in which two modes of the display mode and the input mode are mixed.

For example, in the case where a phone call is made or e-mail is written, the character input mode for mainly for inputting a character is selected for the display portion 7402 so that a character displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touch on the display portion 7402 or operation with the operation buttons 7403 of the housing 7401. The screen modes can also be switched depending on kinds of images displayed on the display portion 7402. For example, when a signal for an image to be displayed on the display portion is for moving images, the screen mode is switched to the display mode; when the signal is for text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, so that personal identification can be performed. Furthermore, by provision of a backlight or a sensing light source emitting near-infrared light for the display portion, an image of a finger vein, a palm vein, or the like can also be taken.

Figure 4E:
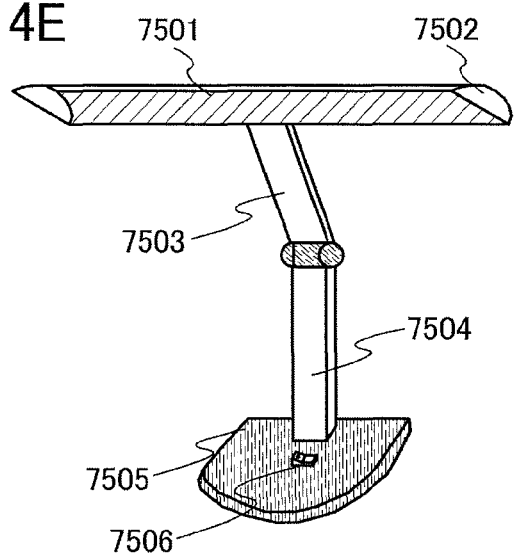

In FIG. 4E, a desk lamp is illustrated, which includes a lighting portion 7501, a shade 7502, an adjustable arm 7503, a support 7504, a base 7505, and a power switch 7506. The desk lamp is manufactured with the use of the light-emitting device for the lighting portion 7501. Note that the "lighting device" also includes ceiling lights, wall lights, and the like.

Figure 5A:
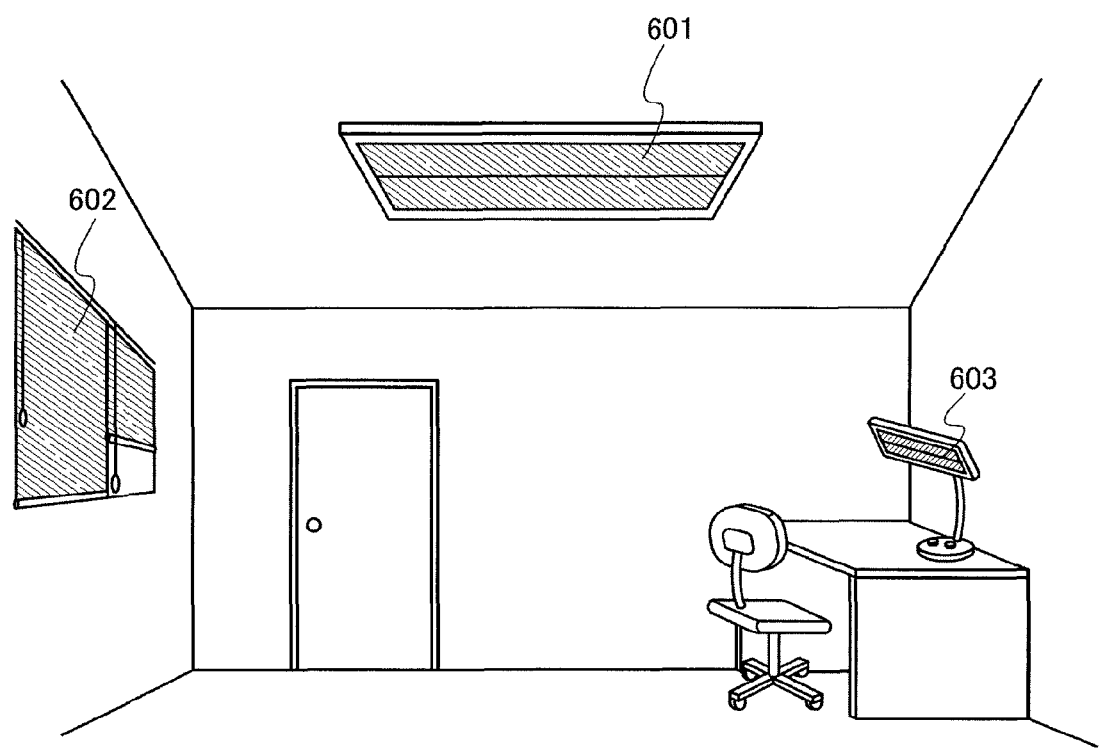
FIGS. 5A and 5B illustrate lighting devices according to one embodiment of the present invention.

In FIG. 5A, an example in which the light-emitting device is used for an interior lighting device 601 is illustrated. Since the light-emitting device can have a larger area, it can be used as a lighting device having a large area. Furthermore, the light-emitting device can be used as a roll-type lighting device 602. As illustrated in FIG. 5A, a desk lamp 603 described with reference to FIG. 4E may also be used in a room provided with the interior lighting device 601.

Figure 5B:
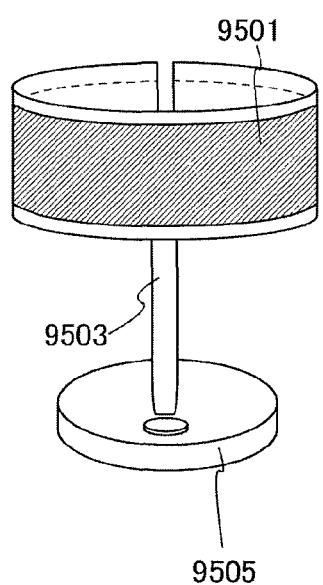

In FIG. 5B, an example of another lighting device is illustrated. A table lamp illustrated in FIG. 5B includes a lighting portion 9501, a support 9503, a support base 9505, and the like. The lighting portion 9501 includes any of the heterocyclic compounds according to one embodiment of the present invention. Thus, a lighting device that has a curved surface or a lighting portion that can be flexibly bent can be provided by fabrication of a light-emitting element over a substrate having flexibility. Such use of a flexible light-emitting device for a lighting device enables a place having a curved surface, such as the ceiling or dashboard of a motor vehicle, to be provided with the lighting device, as well as increases the degree of freedom in design of the lighting device.

In the above-described manner, electronic devices or lighting devices can be obtained by application of the light-emitting device. Application range of the light-emitting device is so wide that the light-emitting device can be applied to electronic devices in a variety of fields.

Note that the structure described in this embodiment can be combined with any of the structures described in the other embodiments as appropriate.

Example 1

Synthesis Example 1

This example specifically illustrates a method of synthesizing 7-[3-(dibenzothiophen-4-yl)phenyl]dibenzo[f,h]quinoxaline (abbreviation: 7mDBTPDBq-II) represented by the structural formula (101) in Embodiment 1. A structure of 7mDBTPDBq-II is illustrated below.

[Chemical Formula 59]

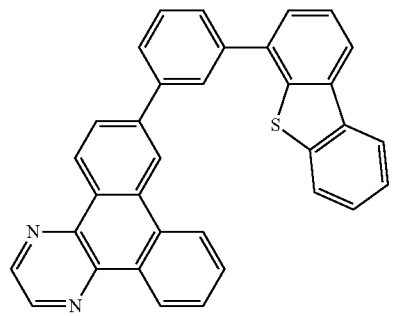

7mDBTPDBq-II

A scheme for the synthesis of 7mDBTPDBq-II is illustrated in (C-1).

[Chemical Formula 60]

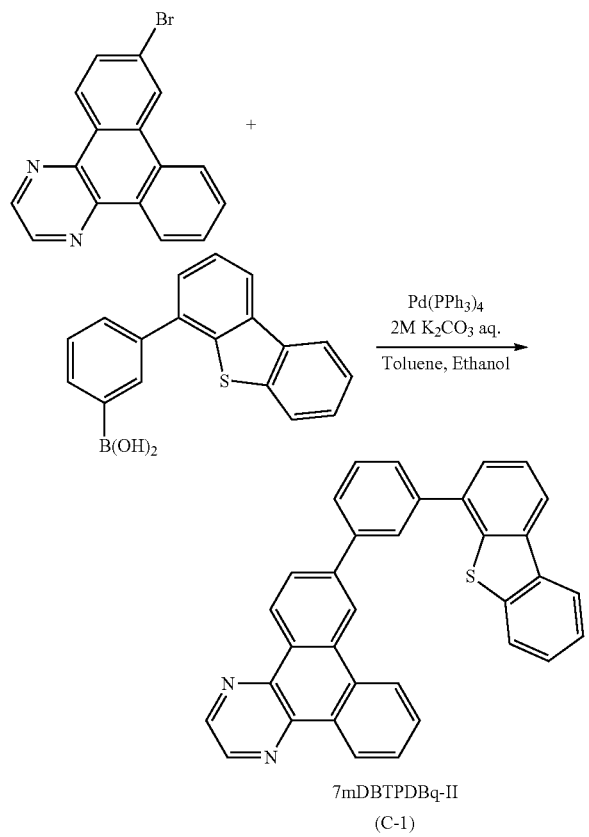

7mDBTPDBq-II
(C-1)

In a 50 mL three-neck flask were put 1.2 g (4.0 mmol) of 7-bromodibenzo[f,h]quinoxaline, 1.3 g (4.3 mmol) of 3-(dibenzothiophen-4-yl)phenylboronic acid, 20 mL of toluene, 4 mL of ethanol, and 4 mL of a 2M aqueous solution of potassium carbonate. This mixture was degassed by being stirred under reduced pressure, and the air in the flask was replaced with nitrogen. To this mixture was added 93 mg (81 μmol) of tetrakis(triphenylphosphine)palladium(0). This mixture was stirred at 80° C. for 7 hours under a nitrogen stream. After a predetermined time elapsed, water was added to the obtained mixture, and organic substances were extracted from the aqueous layer with toluene. The solution of the obtained extract was combined with the organic layer, the mixture was washed with water and saturated brine, and the organic layer was dried over magnesium sulfate. This mixture was gravity-filtered, and the filtrate was concentrated to give a solid. The obtained solid was purified by silica gel column chromatography (developing solvent: toluene), and further, recrystallization from toluene gave 1.4 g of a pale yellow powder in 61% yield, which was the object of the synthesis.

By a train sublimation method, 1.4 g of the obtained pale yellow powder which was the object of the synthesis was purified. In the sublimation purification, the object of the synthesis was heated at 255° C. under a pressure of 2.5 Pa with a flow rate of argon gas of 5 mL/min. After the sublimation purification, 0.60 g of a pale yellow powder which was the object of the synthesis was recovered in a yield of 42%.

Nuclear magnetic resonance (NMR) spectroscopy identified this compound as 7-[3-(dibenzothiophen-4-yl)phenyl] dibenzo[f,h]quinoxaline (abbreviation: 7mDBTPDBq-II), which was the object of the synthesis.

$^1$H NMR data of the obtained compound are as follows: $^1$H NMR (CDCl$_3$, 300 MHz): δ=7.47-7.51 (m, 2H), 7.62 (d, J=4.8 Hz, 2H), 7.68-7.92 (m, 6H), 8.08 (dd, J=8.4 Hz, 1.5 Hz, 1H), 8.19-8.24 (m, 3H), 8.74 (dd, J=7.8 Hz, 1.5 Hz, 1H), 8.91-8.93 (m, 3H), 9.24 (dd, J=7.2 Hz, 2.1 Hz, 1H), 9.31 (d, J=8.4 Hz, 1H).

Figure 7A:
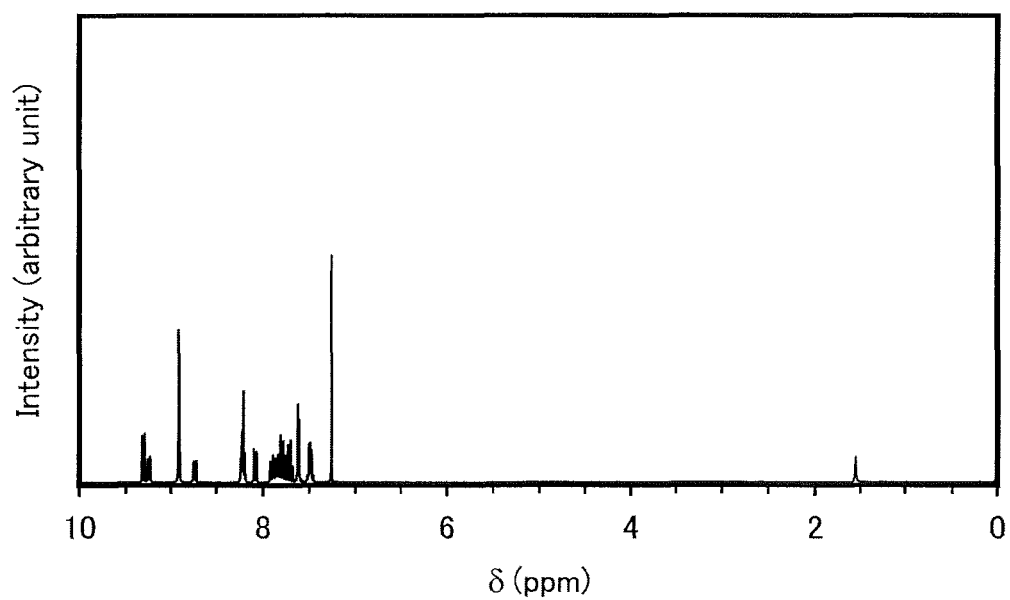
FIGS. 7A and 7B show $^1$H NMR charts of 7-[3-(dibenzothiophen-4-yl)phenyl]dibenzo[f,h]quinoxaline (abbreviation: 7mDBTPDBq-II)
Figure 7B:
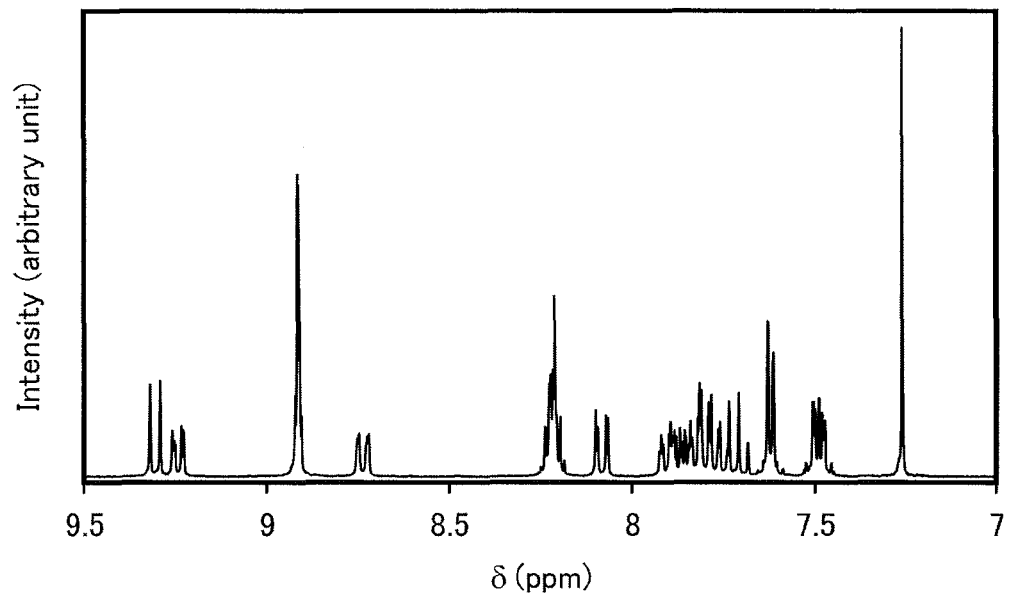

Further, $^1$H NMR charts are shown in FIGS. 7A and 7B. Note that FIG. 7B is a chart where the range of from 7.0 ppm to 9.5 ppm in FIG. 7A is enlarged.

Figure 8A:
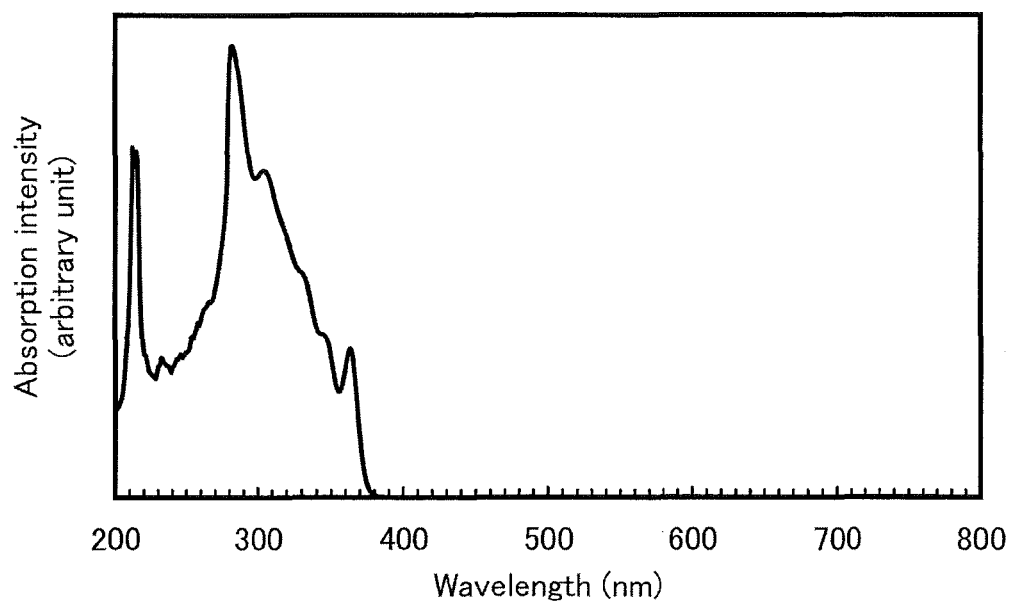
FIGS. 8A and 8B show an absorption and emission spectra of 7mDBTPDBq-II in a toluene solution of 7mDBTPDBq-II.
Figure 8B:
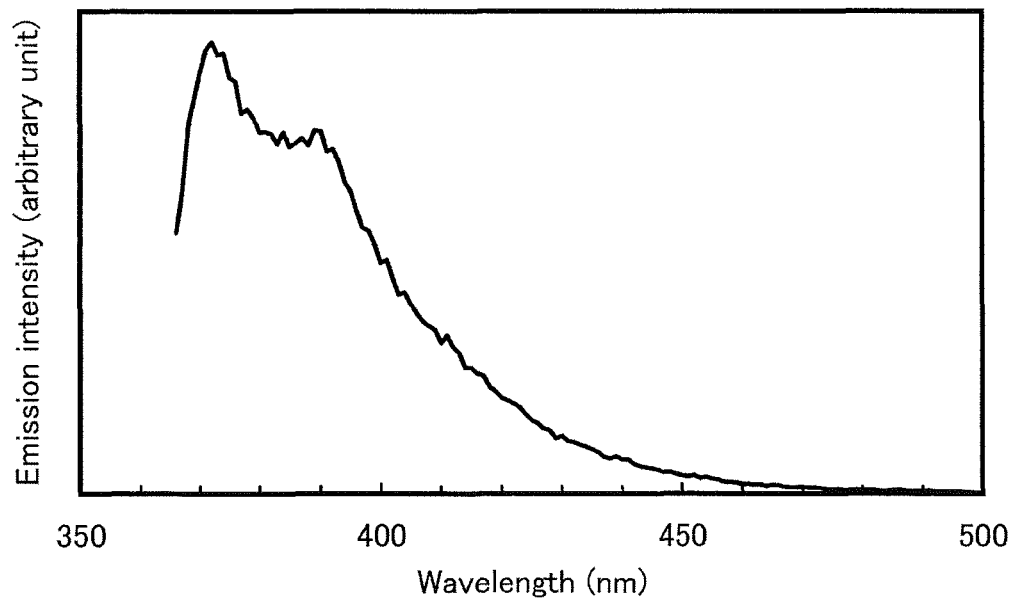
Figure 9A:
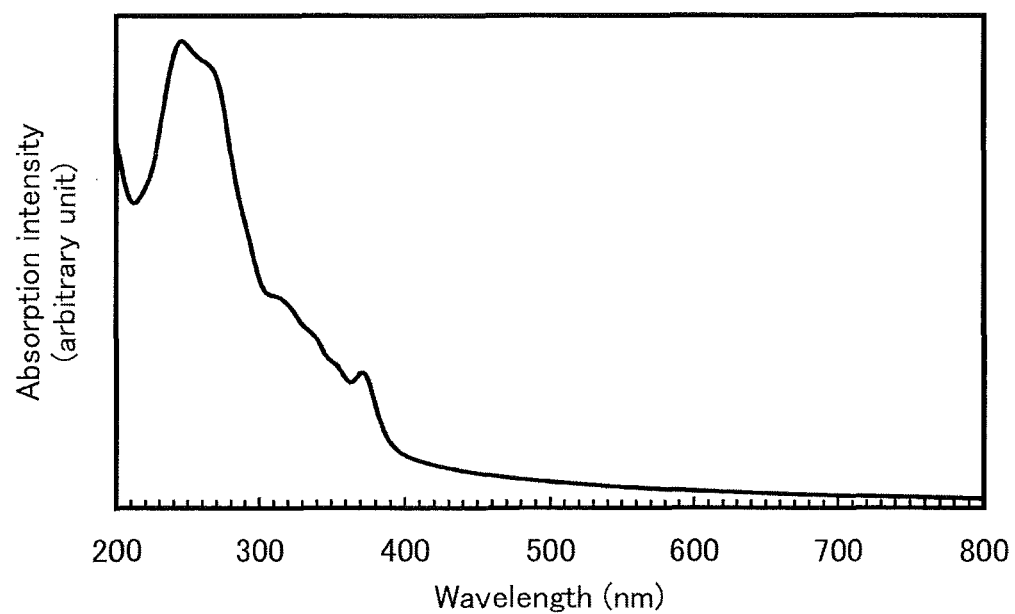
FIGS. 9A and 9B show an absorption and emission spectra of a thin film of 7mDBTPDBq-II.
Figure 9B:
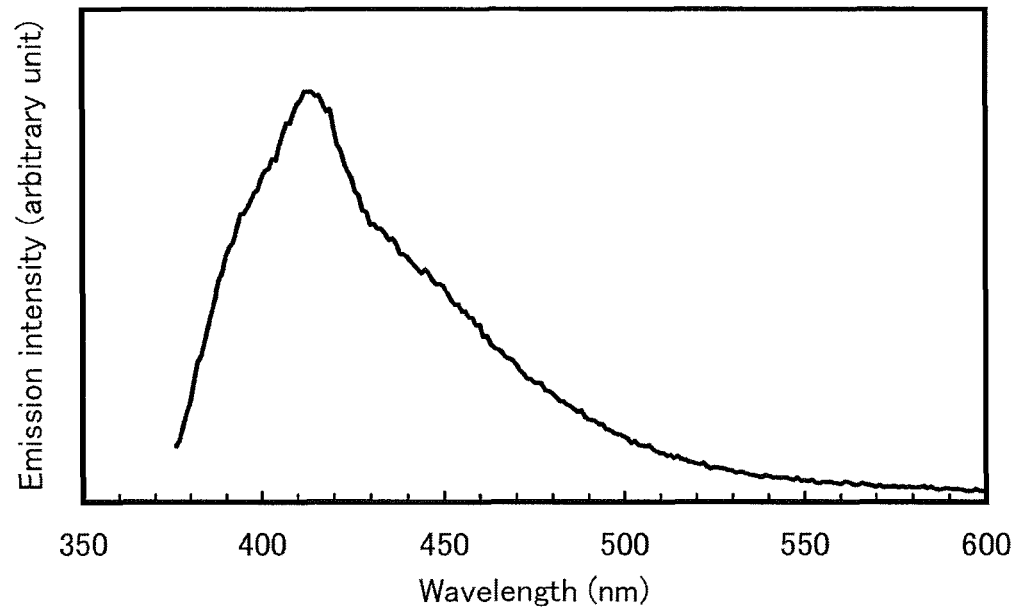

Further, FIG. 8A shows an absorption spectrum of 7mDBTPDBq-II in a toluene solution of 7mDBTPDBq-II, and FIG. 8B shows an emission spectrum thereof. Furthermore, FIG. 9A shows an absorption spectrum of a thin film of 7mDBTPDBq-II, and FIG. 9B shows an emission spectrum thereof. The absorption spectrum was measured using an ultraviolet-visible spectrophotometer (V-550, produced by JASCO Corporation). The measurements were performed with samples prepared in such a way that the solution was put in a quartz cell and the thin film was obtained by evaporation onto a quartz substrate. The figures show the absorption spectrum of the solution which was obtained by subtracting the absorption spectra of quartz and toluene from the absorption spectra of quartz and the solution, and the absorption spectrum of the thin film which was obtained by subtracting the absorption spectrum of a quartz substrate from the absorption spectra of the quartz substrate and the thin film. In FIG. 8A and FIG. 9A, the horizontal axis represents wavelength (nm) and the vertical axis represents absorption intensity (arbitrary unit). In FIG. 8B and FIG. 9B, the horizontal axis represents wavelength (nm) and the vertical axis represents emission intensity (arbitrary unit). In the case of the toluene solution, absorption peaks were observed at around 304 nm and 363 nm, and emission wavelength peaks were 372 nm and 389 nm (at an excitation wavelength of 360 nm). In the case of the thin film, absorption peaks were observed at around 246 nm, 263 nm, 312 nm, 335 nm, 350 nm and 371 nm, and an emission wavelength peak was 413 nm (at an excitation wavelength of 371 nm).

Example 2

Figure 6:
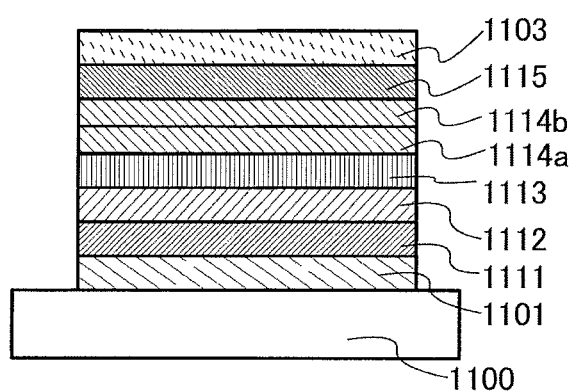
FIG. 6 illustrates a light-emitting element of Examples.

In this example, a light-emitting element according to one embodiment of the present invention is described referring to FIG. 6. Chemical formulae of materials used in this example are illustrated below.

[Chemical Formula 61]

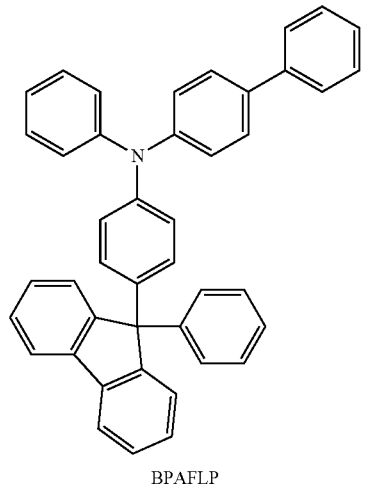

BPAFLP

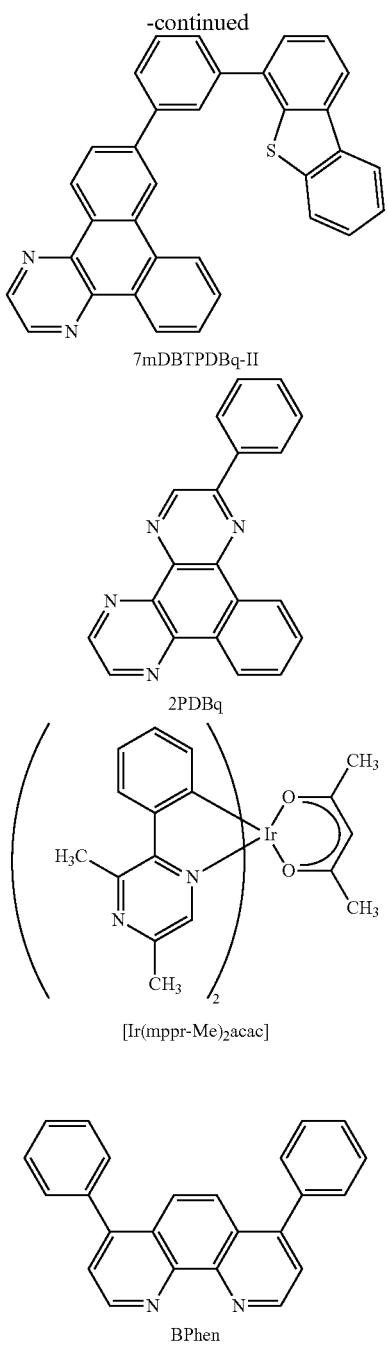

The ways how a light-emitting element 1 and a comparison light-emitting element 2 were fabricated are described hereinbelow.

(Light-Emitting Element 1)

First, a film of indium tin oxide containing silicon oxide (ITSO) was formed over a glass substrate 1100 by a sputtering method, so that a first electrode 1101 was formed. Note that its thickness was set to 110 nm and the electrode area was set to 2 mm×2 mm. Here, the first electrode 1101 is an electrode that functions as an anode of the light-emitting element.

In pretreatment for forming the light-emitting elements over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Then, the substrate 1100 over which the first electrode 1101 was formed was fixed to a substrate holder provided in a vacuum evaporation apparatus so that the surface on which the first electrode 1101 was formed faced downward. The pressure in the vacuum evaporation apparatus was reduced to about $10^{-4}$ Pa. After that, over the first electrode 1101, 4-phenyl-4'-(9-phenylfluoren-9-yl)triphenylamine (abbreviation: BPAFLP) and molybdenum(VI) oxide were co-evaporated by an evaporation method using resistance heating, so that a hole-injection layer 1111 was formed. The thickness of the hole-injection layer 1111 was set to 40 nm, and the weight ratio of BPAFLP to molybdenum oxide was adjusted to 4:2 (=BPAFLP:molybdenum oxide). Note that the co-evaporation method refers to an evaporation method in which evaporation is carried out from a plurality of evaporation sources at the same time in one treatment chamber.

Next, over the hole-injection layer 1111, a BPAFLP film was formed to a thickness of 20 nm, so that a hole-transport layer 1112 was formed.

Further, 7-[3-(dibenzothiophen-4-yl)phenyl]dibenzo[f,h]quinoxaline (abbreviation: 7mDBTPDBq-II) synthesized in Example 1 and (acetylacetonato)bis(3,5-dimethyl-2-phenylpyrazinato)iridium(III) (abbreviation: [Ir(mppr-Me)$_2$(acac)]) were co-evaporated to form a light-emitting layer 1113 over the hole-transport layer 1112. The weight ratio of 7mDBTPDBq-II to [Ir(mppr-Me)$_2$(acac)] was adjusted to 1:0.06 (=7mDBTPDBq-II:Ir(mppr-Me)$_2$(acac)]). The thickness of the light-emitting layer 1113 was set to 40 nm.

Further, a 7mDBTPDBq-II film was formed to a thickness of 10 nm over the light-emitting layer 1113, so that a first electron-transport layer 1114a was formed.

Then, a film of bathophenanthroline (abbreviation: BPhen) was formed to a thickness of 20 nm over the first electron-transport layer 1114a, so that a second electron-transport layer 1114b was formed.

Further, a film of lithium fluoride (LiF) was formed to a thickness of 1 nm over the second electron-transport layer 1114b using evaporation, so that an electron-injection layer 1115 was formed.

Lastly, an aluminum film was formed to a thickness of 200 nm using evaporation as the second electrode 1103 functioning as a cathode. Thus, the light-emitting element 1 of this example was fabricated.

Note that, in the above evaporation process, a resistance heating method was used for evaporation.

(Comparison Light-Emitting Element 2)

The light-emitting layer 1113 of the comparison light-emitting element 2 was formed by co-evaporation of 2-phenyldibenzo[f,h]quinoxaline (abbreviation: 2PDBq) and [Ir(mppr-Me)$_2$(acac)]. The weight ratio of 2PDBq to [Ir(mppr-Me)$_2$(acac)] was adjusted to 1:0.06 (=2PDBq:[Ir(mppr-Me)$_2$(acac)]). The thickness of the light-emitting layer 1113 was set to 40 nm.

A 2PDBq film was formed to a thickness of 10 nm, so that the first electron-transport layer 1114a of the comparison light-emitting element 2 was formed. The components other than the light-emitting layer 1113 and the first electron-transport layer 1114a were formed in the same way as those of the light-emitting element 1.

Element structures of the light-emitting element 1 and the comparison light-emitting element 2 obtained as described above is shown in Table 1.

As shown in Table 2, the CIE chromaticity coordinates of the light-emitting element 1 were (x, y)=(0.54, 0.45) at a luminance of 670 cd/m$^2$. Further, the CIE chromaticity coordinates of the comparison light-emitting element 2 were (x, y)=(0.52, 0.47) at a luminance of 1000 cd/m$^2$. It is found

TABLE 1

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 1 | ITSO 110 nm | BPAFLP:MoOx (=4:2) 40 nm | BPAFLP 20 nm | 7mDBTPDBq-II:[Ir(mppr-Me)$_2$(acac)] (=1:0.06) 40 nm | 7mDBTPDBq-II 10 nm | BPhen 20 nm | LiF 1 nm | Al 200 nm |
| Comparison light-emitting element 2 | ITSO 110 nm | BPAFLP:MoOx (=4:2) 40 nm | BPAFLP 20 nm | 2PDBq:[Ir(mppr-Me)$_2$(acac)] (=1:0.06) 40 nm | 2PDBq 10 nm | BPhen 20 nm | LiF 1 nm | Al 200 nm |

In a glove box containing a nitrogen atmosphere, the light-emitting element 1 and the comparison light-emitting element 2 were sealed with a glass substrate so as not to be exposed to the air. Then, operation characteristics of these elements were measured. Note that the measurements were carried out at room temperature (in the atmosphere kept at 25° C.).

Figure 10:
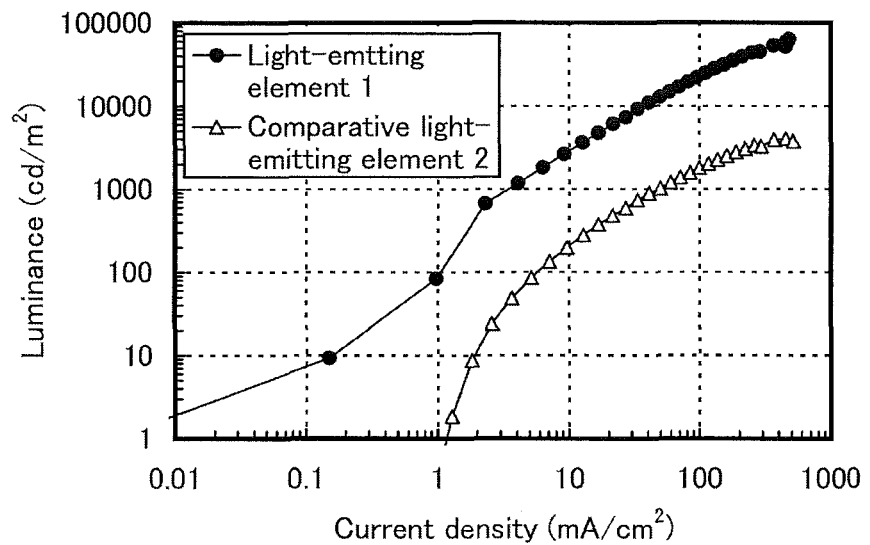
FIG. 10 shows luminance versus current density characteristics of light-emitting elements of Example 2.
Figure 11:
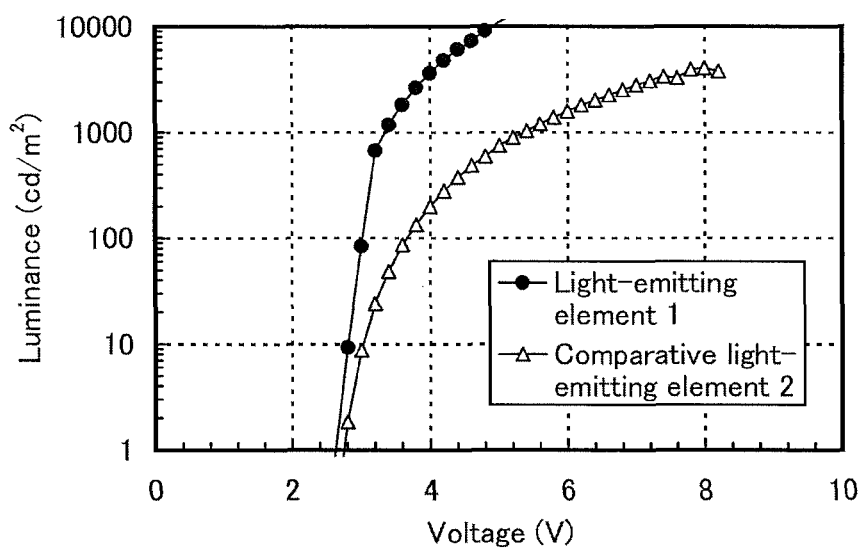
FIG. 11 shows luminance versus voltage characteristics of the light-emitting elements of Example 2.
Figure 12:
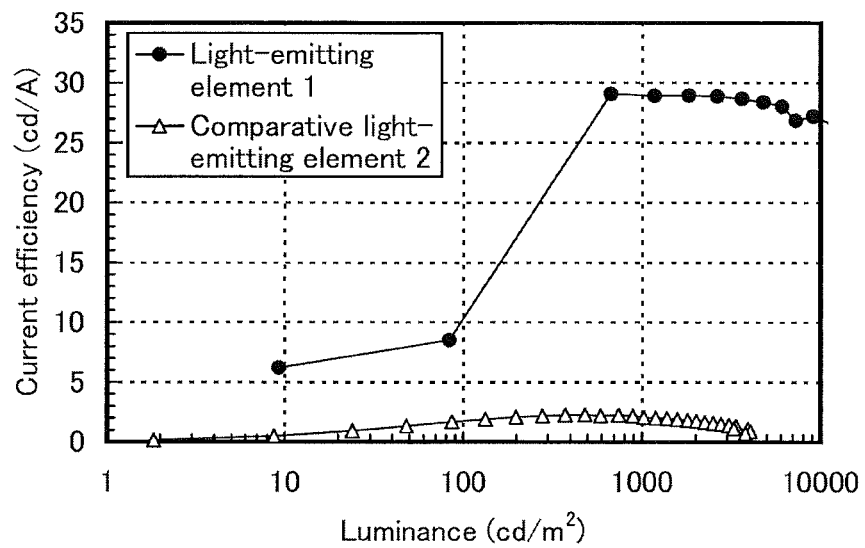
FIG. 12 shows current efficiency versus luminance characteristics of the light-emitting elements of Example 2.
Figure 13:
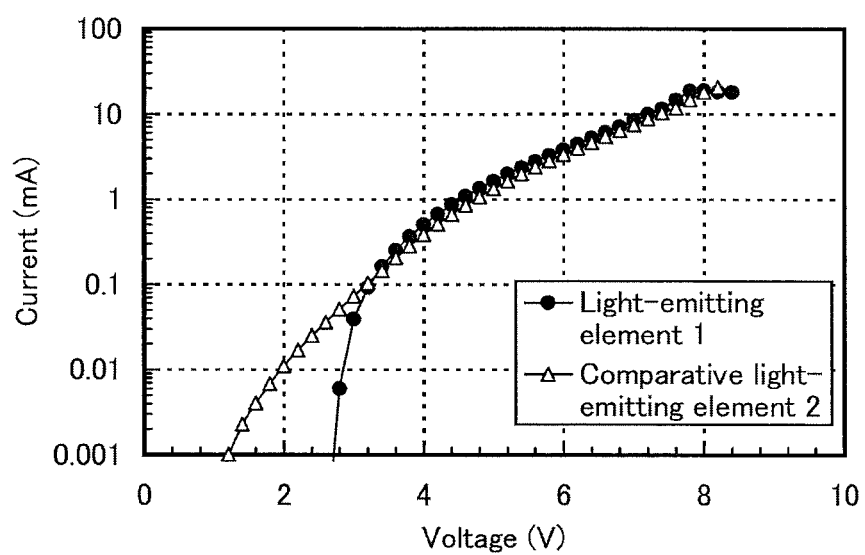
FIG. 13 shows current versus voltage characteristics of the light-emitting elements of Example 2.

Luminance versus current density characteristics of the light-emitting element 1 and the comparison light-emitting element 2 are shown in FIG. 10. In FIG. 10, the horizontal axis represents current density (mA/cm$^2$) and the vertical axis represents luminance (cd/m$^2$). Further, luminance versus voltage characteristics of the elements are shown in FIG. 11. In FIG. 11, the horizontal axis represents voltage (V) and the vertical axis represents luminance (cd/m$^2$). In addition, current efficiency versus luminance characteristics of the elements are shown in FIG. 12. In FIG. 12, the horizontal axis represents luminance (cd/m$^2$) and the vertical axis represents current efficiency (cd/A). Further, current versus voltage characteristics of the elements are shown in FIG. 13. In FIG. 13, the horizontal axis represents voltage (V) and the vertical axis represents current (mA). Further, Table 2 shows the voltage (V), current density (mA/cm$^2$), CIE chromaticity coordinates (x, y), current efficiency (cd/A), and external quantum efficiency (%) of the light-emitting elements at a luminance of around 1000 cd/m$^2$.

that light emission originating from [Ir(mppr-Me)$_2$(acac)] was obtained from each of the light-emitting element 1 and the comparison light-emitting element 2.

As can be seen from FIG. 13, in a region at a lower voltage than the voltage (of about 2V) at which light emission starts, a larger current flows in the comparison light-emitting element 2 fabricated in this example than in the light-emitting element 1. In addition, Table 2 indicates that the current efficiency of the comparison light-emitting element 2 is significantly low. This is considered to be because 2PDBq used for the light-emitting layer 1113 of the comparison light-emitting element 2 was crystallized and current leakage occurred.

As can be seen from FIG. 10, FIG. 11, FIG. 12, and FIG. 13 the light-emitting element 1 has low driving voltage and high current efficiency. It is thus confirmed that a compound to which one embodiment of the present invention is applied is effective in realizing excellent voltage versus luminance characteristics and excellent luminance versus current efficiency characteristics.

As described above, by using 7mDBTPDBq-II for a host material of a light-emitting layer and for an electron-transport layer, a light-emitting element having low driving voltage and high current efficiency was able to be fabricated.

Example 3

Synthesis Example 2

This example illustrates a method of synthesizing 7-[3'-(dibenzothiophen-4- yl)biphenyl-3-yl]dibenzo[f,h]quinoxa-

TABLE 2

| | Voltage (V) | Current density (mA/cm$^2$) | Chromaticity x | Chromaticity y | Luminance (cd/m$^2$) | Current efficiency (cd/A) | External quantum efficiency (%) |
|---|---|---|---|---|---|---|---|
| Light-emitting element 1 | 3.2 | 2.3 | 0.54 | 0.45 | 670 | 29 | 11 |
| Comparison light-emitting element 2 | 5.4 | 50 | 0.52 | 0.47 | 1000 | 2.0 | 0.7 | line (abbreviation: 7mDBTBPDBq-II) represented by the structural formula (109) in Embodiment 1. A structure of 7mDBTBPDBq-II is illustrated below.

[Chemical Formula 62]

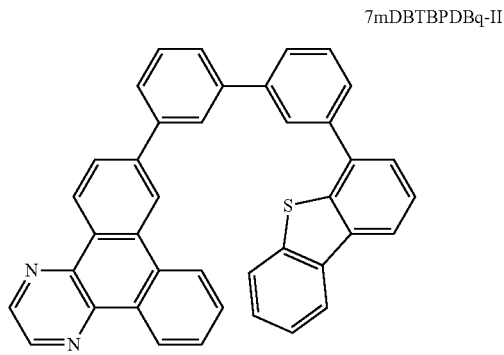

7mDBTBPDBq-II

A scheme for the synthesis of 7mDBTBPDBq-II is illustrated in (D-1).

[Chemical Formula 63]

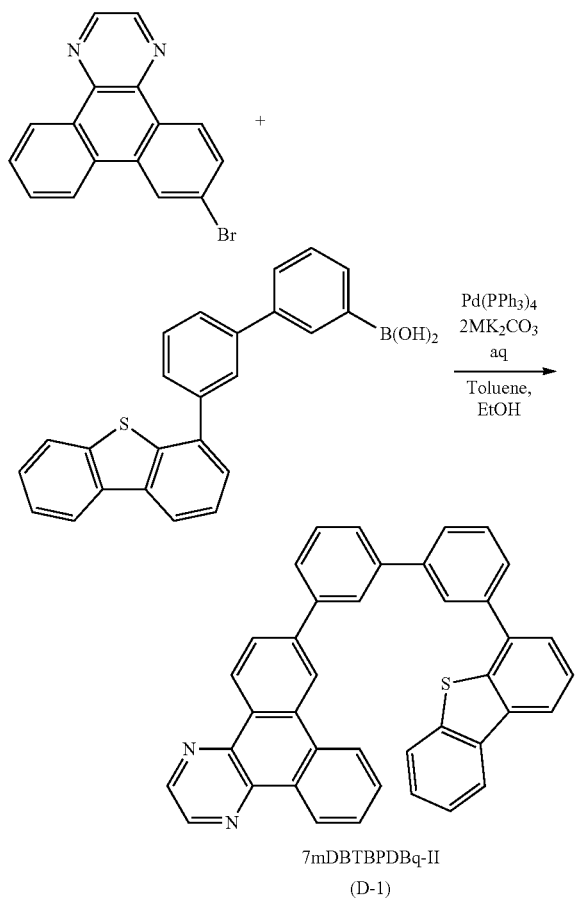

7mDBTBPDBq-II (D-1)

In a 100 mL three-neck flask were put 0.71 g (2.3 mmol) of 7-bromodibenzo[f,h]quinoxaline, 1.0 g (2.5 mmol) of 3-[3-(dibenzothiophen-4-yl)phenyl]phenylboronic acid, 30 mL of toluene, 3 mL of ethanol, and 3.5 mL of a 2M aqueous solution of potassium carbonate. This mixture was degassed by being stirred under reduced pressure, and the air in the flask was replaced with nitrogen. To this mixture was added 53 mg (46 μmol) of tetrakis(triphenylphosphine)palladium (0). This mixture was stirred at 80° C. for 18 hours under a nitrogen stream. Water was added to this mixture, and a solid precipitated in the system was collected by suction filtration to give a solid. Further, organic substances were extracted from the aqueous layer of the obtained filtrate with toluene. The solution of the obtained extract and the organic layer were combined and washed with an aqueous solution of sodium hydrogen carbonate and saturated brine, and the organic layer was dried over magnesium sulfate. The obtained mixture was gravity-filtered, and the filtrate was concentrated to give a solid. A toluene solution of these solids was suction-filtered through Celite (produced by Wako Pure Chemical Industries, Ltd., Catalog No. 531-16855) and alumina, and the filtrate was concentrated to give a solid. The obtained solid was purified by silica gel column chromatography (toluene:hexane=2:1), and further, recrystallization from toluene gave 0.70 g of a pale yellow powder in 53% yield, which was the object of the synthesis.

By a train sublimation method, 0.70 g of the obtained pale yellow powder was purified. In the sublimation purification, the pale yellow powder was heated at 280° C. for 20 hours under a pressure of 3.1 Pa with a flow rate of argon gas of 5 mL/min. After the sublimation purification, 0.62 g of a pale yellow powder which was the object of the synthesis was recovered in a yield of 88%.

Nuclear magnetic resonance (NMR) spectroscopy identified this compound as 7-[3'-(dibenzothiophen-4-yl)biphenyl-3-yl]dibenzo[f,h]quinoxaline (abbreviation: 7mDBTBPDBq-II), which was the object of the synthesis.

$^1$H NMR data of the obtained compound are as follows: $^1$H NMR (CDCl$_3$, 300 MHz): δ=7.42-7.51 (m, 2H), 7.58-7.69 (m, 4H), 7.74-7.85 (m, 7H), 8.05 (dd, J=8.1 Hz, 1.5 Hz, 1H), 8.12-8.13 (m, 2H), 8.17-8.22 (m, 2H), 8.73-8.76 (m, 1H), 8.90-8.93 (m, 3H), 9.23-9.28 (m, 1H), 9.31 (d, J=8.4 Hz, 1H).

Figure 15A:
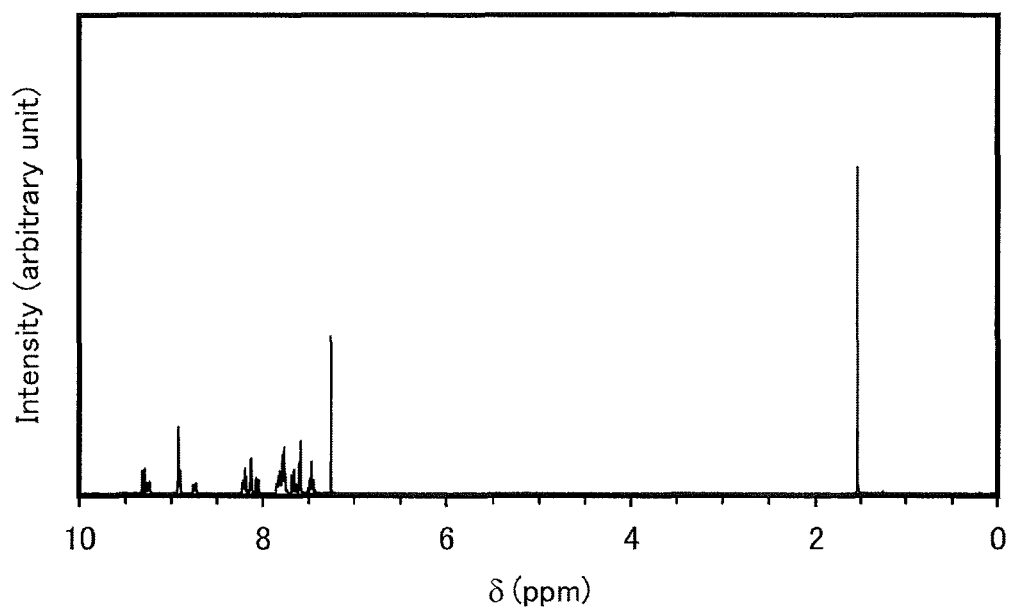
FIGS. 15A and 15B show $^1$H NMR charts of 7-[3'-(dibenzothiophen-4-yl)biphenyl-3-yl]dibenzo[f,h]quinoxaline (abbreviation: 7mDBTBPDBq-II)
Figure 15B:
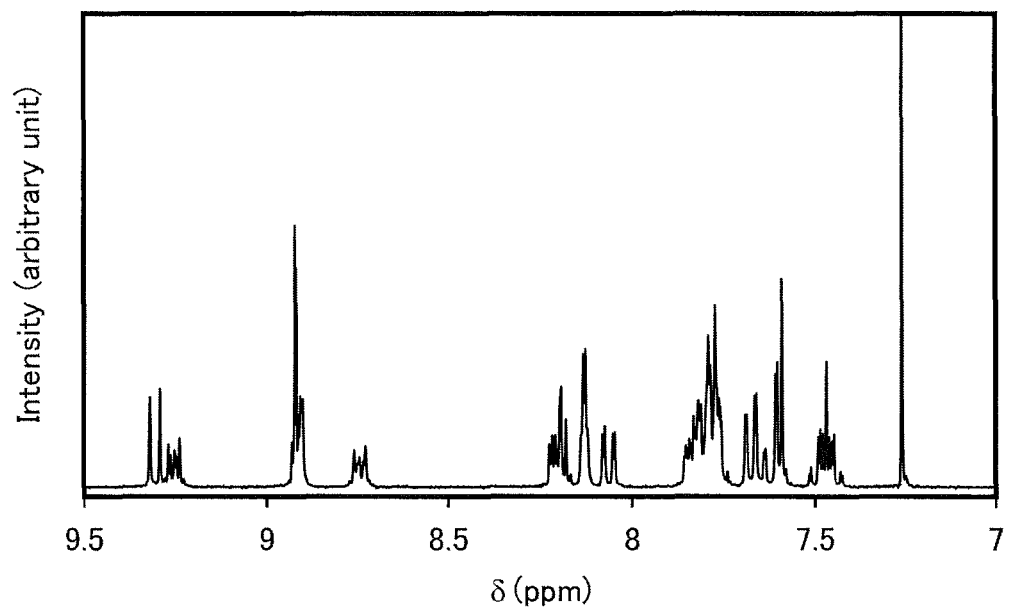

Further, $^1$H NMR charts are shown in FIGS. 15A and 15B. Note that FIG. 15B is a chart where the range of from 7.0 ppm to 9.5 ppm in FIG. 15A is enlarged.

Figure 16A:
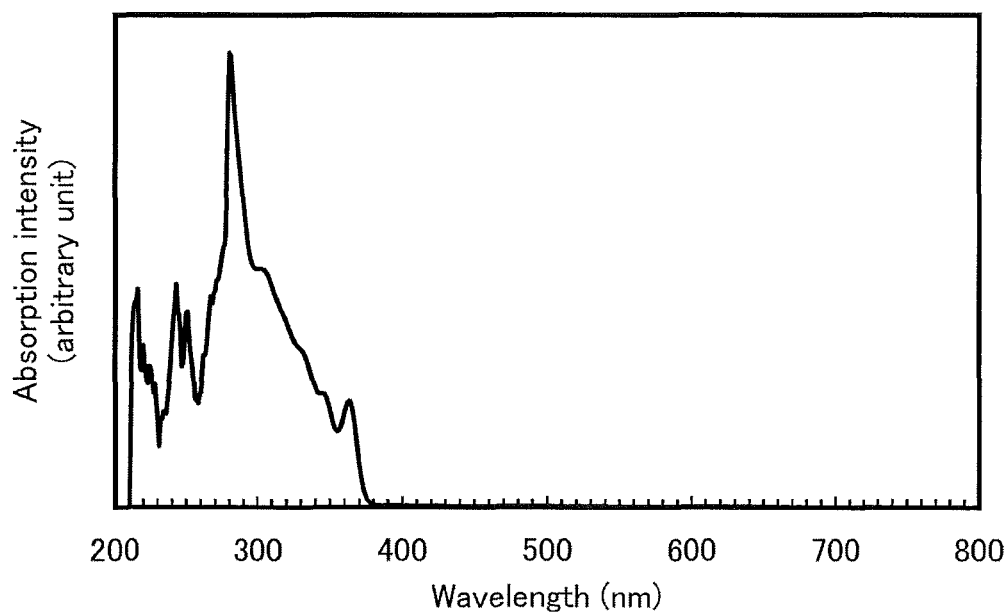
FIGS. 16A and 16B show an absorption and emission spectra of 7mDBTBPDBq-II in a toluene solution of 7mDBTBPDBq-II.
Figure 16B:
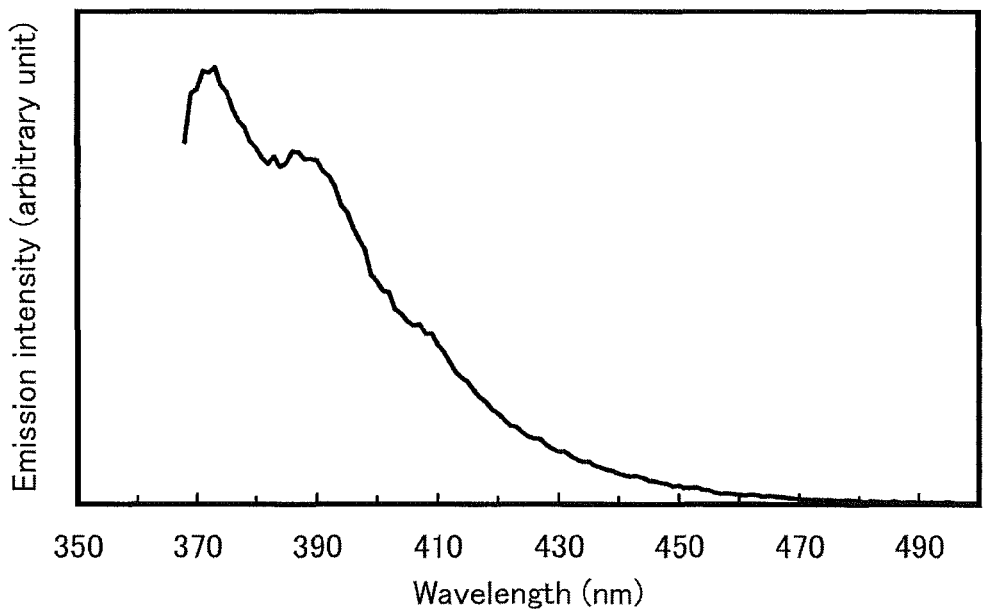
Figure 17A:
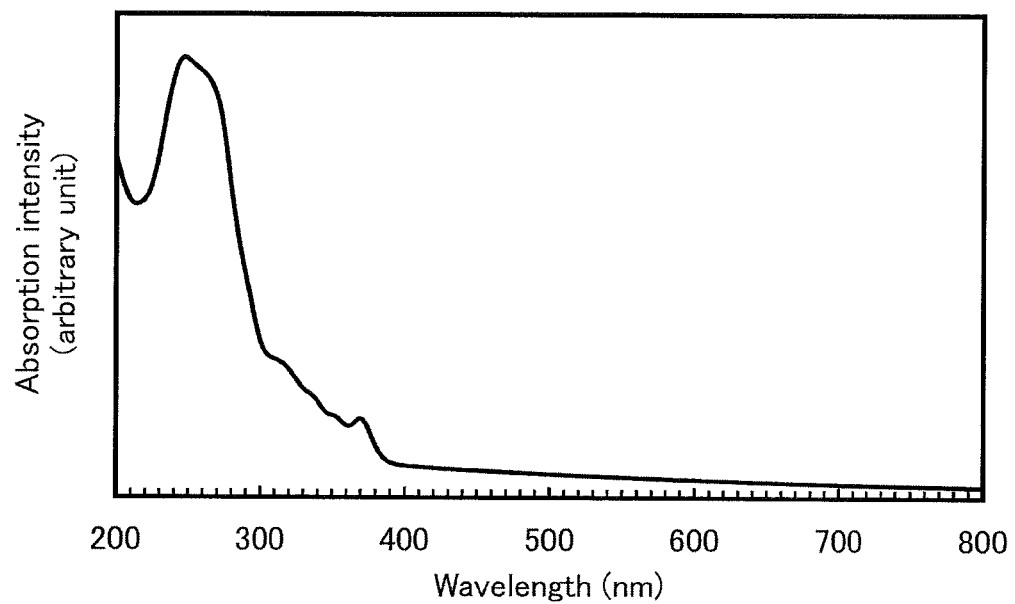
FIGS. 17A and 17B show an absorption and emission spectra of a thin film of 7mDBTBPDBq-II.
Figure 17B:
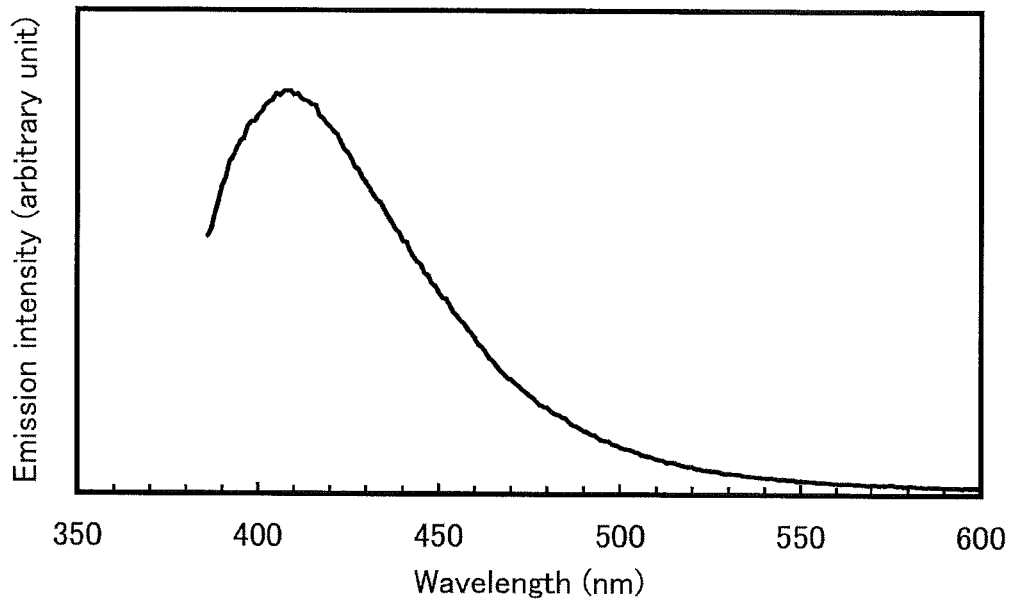

Further, FIG. 16A shows an absorption spectrum of 7mDBTBPDBq-II in a toluene solution of 7mDBTBPDBq-II, and FIG. 16B shows an emission spectrum thereof. Furthermore, FIG. 17A shows an absorption spectrum of a thin film of 7mDBTBPDBq-II, and FIG. 17B shows an emission spectrum thereof. The absorption spectrum was measured using an ultraviolet-visible spectrophotometer (V-550, produced by JASCO Corporation). The measurements were performed with samples prepared in such a way that the solution was put in a quartz cell and the thin film was obtained by evaporation onto a quartz substrate. The figures show the absorption spectrum of the solution which was obtained by subtracting the absorption spectra of quartz and toluene from the absorption spectra of quartz and the solution, and the absorption spectrum of the thin film which was obtained by subtracting the absorption spectrum of a quartz substrate from the absorption spectra of the quartz substrate and the thin film. In FIG. 16A and FIG. 17A, the horizontal axis represents wavelength (nm) and the vertical axis represents absorption intensity (arbitrary unit). In FIG. 16B and FIG. 17B, the horizontal axis represents wavelength (nm) and the vertical axis represents emission intensity (arbitrary unit). In the case of the toluene solution, absorption peaks were observed at around 281 nm, 303 nm, and 363 nm, and emission wavelength peaks were 372 nm and 387 nm (at an excitation wavelength of 364 nm). In the case of the thin film, absorption peaks were observed at around 247 nm, 260 nm, 312 nm, 331 nm, 351 nm and 370 nm, and an emission wavelength peak was 408 nm (at an excitation wavelength of 370 nm).

Example 4

In this example, a light-emitting element according to one embodiment of the present invention is described referring to FIG. 6. Chemical formulae of materials used in this example are illustrated below. Note that the chemical formulae of the materials which are illustrated above are omitted.

[Chemical Formula 64]

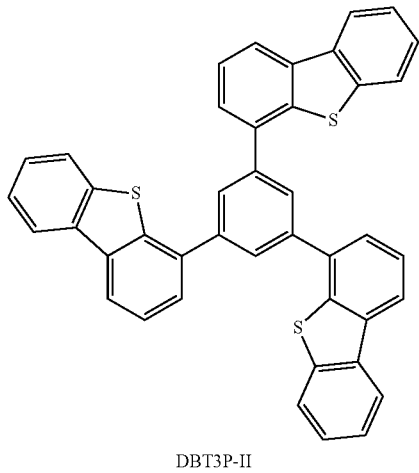

DBT3P-II

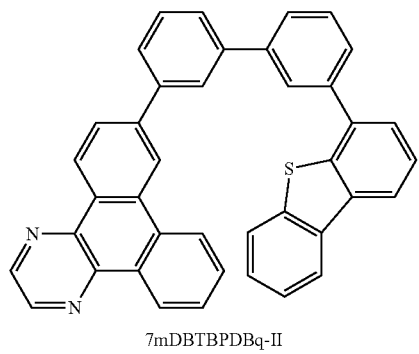

7mDBTBPDBq-II

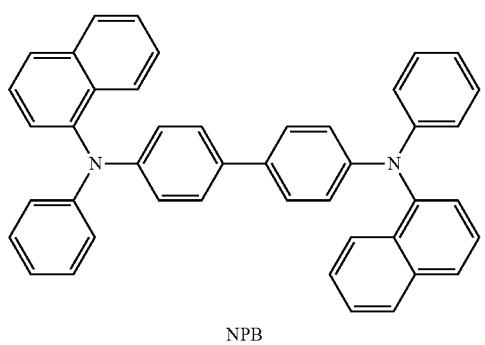

NPB

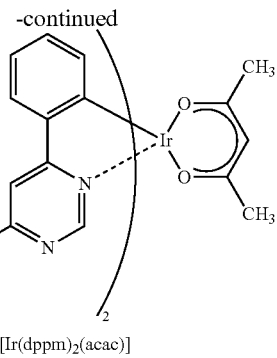

[Ir(dppm)$_2$(acac)]

The way how a light-emitting element 3 of this example was fabricated is described hereinbelow.

(Light-Emitting Element 3)

First, an ITSO film was formed over the glass substrate 1100 by a sputtering method, so that the first electrode 1101 was formed. Note that its thickness was set to 110 nm and the electrode area was set to 2 mm×2 mm. Here, the first electrode 1101 is an electrode that functions as an anode of the light-emitting element.

In pretreatment for forming the light-emitting elements over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Then, the substrate 1100 over which the first electrode 1101 was formed was fixed to a substrate holder provided in a vacuum evaporation apparatus so that the surface on which the first electrode 1101 was formed faced downward. The pressure in the vacuum evaporation apparatus was reduced to about $10^{-4}$ Pa. After that, over the first electrode 1101, 4,4',4''-(1,3,5-benzenetriyl)tri(dibenzothiophene) (abbreviation: DBT3P-II) and molybdenum(VI) oxide were co-evaporated by an evaporation method using resistance heating, so that the hole-injection layer 1111 was formed. The thickness of the hole-injection layer 1111 was set to 40 nm, and the weight ratio of DBT3P-II to molybdenum oxide was adjusted to 4:2 (=DBT3P-II:molybdenum oxide).

Next, over the hole-injection layer 1111, a BPAFLP film was formed to a thickness of 20 nm, so that the hole-transport layer 1112 was formed.

Further, 7-[3'-(dibenzothiophen-4-yl)biphenyl-3-yl] dibenzo[f,h]quinoxaline (abbreviation: 7mDBTBPDBq-II) synthesized in Example 3,4,4'-bis[N-(1-naphthyl)-N-phenylamino]biphenyl (abbreviation: NPB), and (acetylacetonato)bis(4,6-diphenylpyrimidinato)iridium(III) (abbreviation: [Ir(dppm)$_2$(acac)]) were co-evaporated to form the light-emitting layer 1113 over the hole-transport layer 1112. The weight ratio of 7mDBTBPDBq-II to NPB and [Ir(dppm)$_2$(acac)] was adjusted to 0.8:0.2:0.05 (=7mDBTBP-DBq-II:NPB:[Ir(dppm)$_2$(acac)]). The thickness of the light-emitting layer 1113 was set to 40 nm.

Further, a 7mDBTBPDBq-II film was formed to a thickness of 10 nm over the light-emitting layer 1113, so that the first electron-transport layer 1114a was formed.

Then, a BPhen film was formed to a thickness of 20 nm over the first electron-transport layer 1114a, so that the second electron-transport layer 1114b was formed.

Further, a LiF film was formed to a thickness of 1 nm over the second electron-transport layer 1114b using evaporation, so that the electron-injection layer 1115 was formed.

Lastly, an aluminum film was formed to a thickness of 200 nm using evaporation as the second electrode 1103 functioning as a cathode. Thus, the light-emitting element 3 of this example was fabricated.

Note that, in the above evaporation process, a resistance heating method was used for evaporation.

An element structure of the light-emitting element 3 obtained as described above is shown in Table 3.

As shown in Table 4, the CIE chromaticity coordinates of the light-emitting element 3 were (x, y)=(0.57, 0.43) at a luminance of 850 cd/m². It is found that light emission originating from [Ir(dppm)₂(acac)] was obtained from the light-emitting element 3.

As can be seen from FIG. 18, FIG. 19, FIG. 20, FIG. 21, and Table 4, the light-emitting element 3 has low driving voltage, high current efficiency, and high external quantum efficiency. It is thus confirmed that a compound to which one embodiment of the present invention is applied is effective in realizing excellent voltage versus luminance characteristics and excellent luminance versus current efficiency characteristics.

TABLE 3

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 3 | ITSO 110 nm | DBT3P-II:MoOx (=4:2) 40 nm | BPAFLP 20 nm | 7mDBTBPDBq-II:NPB:[Ir(dppm)₂(acac)] (=0.8:0.2:0.05) 40 nm | 7mDBTBPDBq-II 10 nm | BPhen 20 nm | LiF 1 nm | Al 200 nm |

In a glove box containing a nitrogen atmosphere, the light-emitting element 3 was sealed with a glass substrate so as not to be exposed to the air. Then, operation characteristics of the element were measured. Note that the measurements were carried out at room temperature (in the atmosphere kept at 25° C.).

Figure 18:
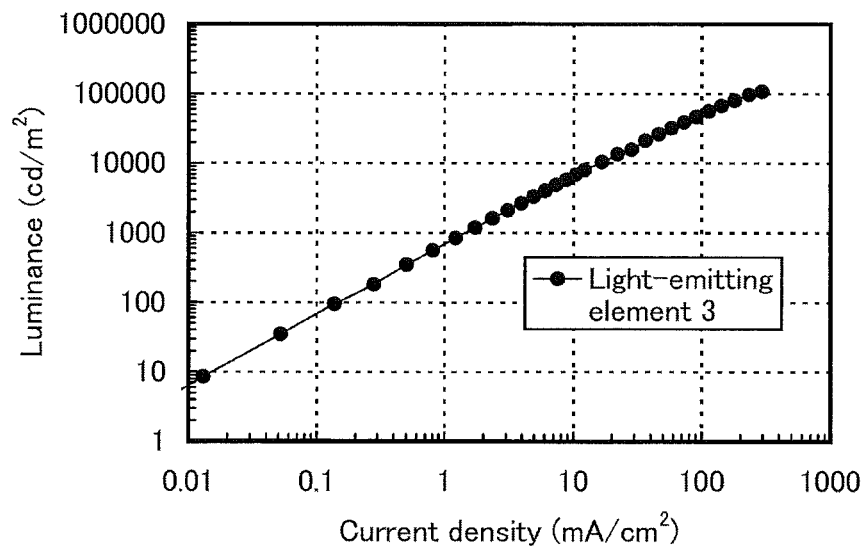
FIG. 18 shows luminance versus current density characteristics of a light-emitting element of Example 4.
Figure 19:
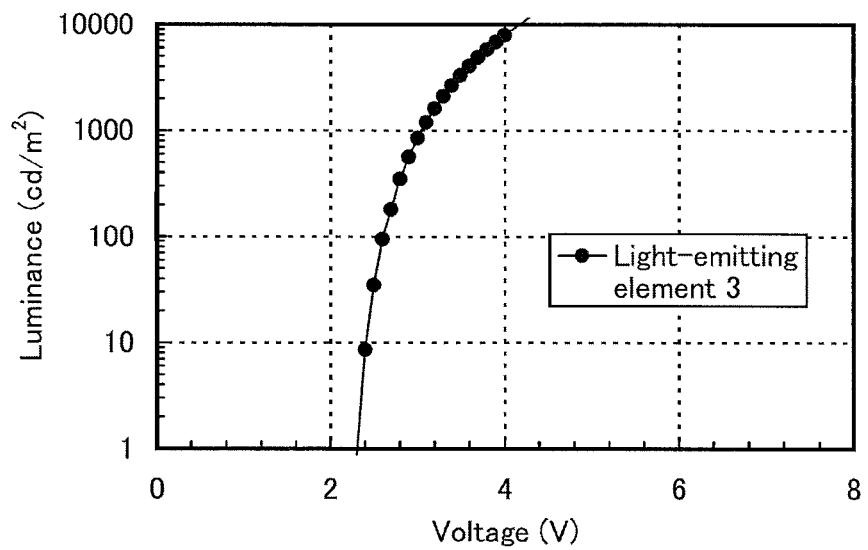
FIG. 19 shows luminance versus voltage characteristics of the light-emitting element of Example 4.
Figure 20:
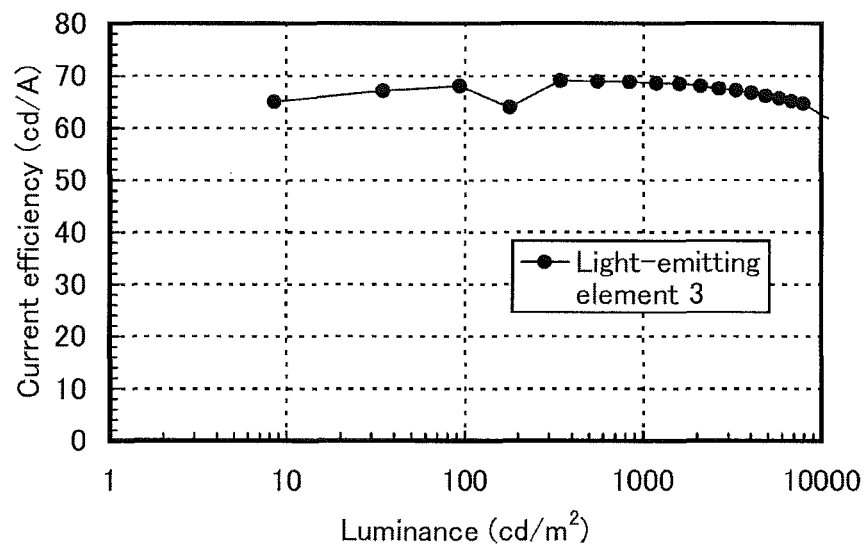
FIG. 20 shows current efficiency versus luminance characteristics of the light-emitting element of Example 4.
Figure 21:
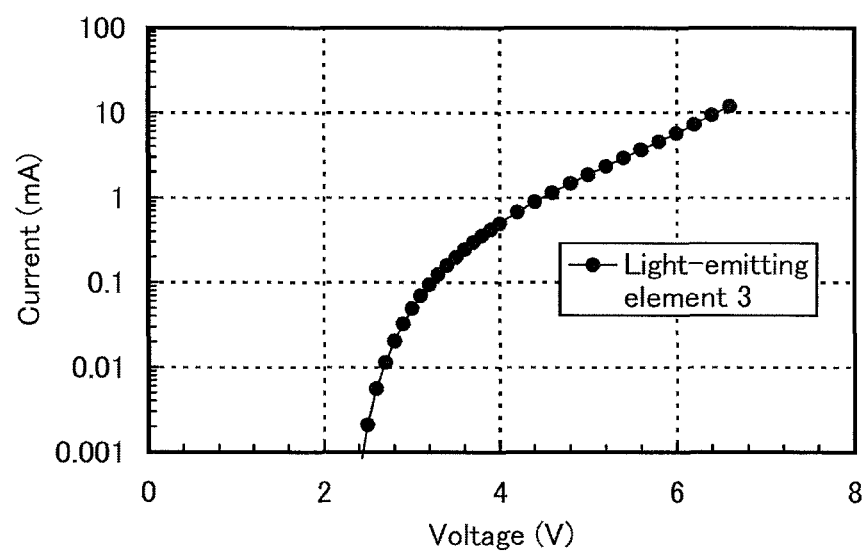
FIG. 21 shows current versus voltage characteristics of the light-emitting element of Example 4.

Luminance versus current density characteristics of the light-emitting element 3 are shown in FIG. 18. In FIG. 18, the horizontal axis represents current density (mA/cm²) and the vertical axis represents luminance (cd/m²). Further, luminance versus voltage characteristics of the element are shown in FIG. 19. In FIG. 19, the horizontal axis represents voltage (V) and the vertical axis represents luminance (cd/m²). In addition, current efficiency versus luminance characteristics of the element are shown in FIG. 20. In FIG. 20, the horizontal axis represents luminance (cd/m²) and the vertical axis represents current efficiency (cd/A). Further, current versus voltage characteristics of the element are shown in FIG. 21. In FIG. 21, the horizontal axis represents voltage (V) and the vertical axis represents current (mA). Further, Table 4 shows the voltage (V), current density (mA/cm²), CIE chromaticity coordinates (x, y), current efficiency (cd/A), and external quantum efficiency (%) of the light-emitting element 3 at a luminance of 850 cd/m².

As described above, by using 7mDBTBPDBq-II for a host material of a light-emitting layer and for an electron-transport layer, a light-emitting element having low driving voltage, high current efficiency, and high external quantum efficiency was able to be fabricated.

Figure 22:
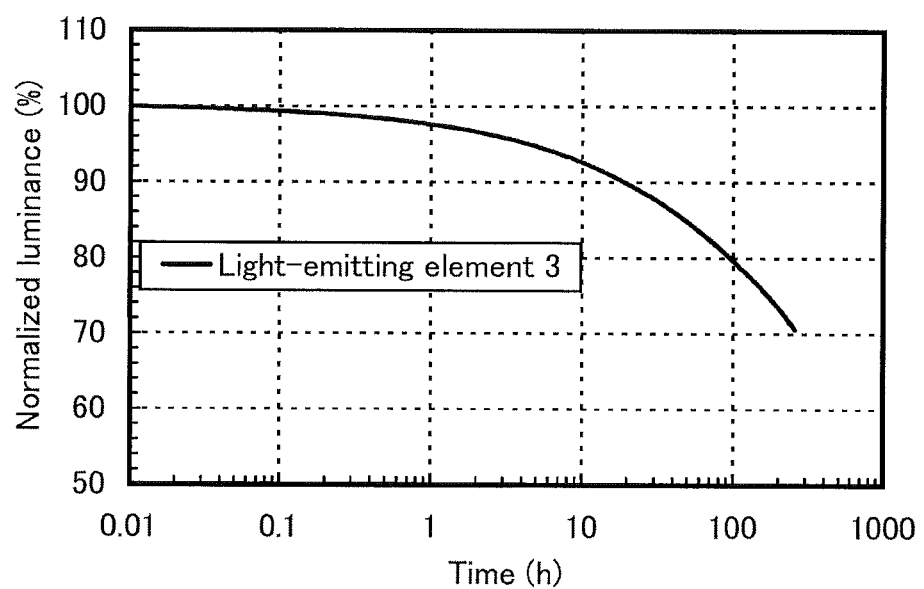
FIG. 22 shows results of the reliability test of the light-emitting element of Example 4.

Next, the light-emitting element 3 was subjected to a reliability test. Results of the reliability test are shown in FIG. 22. In FIG. 22, the vertical axis represents normalized luminance (%) with an initial luminance of 100%, and the horizontal axis represents driving time (h) of the element.

In the reliability test, the light-emitting element 3 was driven under the conditions where the initial luminance was set to 5000 cd/m² and the current density was constant.

The light-emitting element 3 kept 71% of the initial luminance after 260 hours elapsed.

The above results suggest that an element having high reliability and a long lifetime can be realized by using 7mDBTBPDBq-II for the host material of the light-emitting layer and for the electron-transport layer.

Reference Example

This example specifically illustrates a method of synthesizing (acetylacetonato)bis(4,6-diphenylpyrimidinato) iridium(III) (abbreviation: [Ir(dppm)₂(acac)]) used in the above example. A structure of [Ir(dppm)₂(acac)] is illustrated below.

TABLE 4

| | Voltage (V) | Current density (mA/cm²) | Chromaticity x | Chromaticity y | Luminance (cd/m²) | Current efficiency (cd/A) | External quantum efficiency (%) |
|---|---|---|---|---|---|---|---|
| Light-emitting element 3 | 3.0 | 1.2 | 0.57 | 0.43 | 850 | 69 | 28 |

[Chemical Formula 65]

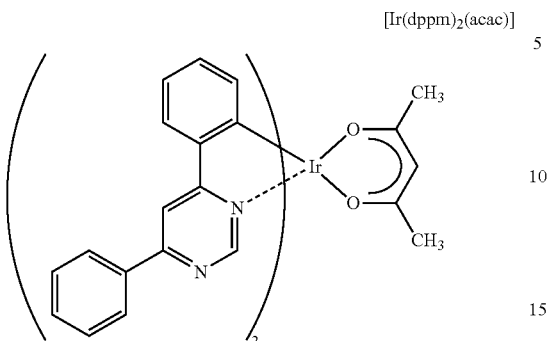

[Ir(dppm)₂(acac)]

Step 1: Synthesis of 4,6-Diphenylpyrimidine (abbreviation: Hdppm)

First, in a recovery flask equipped with a reflux pipe were put 5.02 g of 4,6-dichloropyrimidine, 8.29 g of phenylboronic acid, 7.19 g of sodium carbonate, 0.29 g of bis(triphenylphosphine)palladium(II) dichloride (abbreviation: Pd(PPh₃)₂Cl₂), 20 mL of water, and 20 mL of acetonitrile, and the air in the flask was replaced with argon. This reaction container was subjected to irradiation with microwaves (2.45 GHz, 100 W) for 60 minutes so that heating was performed. Here, in the flask were further put 2.08 g of phenylboronic acid, 1.79 g of sodium carbonate, 0.070 g of Pd(PPh₃)₂Cl₂, 5 mL of water, and 5 mL of acetonitrile, and the mixture was subjected to irradiation with microwaves (2.45 GHz, 100 W) for 60 minutes so that heating was performed. After that, water was added to this solution and an organic layer was subjected to extraction with dichloromethane. The solution of the obtained extract was washed with water and dried over magnesium sulfate. After the drying, the solution was filtered. The solvent of this solution was distilled off, and then the obtained residue was purified by silica gel column chromatography using dichloromethane as a developing solvent. As a result, a pyrimidine derivative, Hdppm was obtained (yellow white powder, 38% yield). Note that for the microwave irradiation, a microwave synthesis system (Discover, produced by CEM Corporation) was used. A synthesis scheme (x-1) of Step 1 is illustrated below.

[Chemical Formula 66]

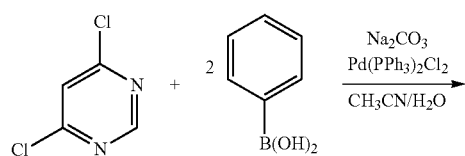

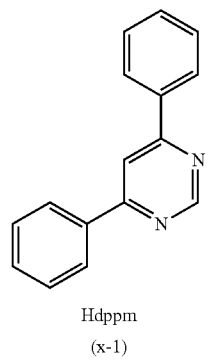

Hdppm
(x-1)

Step 2: Synthesis of Di-μ-chloro-bis[bis(4,6-diphenylpyrimidinato)iridium(III)] (abbreviation: [Ir(dppm)₂Cl]₂)

Next, in a recovery flask equipped with a reflux pipe were put 15 mL of 2-ethoxyethanol, 5 mL of water, 1.10 g of Hdppm obtained in Step 1 above, and 0.69 g of iridium chloride hydrate (IrCl₃·H₂O), and the air in the flask was replaced with argon. After that, irradiation with microwaves (2.45 GHz, 100 W) was performed for one hour to cause a reaction. After the solvent was distilled off, and the obtained residue was filtered with ethanol and washed to give a dinuclear complex, [Ir(dppm)₂Cl]₂ was obtained (red-brown brown powder, 88% yield). A synthesis scheme (x-2) of Step 2 is illustrated below.

[Chemical Formula 67]

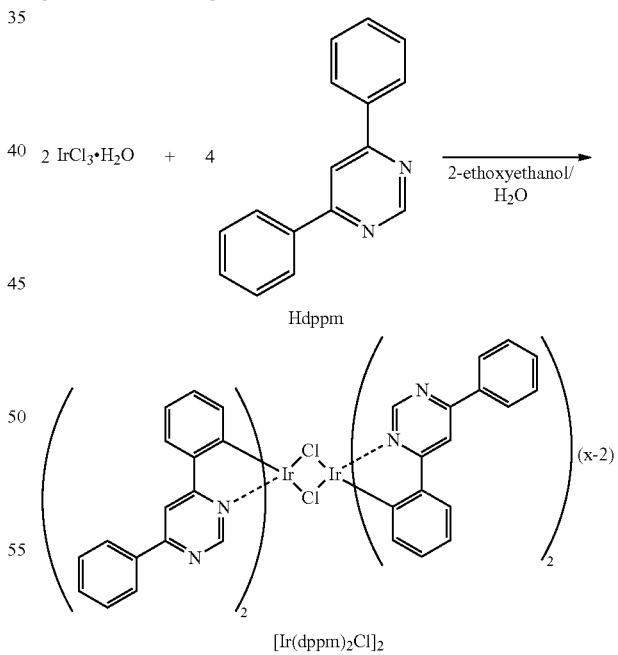

Step 3: Synthesis of (Acetylacetonato)bis(4,6-diphenylpyrimidinato)iridium(III) (abbreviation: [Ir(dppm)₂(acac)])

Furthermore, in a recovery flask equipped with a reflux pipe were put 40 mL of 2-ethoxyethanol, 1.44 g of

[Ir(dppm)₂Cl]₂ obtained in Step 2 above, 0.30 g of acetylacetone, and 1.07 g of sodium carbonate, and the air in the flask was replaced with argon. After that, irradiation with microwaves (2.45 GHz, 120 W) was performed for 60 minutes to cause a reaction. The solvent was distilled off, the obtained residue was dissolved in dichloromethane, and filtration was performed to remove an insoluble portion. The obtained filtrate was washed with water and then with saturated brine, and was dried over magnesium sulfate. After the drying, the solution was filtered. The solvent of this solution was distilled off, and then the obtained residue was purified by silica gel column chromatography using dichloromethane and ethyl acetate in a volume ratio of 50:1 as a developing solvent. After that, recrystallization was carried out with a mixed solvent of dichloromethane and hexane to give an orange powder that was the object of the synthesis (32% yield). A synthesis scheme (x-3) of Step 3 is illustrated below.

[Chemical Formula 68]

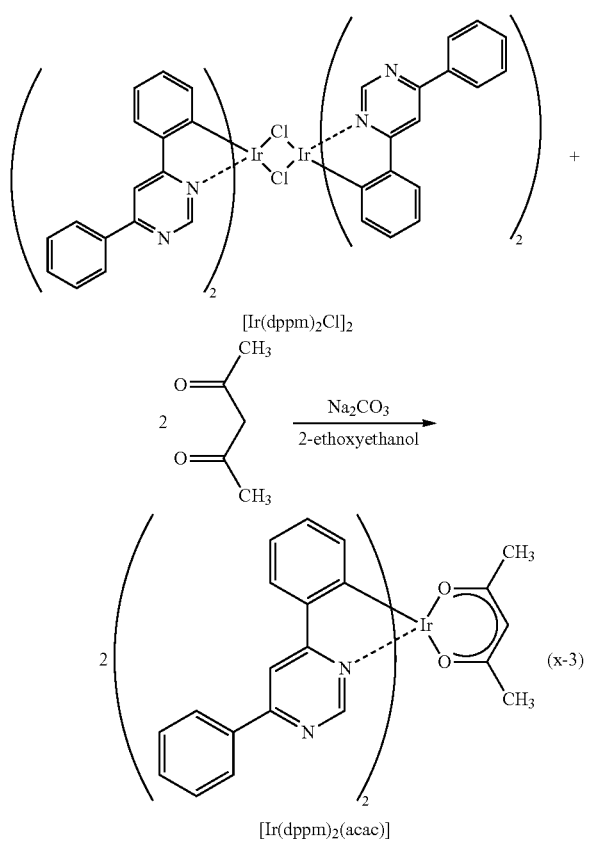

The results of nuclear magnetic resonance (¹H NMR) spectroscopy, by which the orange powder obtained in Step 3 above was analyzed, are shown below. The results show that [Ir(dppm)₂(acac)] was obtained.

¹H NMR. δ (CDCl₃): 1.83 (s, 6H), 5.29 (s, 1H), 6.48 (d, 2H), 6.80 (t, 2H), 6.90 (t, 2H), 7.55-7.63 (m 6H), 7.77 (d, 2H), 8.17 (s, 2H), 8.24 (d, 4H), 9.17 (s, 2H).

This application is based on Japanese Patent Application Serial No. 2011-020113 filed with the Japan Patent Office on Feb. 1, 2011 and Japanese Patent Application Serial No. 2011-181467 filed with the Japan Patent Office on Aug. 23, 2011, the entire contents of which are hereby incorporated by reference.

What is claimed is:

1. A compound represented by a general formula (G1),

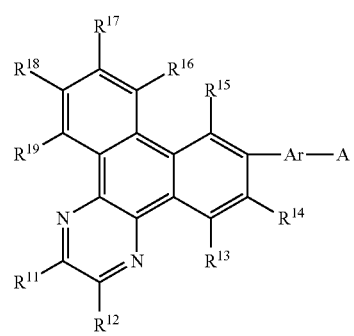

(G1)

wherein:
A represents any one of a substituted or unsubstituted dibenzothiophenyl group and a substituted or unsubstituted dibenzofuranyl group;
$R^{11}$ to $R^{19}$ separately represent any one of hydrogen, an alkyl group having 1 to 4 carbon atoms, and a substituted or unsubstituted aryl group having 6 to 13 carbon atoms; and
Ar represents a substituted or unsubstituted arylene group having 6 to 13 carbon atoms.

2. A compound represented by a general formula (G2-1),

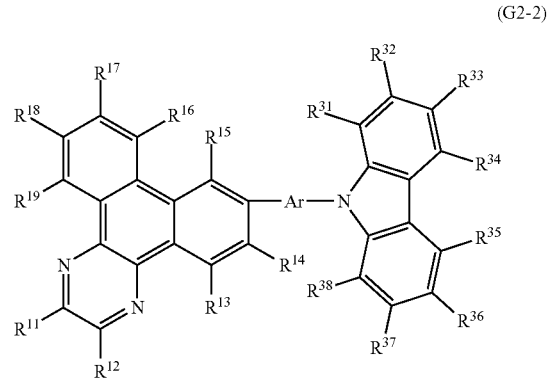

(G2-2)

wherein:
$Q^1$ represents any one of a sulfur atom, an oxygen atom, and a nitrogen atom;
$R^{11}$ to $R^{19}$ and $R^{21}$ to $R^{27}$ separately represent any one of hydrogen, an alkyl group having 1 to 4 carbon atoms, and a substituted or unsubstituted aryl group having 6 to 13 carbon atoms; and
Ar represents a substituted or unsubstituted arylene group having 6 to 13 carbon atoms.

3. The compound according to claim 2, wherein the nitrogen atom has an alkyl group having 1 to 4 carbon atoms, or a substituted or unsubstituted aryl group having 6 to 13 carbon atoms.

4. The compound according to claim 2, wherein Ar is a substituted or unsubstituted phenylene group or a substituted or unsubstituted biphenyldiyl group.

5. The compound according to claim 2, wherein Ar is a substituted or unsubstituted m-phenylene group.

6. The compound according to claim 2,
wherein:
the compound is represented by a general formula (G3-1); and (G3-1)

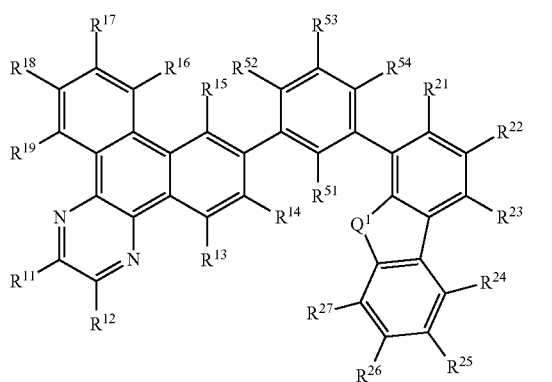

wherein:
$R^{51}$ to $R^{54}$ separately represent any one of hydrogen, an alkyl group having 1 to 4 carbon atoms; and a substituted or unsubstituted aryl group having 6 to 13 carbon atoms.

7. The compound according to claim 6, wherein the nitrogen atom has an alkyl group having 1 to 4 carbon atoms, or a substituted or unsubstituted aryl group having 6 to 13 carbon atoms.

8. A compound represented by a general formula (G2-3), (G2-3)

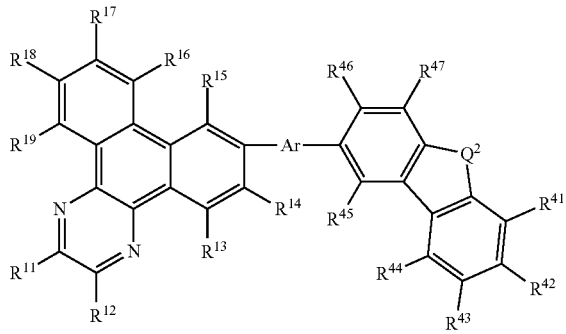

wherein:
$R^{11}$ to $R^{19}$ and $R^{41}$ to $R^{47}$ separately represent any one of hydrogen, an alkyl group having 1 to 4 carbon atoms, and a substituted or unsubstituted aryl group having 6 to 13 carbon atoms;
$Q^2$ represents any one of a sulfur atom, an oxygen atom, and a nitrogen atom; and
Ar represents a substituted or unsubstituted arylene group having 6 to 13 carbon atoms.

9. The compound according to claim 8, wherein the nitrogen atom has an alkyl group having 1 to 4 carbon atoms, or a substituted or unsubstituted aryl group having 6 to 13 carbon atoms.

10. The compound according to claim 8, wherein Ar is a substituted or unsubstituted phenylene group or a substituted or unsubstituted biphenyldiyl group.

11. The compound according to claim 8, wherein Ar is a substituted or unsubstituted m-phenylene group.

12. The compound according to claim 8,
wherein:
the compound is represented by a general formula (G3-3); and (G3-3)

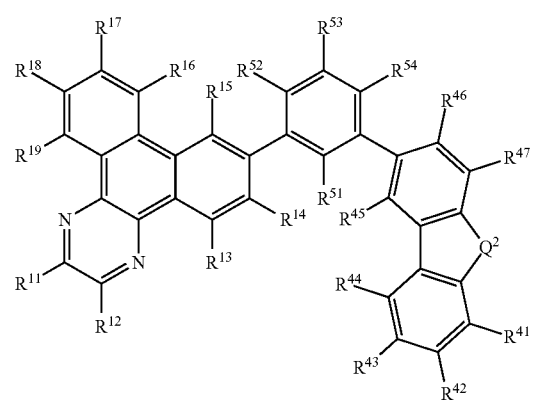

$R^{51}$ to $R^{54}$ separately represent any one of hydrogen, an alkyl group having 1 to 4 carbon atoms, and a substituted or unsubstituted aryl group having 6 to 13 carbon atoms.

13. The compound according to claim 12, wherein the nitrogen atom has an alkyl group having 1 to 4 carbon atoms or a substituted or unsubstituted aryl group having 6 to 13 carbon atoms.

* * * * *